(12) United States Patent
Blaschuk et al.

(10) Patent No.: US 7,456,153 B2
(45) Date of Patent: Nov. 25, 2008

(54) COMPOUNDS AND METHODS FOR MODULATING FUNCTIONS OF CLASSICAL CADHERINS

(75) Inventors: Orest W. Blaschuk, Westmount (CA); Stephanie D. Michaud, Hull (CA)

(73) Assignee: Adherex Technologies Inc., Ottawa (CA)

(*) Notice: Subject to any disclaimer, the term of this patent is extended or adjusted under 35 U.S.C. 154(b) by 389 days.

(21) Appl. No.: 10/714,556

(22) Filed: Nov. 14, 2003

(65) Prior Publication Data
US 2005/0129676 A1   Jun. 16, 2005

Related U.S. Application Data

(60) Provisional application No. 60/426,194, filed on Nov. 14, 2002.

(51) Int. Cl.
*A61K 38/12* (2006.01)
(52) U.S. Cl. ........................... 514/15; 424/130.1
(58) Field of Classification Search ........................ None
See application file for complete search history.

(56) References Cited

U.S. PATENT DOCUMENTS

| | | | |
|---|---|---|---|
| 5,245,012 A | 9/1993 | Lombari et al. | 530/353 |
| 5,417,224 A | 5/1995 | Petrus et al. | 128/833 |
| 5,505,956 A | 4/1996 | Kim et al. | 424/448 |
| 5,510,628 A | 4/1996 | Georger, Jr. et al. | 257/32 |
| 5,613,958 A | 3/1997 | Kochinke et al. | 604/307 |
| 6,031,072 A * | 2/2000 | Blaschuk et al. | 530/317 |
| 6,110,747 A | 8/2000 | Blaschuk et al. | 436/512 |
| 6,169,071 B1 | 1/2001 | Blaschuk et al. | 514/4 |
| 6,203,788 B1 | 3/2001 | Blaschuk et al. | 424/93.7 |
| 6,207,639 B1 | 3/2001 | Blaschuk et al. | 514/11 |
| 6,248,864 B1 | 6/2001 | Blaschuk et al. | 530/317 |
| 6,277,824 B1 | 8/2001 | Doherty et al. | 514/13 |
| 6,294,153 B1 | 9/2001 | Modi | 424/45 |
| 6,303,576 B1 | 10/2001 | Blaschuk et al. | 514/14 |
| 6,310,177 B1 | 10/2001 | Blaschuk et al. | 530/317 |
| 6,326,352 B1 | 12/2001 | Blaschuk et al. | 514/9 |
| 6,333,307 B1 | 12/2001 | Blaschuk et al. | 514/9 |
| 6,346,512 B1 | 2/2002 | Blaschuk et al. | 514/11 |
| 6,358,920 B1 | 3/2002 | Blaschuk et al. | 514/9 |
| 6,391,855 B1 | 5/2002 | Blaschuk et al. | 514/17 |
| 6,417,325 B1 | 7/2002 | Blaschuk et al. | 530/317 |
| 6,433,149 B1 | 8/2002 | Blaschuk et al. | 530/412 |
| 6,465,427 B1 | 10/2002 | Blaschuk et al. | 514/9 |
| 6,472,367 B1 | 10/2002 | Blaschuk et al. | 514/9 |
| 6,472,368 B1 | 10/2002 | Doherty et al. | 514/9 |
| 6,562,786 B1 | 5/2003 | Blaschuk et al. | 514/11 |

FOREIGN PATENT DOCUMENTS

| | | |
|---|---|---|
| EP | 0 566 816 A1 | 10/1993 |
| EP | 0 821 060 A | 1/1998 |
| WO | WO91/18098 A | 11/1991 |
| WO | WO00/20607 A | 4/2000 |

OTHER PUBLICATIONS

Avrahami et al., Biochemistry, 40(42) 12591-603, 2001.*
Goldman et al., FEMS Microbiology Letters, 183(2), 2090214, 2000.*
Al-Obeidi, F., et al., "Peptide and Peptidomimetic Libraries," *Molecular Biotechnology* 9(3):205-223, Jun. 1998.
Avellana-Adalid, V., et al., "Expansion of Rat Oligodendrocyte Progenitors Into Proliferative "Oligospheres" That Retain Differentiation Potential," *J. Neurosci. Res.* 45:558-570, 1996.
Baron-Van Evercooren, A., et al., "Cell-Cell Interactions During the Migration of Myelin-Forming Cells Transplanted in the Demyelinated Spinal Cord," *GLIA* 16:147-164, 1996.
Blaschuk, O., et al., "Cadherins as modulators of angiogenesis and the structural integrity of blood vessels," *Cancer and Metastasis Reviews* 19:1-5, 2000.
Blaschuk, O., et al., "Estradiol Stimulates Cadherin Expression in Rat Granulosa Cells," *Developmental Biology* 136:564-567, 1989.
Blaschuk, O., et al., "Identification of a Cadherin Cell Adhesion Recognition Sequence," *Developmental Biology* 139:227-229, 1990.
Blaschuk, O., et al., "Identification of a Conserved Region Common to Cadherins and Influenza Strain A Hemagglutinins," *J. Mol. Biol.* 211:679-682, 1990.
Cardarelli, P., et al., "The Collagen Receptor α2β1, from MG-63 and HT1080 Cells, Interacts with a Cyclic RGD Peptide," *J. Biol. Chem.* 267(32):23159-23164, 1992.
Cepek, K., et al., "Expression of a candidate cadherin in T lymphocytes," *Proc. Natl. Acad. Sci. USA* 93:6567-6571, 1996.
Doherty, P., et al., "Signal transduction events underlying neurite outgrowth stimulated by cell adhesion molecules," *Curr. Op. Neurobiol* 4:49-55, 1994.
Doherty, P., et al., "The Neural Cell Adhesion Molecule and Synaptic Plasticity," *J. Neurobiology* 26(3):437-446, 1995.
Doherty, P., et al., "CAM-FGF Receptor Interactions: A Model for Axonal Growth," *Mol. Cell. Neurosci.* 8:99-111, 1996.
Eichler, J., et al., "Peptide, Peptidomimetic, and Organic Synthetic Combinatorial Libraries," *Medicinal Research Review* 15(6):481-496, Nov. 1995.
Fannon, A., et al., "A Model for Central Synaptic Junctional Complex Formation Based on the Differential Adhesive Specificities of the Cadherins," *Neuron* 17:423-434, 1996.

(Continued)

*Primary Examiner*—Christopher R. Tate
*Assistant Examiner*—Roy Teller
(74) *Attorney, Agent, or Firm*—Seed IP Law Group PLLC

(57) ABSTRACT

Modulating agents and methods for enhancing or inhibiting classical cadherin-mediated functions are provided. The modulating agents comprise at least a tryptophan-containing cell adhesion recognition sequence of a classical cadherin molecule, a conservative analogue or peptidomimetic thereof, or an antibody or fragment thereof that specifically binds to such a cell adhesion recognition sequence. Modulating agents may additionally comprise one or more cell adhesion recognition sequences recognized by cadherins and/or other adhesion molecules. Such modulating agents may, but need not, be linked to a targeting agent, pharmaceutically active substance and/or support material.

9 Claims, 8 Drawing Sheets

OTHER PUBLICATIONS

Franz, T., "The Finite Dose Technique as a Valid in vitro Model for the Study of Percutaneous Absorption in Man," *Curr. Prob. Dermatol.* 7:58-68, 1978.

Franz, J., "Percutaneous Absorption. On the Relevance of In Vitro Data," *The Journal of Invest. Dermatol.* 64:190-195, 1975.

Gillespie, P., et al., "Conformational Analysis of Dipeptide Mimetics," *Peptide Science* 43(3):191-217, 1997.

Groves, A.K., et al., "Repair of demyelinated lesions by transplantation of purified 0-2A progenitor cells," *Nature* 362:453-455, 1993.

Guilford, "E-Cadherin Downregulation in Cancer: Fuel on the Fire?" *Molecular Medicine Today* 5(4):172:177, Apr. 1999 (XP001155310 ISSN:1357-4310).

Hall, H., et al., "Review: A Role for the FGF Receptor in the Axonal Growth Response Stimulated by Cell Adhesion Molecules?" *Cell Adhesion and Communication* 3:441-450, 1996.

Hruby, V., et al., "Synthesis of oligopeptide and peptidomimetic libraries," *Current Opinion in Chemical Biology* 1:114-119, 1997.

Iruela-Arispe et al., "Expression of SPARC during Development of the Chicken Chorioallantoic Membrane: Evidence for Regulated Proteolysis In Vivo," *Molecular Biology of the Cell* 6:327-343, 1995.

Jankowski, J.A.Z., et al., "Alterations in Classical Cadherins Associated with Progreession in Ulcerative and Crohn's Colitis," *Laboratory Investigation* 78(9):1155-1167, Sep. 1998.

Laird, W., et al., "Gap Junction Turnover, Intracellular Trafficking, and Phosphorylation Of Connexin43 in Brefeldin A-treated Rat Mammary Tumor Cells," *J. Cell Biol.* 131(5):1193-1203, Dec. 1995.

Lee, M-G., et al., "Expression of the Homotypic Adhesion Molecule E-Cadherin by Immature Murine Thymocytes and Thymic Epithelial Cells[1]," *J. Immunol.* 152:5653-5659, 1994.

Li, G., et al., "N-Cadherin-mediated Intercellular Interactions Promote Survival and Migration of Melanoma Cells," *Cancer Research, Amer. Assoc. for Cancer Research* 61(9):3819-3825, May 1, 2001.

Martin, K., et al., "Cell Adhesion Molecules, CREB, and the Formation of New Synaptic Connections," *Neuron* 17:567-570, 1996.

Martin-Padura, I., et al., "Junctional Adhesion Molecule, a Novel Member of the Immunoglobulin Superfamily That Distributes at Intercellular Junctions and Modulates Monocyte Transmigration," *J. Cell. Biol.* 142(1):117-127, 1998.

Munro, S., et al., "Characterization of Cadherins Expressed by Murine Thymocytes," *Cellular Immunology* 169:309-312, 1996.

Munro, S., et al., *Cell Adhesion and Invasion in Cancer Metastasis*, RG Landes Co., Austin, TX, 1996, Chap. 3, "The Structure, Function and Regulation of Cadherins," pp. 17-34.

Newton, S., et al., "N-Cadherin Mediates Sertoli Cell-Spermatogenic Cell Adhesion," *Develop. Dynamics* 197:1-13, 1993.

Noë et al., "Inhibition of adhesion and induction of epithelial cell invasion by HAV-containing E-cadherin-specific peptides," *Journal of Cell Science* 112(1):127-135, Jan. 1999.

Nollett et al, "Phylogenetic Analysis of the Cadherin Superfamily allows Identification of Six Major Subfamilies Besides Several Solitary Members," *Journal of Molecular Biology* 299:551-572, 2000.

Overduin, M., et al., "Solution Structure of the Epithelial Cadherin Domain Responsible for Selective Cell Adhesion," *Science* 267:386-389, Jan. 20, 1995.

Purohit, S., et al., "Impaired E-cadherin expression in human spermatozoa in a male factor infertility subset signifies E-cadherin-mediated adhesion mechanisms operative in sperm-oolemma interactions," *Biochemical and Biophysical Communications* 316:903-909, 2004.

Ripka, A., et al., "Peptidomimetic design," *Current Opinion in Chemical Biology* 2:441-452, 1998.

Rosenberg, P., et al., "A Potential Role of R-cadherin in Striated Muscle Formation," *Developmental Biology* 187:55-70, 1997.

Rowlands, T., et al., "Cadherins: Crucial regulators of structure and function in reproductive tissues," *Reviews in Reproduction* 5:53-61, 2000.

Safell, J., et al., "Expression of a Dominant Negative FGF Receptor Inhibits Axonal Growth and FGF Receptor Phosphorylation Stimulated by CAMs," *Neuron* 18:231-242, 1997.

Tamura, K., et al., "Structure-Function Analysis of Cell Adhesion by Neural (N-) Cadherin," *Neuron* 20:1153-1163, Jun. 1998.

Tsutsui et al., "Expression of Cadherin-Catenin Complexes in Human Leukemia Cell Lines," *J. Biochem.* 120:1034-1039, 1996.

Williams, G., et al., "Dimeric Versions of Two Short N-cadherin Binding Motifs (HAVDI and INPISG) Function as N-Cadherin Agonists," *J. Biol. Chem.* 277(6):4361-4367, 2002.

Williams, E., et al., "Activation of the FGF Receptor Underlies Neurite Outgrowth Stimulated by L1, N-CAM, and N-Cadherin," *Neuron* 13:583-594, Sep. 1994.

* cited by examiner

```
N-cad human    DWVIPPINLPENSRGPFPQELVRIRSDRDKNLSLRYSVTGPGADQPPTGIFILNPISGQLSVTKPLDREQIARFHLRAHAVDINGNQVENPIDIVINVIDMNDNRPEF
N-cad mouse    DWVIPPINLPENSRGPFPQELVRIRSDRDKNLSLRYSVTGPGADQPPTGIFILNPISGQLSVTKPLDREQIARFHLRAHAVDINGNQVENPIDIVINVIDMNDNRPEF
N-cad cow      DWVIPPINLPENSRGPFPQELVRIRSDRDKNLSLRYSVTGPGADQPPTGIFIINPISGQLSVTKPLDRELIARFHLRAHAVDINGNQVENPIDIVINVIDMNDNRPEF
P-cad human    DWVVAPISVPENGKGPFPQRLNQLKSNKDRDTKIFYSITGPGADSPPEGVFAVEKETGWLLLNKPLDREEIAKYELFGHAVSENGASVEDPMNISIIVTDQNDHKPKF
P-cad mouse    EWVMPPIFVPENGKGPFPQRLNQLKSNKDRGTKIFYSITGPGADSPPEGVFTIEKESGWLLHMPLDREKIVKYELYGHAVSENGASVEEPMNISIIVTDQNDKPKF
E-cad human    DWVIPPISCPENEKGPFPKNLVQIKSNKDKEGKVFYSITGQGADTPPVGVFIIERETGWLKVTEPLDRERIATYTLFSHAVSSNGNAVEDPMEILITVTDQNDKPEF
E-cad mouse    DWVIPPISCPENEKGEFPKNLVQIKSNRDKETKVFYSITGQGADKPPVGVFIIERETGWLKVTQPLDREAIAKYILYSHAVSSNGEAVEDPMEIVITVTDQNDNRPEF
R-cad human    DWVIPPINVPENSRGPFPQQLVRIRSDKDNDIPIRYSITGVGADQPPMEVFSIDSMSGRMYVTRPMDREEHASYHLRAHAVDMNGNKVENPIDLYIYVIDMNDNRPEF
R-cad mouse    DWVIPPINVPENSRGPFPQQLVRIRSDKDNDIPIRYSITGVGADQPPMEVFNIDSMSGRMYVTRPMDREERASYHLRAHAVDMNGNKVENPIDLYIYVIDMNDNRPEF
```

*FIG. 2*

H-DWVIPP-NH2

SEQUENCE LISTING

```
<160> NUMBER OF SEQ ID NOS: 179

<210> SEQ ID NO 1
<211> LENGTH: 6
<212> TYPE: PRT
<213> ORGANISM: Unknown
<220> FEATURE:
<223> OTHER INFORMATION: Consensus sequence found in certain atypical
      cadherin Trp-containing CAR sequences.
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 4
<223> OTHER INFORMATION: Xaa = Ile, Val or Met
<220> FEATURE:
<221> NAME/KEY: VARIANT
<222> LOCATION: 5
<223> OTHER INFORMATION: Xaa = Pro or Ala

<400> SEQUENCE: 1

Xaa Trp Val Xaa Xaa Pro
 1               5

<210> SEQ ID NO 2
<211> LENGTH: 4
<212> TYPE: PRT
<213> ORGANISM: Unknown
<220> FEATURE:
<223> OTHER INFORMATION: Calcium binding motif

<400> SEQUENCE: 2

Leu Asp Arg Glu
 1

<210> SEQ ID NO 3
<211> LENGTH: 6
<212> TYPE: PRT
<213> ORGANISM: Unknown
<220> FEATURE:
<223> OTHER INFORMATION: Exemplary cell adhesion modulating agent.

<400> SEQUENCE: 3
```

Asp Trp Val Ile Pro Pro
1               5

<210> SEQ ID NO 4
<211> LENGTH: 5
<212> TYPE: PRT
<213> ORGANISM: Unknown
<220> FEATURE:
<223> OTHER INFORMATION: Calcium binding motif
<220> FEATURE:
<221> NAME/KEY: VARIANT
<222> LOCATION: 2
<223> OTHER INFORMATION: Xaa = any amino acid

<400> SEQUENCE: 4

Asp Xaa Asn Asp Asn
1               5

<210> SEQ ID NO 5
<211> LENGTH: 4
<212> TYPE: PRT
<213> ORGANISM: Unknown
<220> FEATURE:
<223> OTHER INFORMATION: Exemplary Trp-containing CAR sequences or
      conservative analogues thereof

<400> SEQUENCE: 5

Asp Trp Val Ile
1

<210> SEQ ID NO 6
<211> LENGTH: 4
<212> TYPE: PRT
<213> ORGANISM: Unknown
<220> FEATURE:
<223> OTHER INFORMATION: Exemplary Trp-containing CAR sequences or
      conservative analogues thereof

<400> SEQUENCE: 6

Asp Trp Val Val
1

<210> SEQ ID NO 7
<211> LENGTH: 4
<212> TYPE: PRT
<213> ORGANISM: Unknown
<220> FEATURE:
<223> OTHER INFORMATION: Exemplary Trp-containing CAR sequences or
      conservative analogues thereof

<400> SEQUENCE: 7

Asp Trp Val Met
1

<210> SEQ ID NO 8
<211> LENGTH: 5
<212> TYPE: PRT
<213> ORGANISM: unknown
<220> FEATURE:
<223> OTHER INFORMATION: Exemplary Trp-containing CAR sequences or
      conservative analogues thereof

<400> SEQUENCE: 8

Asp Trp Val Ile Pro
1               5

<210> SEQ ID NO 9

```
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 9

Asp Trp Val Ile Ala
 1               5

<210> SEQ ID NO 10
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 10

Asp Trp Val Val Pro
 1               5

<210> SEQ ID NO 11
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 11

Asp Trp Val Val Pro Pro
 1               5

<210> SEQ ID NO 12
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 12

Asp Trp Val Val Ala Pro
 1               5

<210> SEQ ID NO 13
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 13

Asp Trp Val Met Pro Pro
 1               5

<210> SEQ ID NO 14
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 14
```

-continued

```
Asp Trp Val Met Ala Pro
1               5

<210> SEQ ID NO 15
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 15

Glu Trp Val Ile
1

<210> SEQ ID NO 16
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 16

Glu Trp Val Val
1

<210> SEQ ID NO 17
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 17

Glu Trp Val Met
1

<210> SEQ ID NO 18
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 18

Glu Trp Val Ile Pro
1               5

<210> SEQ ID NO 19
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 19

Glu Trp Val Ile Ala
1               5

<210> SEQ ID NO 20
<211> LENGTH: 5
<212> TYPE: PRT
<213> ORGANISM: UNKNOWN
<220> FEATURE:
```

```
<223> OTHER INFORMATION: Exemplary Trp-containing CAR sequences or
      conservative analogues thereof

<400> SEQUENCE: 20

Glu Trp Val Val Pro
 1               5

<210> SEQ ID NO 21
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 21

Glu Trp Val Val Pro Pro
 1               5

<210> SEQ ID NO 22
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 22

Glu Trp Val Val Ala Pro
 1               5

<210> SEQ ID NO 23
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 23

Glu Trp Val Met Pro Pro
 1               5

<210> SEQ ID NO 24
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 24

Glu Trp Val Met Ala Pro
 1               5

<210> SEQ ID NO 25
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 25

Trp Val Ile Pro
 1
```

```
<210> SEQ ID NO 26
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 26

Trp Val Ile Ala
 1

<210> SEQ ID NO 27
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 27

Trp Val Val Pro
 1

<210> SEQ ID NO 28
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 28

Trp Val Val Ala
 1

<210> SEQ ID NO 29
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 29

Trp Val Met Pro
 1

<210> SEQ ID NO 30
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 30

Trp Val Met Ala
 1

<210> SEQ ID NO 31
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 31
```

Trp Val Ile Pro Pro
1               5

<210> SEQ ID NO 32
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 32

Trp Val Ile Ala Pro
1               5

<210> SEQ ID NO 33
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 33

Trp Val Val Pro Pro
1               5

<210> SEQ ID NO 34
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 34

Trp Val Val Ala Pro
1               5

<210> SEQ ID NO 35
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 35

Trp Val Met Pro Pro
1               5

<210> SEQ ID NO 36
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 36

Trp Val Met Ala Pro
1               5

<210> SEQ ID NO 37
<211> LENGTH: 4
<212> TYPE: PRT
<213> ORGANISM: UNKNOWN

```
<220> FEATURE:
<223> OTHER INFORMATION: Exemplary Trp-containing CAR sequences or
      conservative analogues thereof

<400> SEQUENCE: 37

Asp Trp Ile Ile
  1

<210> SEQ ID NO 38
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 38

Asp Trp Ile Val
  1

<210> SEQ ID NO 39
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 39

Asp Trp Ile Met
  1

<210> SEQ ID NO 40
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 40

Asp Trp Ile Ile Pro
  1               5

<210> SEQ ID NO 41
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 41

Asp Trp Ile Ile Ala
  1               5

<210> SEQ ID NO 42
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 42

Asp Trp Ile Val Pro
  1               5
```

```
<210> SEQ ID NO 43
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 43

Asp Trp Ile Val Pro Pro
 1               5

<210> SEQ ID NO 44
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 44

Asp Trp Ile Val Ala Pro
 1               5

<210> SEQ ID NO 45
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 45

Asp Trp Ile Met Pro Pro
 1               5

<210> SEQ ID NO 46
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 46

Asp Trp Ile Met Ala Pro
 1               5

<210> SEQ ID NO 47
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 47

Glu Trp Ile Ile
 1

<210> SEQ ID NO 48
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof
```

```
<400> SEQUENCE: 48

Glu Trp Ile Val
 1

<210> SEQ ID NO 49
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 49

Glu Trp Ile Met
 1

<210> SEQ ID NO 50
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 50

Glu Trp Ile Ile Pro
 1               5

<210> SEQ ID NO 51
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 51

Glu Trp Ile Ile Ala
 1               5

<210> SEQ ID NO 52
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 52

Glu Trp Ile Val Pro
 1               5

<210> SEQ ID NO 53
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 53

Glu Trp Ile Val Pro Pro
 1               5

<210> SEQ ID NO 54
<211> LENGTH: 6
<212> TYPE: PRT
```

```
<213> ORGANISM: UNKNOWN
<220> FEATURE:
<223> OTHER INFORMATION: Exemplary Trp-containing CAR sequences or
      conservative analogues thereof

<400> SEQUENCE: 54

Glu Trp Ile Val Ala Pro
1               5

<210> SEQ ID NO 55
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 55

Glu Trp Ile Met Pro Pro
1               5

<210> SEQ ID NO 56
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 56

Glu Trp Ile Met Ala Pro
1               5

<210> SEQ ID NO 57
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 57

Trp Ile Ile Pro
1

<210> SEQ ID NO 58
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 58

Trp Ile Ile Ala
1

<210> SEQ ID NO 59
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 59

Trp Ile Val Pro
1
```

```
<210> SEQ ID NO 60
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 60

Trp Ile Val Ala
 1

<210> SEQ ID NO 61
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 61

Trp Ile Met Pro
 1

<210> SEQ ID NO 62
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 62

Trp Ile Met Ala
 1

<210> SEQ ID NO 63
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 63

Trp Ile Ile Pro Pro
 1               5

<210> SEQ ID NO 64
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 64

Trp Ile Ile Ala Pro
 1               5

<210> SEQ ID NO 65
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof
```

```
<400> SEQUENCE: 65

Trp Ile Val Pro Pro
1               5

<210> SEQ ID NO 66
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 66

Trp Ile Val Ala Pro
1               5

<210> SEQ ID NO 67
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 67

Trp Ile Met Pro Pro
1               5

<210> SEQ ID NO 68
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 68

Trp Ile Met Ala Pro
1               5

<210> SEQ ID NO 69
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 69

Asp Trp Leu Ile
1

<210> SEQ ID NO 70
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 70

Asp Trp Leu Val
1

<210> SEQ ID NO 71
<211> LENGTH: 4
```

```
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 71

Asp Trp Leu Met
 1

<210> SEQ ID NO 72
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 72

Asp Trp Leu Ile Pro
 1               5

<210> SEQ ID NO 73
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 73

Asp Trp Leu Ile Ala
 1               5

<210> SEQ ID NO 74
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 74

Asp Trp Leu Val Pro
 1               5

<210> SEQ ID NO 75
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 75

Asp Trp Leu Val Pro Pro
 1               5

<210> SEQ ID NO 76
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 76

Asp Trp Leu Val Ala Pro
```

```
1               5

<210> SEQ ID NO 77
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 77

Asp Trp Leu Met Pro Pro
1               5

<210> SEQ ID NO 78
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 78

Asp Trp Leu Met Ala Pro
1               5

<210> SEQ ID NO 79
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 79

Glu Trp Leu Ile
1

<210> SEQ ID NO 80
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 80

Glu Trp Leu Val
1

<210> SEQ ID NO 81
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 81

Glu Trp Leu Met
1

<210> SEQ ID NO 82
<211> LENGTH: 5
<212> TYPE: PRT
<213> ORGANISM: UNKNOWN
<220> FEATURE:
<223> OTHER INFORMATION: Exemplary Trp-containing CAR sequences or
```

-continued

```
      conservative analogues thereof

<400> SEQUENCE: 82

Glu Trp Leu Ile Pro
1               5

<210> SEQ ID NO 83
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 83

Glu Trp Leu Ile Ala
1               5

<210> SEQ ID NO 84
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 84

Glu Trp Leu Val Pro
1               5

<210> SEQ ID NO 85
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 85

Glu Trp Leu Val Pro Pro
1               5

<210> SEQ ID NO 86
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 86

Glu Trp Leu Val Ala Pro
1               5

<210> SEQ ID NO 87
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 87

Glu Trp Leu Met Pro Pro
1               5

<210> SEQ ID NO 88
```

```
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 88

Glu Trp Leu Met Ala Pro
  1               5

<210> SEQ ID NO 89
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 89

Trp Leu Ile Pro
  1

<210> SEQ ID NO 90
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 90

Trp Leu Ile Ala
  1

<210> SEQ ID NO 91
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 91

Trp Leu Val Pro
  1

<210> SEQ ID NO 92
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 92

Trp Leu Val Ala
  1

<210> SEQ ID NO 93
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 93
```

```
Trp Leu Met Pro
1

<210> SEQ ID NO 94
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 94

Trp Leu Met Ala
1

<210> SEQ ID NO 95
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 95

Trp Leu Ile Pro Pro
1               5

<210> SEQ ID NO 96
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 96

Trp Leu Ile Ala Pro
1               5

<210> SEQ ID NO 97
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 97

Trp Leu Val Pro Pro
1               5

<210> SEQ ID NO 98
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 98

Trp Leu Val Ala Pro
1               5

<210> SEQ ID NO 99
<211> LENGTH: 5
<212> TYPE: PRT
<213> ORGANISM: UNKNOWN
<220> FEATURE:
```

-continued

```
<223> OTHER INFORMATION: Exemplary Trp-containing CAR sequences or
      conservative analogues thereof

<400> SEQUENCE: 99

Trp Leu Met Pro Pro
 1               5

<210> SEQ ID NO 100
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 100

Trp Leu Met Ala Pro
 1               5

<210> SEQ ID NO 101
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 101

Asp Trp Val Leu
 1

<210> SEQ ID NO 102
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 102

Asp Trp Ile Leu
 1

<210> SEQ ID NO 103
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 103

Asp Trp Leu Leu
 1

<210> SEQ ID NO 104
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 104

Glu Trp Val Leu
 1
```

<210> SEQ ID NO 105
<211> LENGTH: 4
<212> TYPE: PRT
<213> ORGANISM: UNKNOWN
<220> FEATURE:
<223> OTHER INFORMATION: Exemplary Trp-containing CAR sequences or
    conservative analogues thereof

<400> SEQUENCE: 105

Glu Trp Ile Leu
 1

<210> SEQ ID NO 106
<211> LENGTH: 4
<212> TYPE: PRT
<213> ORGANISM: UNKNOWN
<220> FEATURE:
<223> OTHER INFORMATION: Exemplary Trp-containing CAR sequences or
    conservative analogues thereof

<400> SEQUENCE: 106

Glu Trp Leu Leu
 1

<210> SEQ ID NO 107
<211> LENGTH: 5
<212> TYPE: PRT
<213> ORGANISM: UNKNOWN
<220> FEATURE:
<223> OTHER INFORMATION: Exemplary Trp-containing CAR sequences or
    conservative analogues thereof

<400> SEQUENCE: 107

Asp Trp Val Leu Pro
 1               5

<210> SEQ ID NO 108
<211> LENGTH: 5
<212> TYPE: PRT
<213> ORGANISM: UNKNOWN
<220> FEATURE:
<223> OTHER INFORMATION: Exemplary Trp-containing CAR sequences or
    conservative analogues thereof

<400> SEQUENCE: 108

Asp Trp Ile Leu Pro
 1               5

<210> SEQ ID NO 109
<211> LENGTH: 5
<212> TYPE: PRT
<213> ORGANISM: UNKNOWN
<220> FEATURE:
<223> OTHER INFORMATION: Exemplary Trp-containing CAR sequences or
    conservative analogues thereof

<400> SEQUENCE: 109

Asp Trp Leu Leu Pro
 1               5

<210> SEQ ID NO 110
<211> LENGTH: 5
<212> TYPE: PRT
<213> ORGANISM: UNKNOWN
<220> FEATURE:
<223> OTHER INFORMATION: Exemplary Trp-containing CAR sequences or
    conservative analogues thereof

<400> SEQUENCE: 110

```
Glu Trp Val Leu Pro
1               5

<210> SEQ ID NO 111
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 111

Glu Trp Ile Leu Pro
1               5

<210> SEQ ID NO 112
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 112

Glu Trp Leu Leu Pro
1               5

<210> SEQ ID NO 113
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 113

Asp Trp Val Leu Ala
1               5

<210> SEQ ID NO 114
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 114

Asp Trp Ile Leu Ala
1               5

<210> SEQ ID NO 115
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 115

Asp Trp Leu Leu Ala
1               5

<210> SEQ ID NO 116
<211> LENGTH: 5
<212> TYPE: PRT
<213> ORGANISM: UNKNOWN
```

```
<220> FEATURE:
<223> OTHER INFORMATION: Exemplary Trp-containing CAR sequences or
      conservative analogues thereof

<400> SEQUENCE: 116

Glu Trp Val Leu Ala
1               5

<210> SEQ ID NO 117
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 117

Glu Trp Ile Leu Ala
1               5

<210> SEQ ID NO 118
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 118

Glu Trp Leu Leu Ala
1               5

<210> SEQ ID NO 119
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 119

Asp Trp Val Leu Pro Pro
1               5

<210> SEQ ID NO 120
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 120

Asp Trp Ile Leu Pro Pro
1               5

<210> SEQ ID NO 121
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 121

Asp Trp Leu Leu Pro Pro
1               5
```

```
<210> SEQ ID NO 122
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 122

Glu Trp Val Leu Pro Pro
1               5

<210> SEQ ID NO 123
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 123

Glu Trp Ile Leu Pro Pro
1               5

<210> SEQ ID NO 124
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 124

Glu Trp Leu Leu Pro Pro
1               5

<210> SEQ ID NO 125
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 125

Asp Trp Val Leu Ala Pro
1               5

<210> SEQ ID NO 126
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 126

Asp Trp Ile Leu Ala Pro
1               5

<210> SEQ ID NO 127
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof
```

-continued

```
<400> SEQUENCE: 127

Asp Trp Leu Leu Ala Pro
 1               5

<210> SEQ ID NO 128
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 128

Glu Trp Val Leu Ala Pro
 1               5

<210> SEQ ID NO 129
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 129

Glu Trp Ile Leu Ala Pro
 1               5

<210> SEQ ID NO 130
<211> LENGTH: 6
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 130

Glu Trp Leu Leu Ala Pro
 1               5

<210> SEQ ID NO 131
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 131

Trp Val Leu Pro
 1

<210> SEQ ID NO 132
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 132

Trp Ile Leu Pro
 1

<210> SEQ ID NO 133
<211> LENGTH: 4
<212> TYPE: PRT
```

```
<213> ORGANISM: UNKNOWN
<220> FEATURE:
<223> OTHER INFORMATION: Exemplary Trp-containing CAR sequences or
      conservative analogues thereof

<400> SEQUENCE: 133

Trp Leu Leu Pro
 1

<210> SEQ ID NO 134
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 134

Trp Val Leu Ala
 1

<210> SEQ ID NO 135
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 135

Trp Ile Leu Ala
 1

<210> SEQ ID NO 136
<211> LENGTH: 4
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 136

Trp Leu Leu Ala
 1

<210> SEQ ID NO 137
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 137

Trp Val Leu Pro Pro
 1               5

<210> SEQ ID NO 138
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 138

Trp Ile Leu Pro Pro
 1               5
```

```
<210> SEQ ID NO 139
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 139

Trp Leu Leu Pro Pro
1               5

<210> SEQ ID NO 140
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 140

Trp Val Leu Ala Pro
1               5

<210> SEQ ID NO 141
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 141

Trp Ile Leu Ala Pro
1               5

<210> SEQ ID NO 142
<211> LENGTH: 5
<212> TYPE: PRT
<213> ORGANISM: UNKNOWN
<220> FEATURE:
<223> OTHER INFORMATION: Exemplary Trp-containing CAR sequences or
      conservative analogues thereof

<400> SEQUENCE: 142

Trp Leu Leu Ala Pro
1               5

<210> SEQ ID NO 143
<211> LENGTH: 5
<212> TYPE: PRT
<213> ORGANISM: UNKNOWN
<220> FEATURE:
<223> OTHER INFORMATION: Modulating agent

<400> SEQUENCE: 143

Asp Trp Val Val Ala
1               5

<210> SEQ ID NO 144
<211> LENGTH: 5
<212> TYPE: PRT
<213> ORGANISM: UNKNOWN
<220> FEATURE:
<223> OTHER INFORMATION: Modulating agent

<400> SEQUENCE: 144
```

```
Glu Trp Val Met Pro
1               5

<210> SEQ ID NO 145
<211> LENGTH: 5
<212> TYPE: PRT
<213> ORGANISM: UNKNOWN
<220> FEATURE:
<223> OTHER INFORMATION: Preferred CAR sequence for inclusion with a
      modulating agent

<400> SEQUENCE: 145

Tyr Ile Gly Ser Arg
1               5

<210> SEQ ID NO 146
<211> LENGTH: 10
<212> TYPE: PRT
<213> ORGANISM: UNKNOWN
<220> FEATURE:
<223> OTHER INFORMATION: Preferred CAR sequence for inclusion with a
      modulating agent

<400> SEQUENCE: 146

Lys Tyr Ser Phe Asn Tyr Asp Gly Ser Glu
1               5                   10

<210> SEQ ID NO 147
<211> LENGTH: 9
<212> TYPE: PRT
<213> ORGANISM: UNKNOWN
<220> FEATURE:
<223> OTHER INFORMATION: Preferred CAR sequence for inclusion with a
      modulating agent

<400> SEQUENCE: 147

Ser Phe Thr Ile Asp Pro Lys Ser Gly
1               5

<210> SEQ ID NO 148
<211> LENGTH: 4
<212> TYPE: PRT
<213> ORGANISM: UNKNOWN
<220> FEATURE:
<223> OTHER INFORMATION: Preferred CAR sequence for inclusion with a
      modulating agent

<400> SEQUENCE: 148

Leu Tyr His Tyr
1

<210> SEQ ID NO 149
<211> LENGTH: 8
<212> TYPE: PRT
<213> ORGANISM: UNKNOWN
<220> FEATURE:
<223> OTHER INFORMATION: Preferred CAR sequence for inclusion with a
      modulating agent
<220> FEATURE:
<221> NAME/KEY: VARIANT
<222> LOCATION: 2
<223> OTHER INFORMATION: Xaa = Lys or Arg
<220> FEATURE:
<221> NAME/KEY: VARIANT
<222> LOCATION: 3,4
<223> OTHER INFORMATION: Xaa = any amino acid
<220> FEATURE:
<221> NAME/KEY: VARIANT
<222> LOCATION: 5
```

```
<223> OTHER INFORMATION: Xaa = Ser or Ala
<220> FEATURE:
<221> NAME/KEY: VARIANT
<222> LOCATION: 6
<223> OTHER INFORMATION: Xaa = Tyr or Phe
<220> FEATURE:
<221> NAME/KEY: VARIANT
<222> LOCATION: 7
<223> OTHER INFORMATION: Xaa = any amino acid

<400> SEQUENCE: 149

Trp Xaa Xaa Xaa Xaa Xaa Xaa Gly
 1               5

<210> SEQ ID NO 150
<211> LENGTH: 9
<212> TYPE: PRT
<213> ORGANISM: UNKNOWN
<220> FEATURE:
<223> OTHER INFORMATION: Preferred CAR sequence for inclusion with a
      modulating agent
<220> FEATURE:
<221> NAME/KEY: VARIANT
<222> LOCATION: 1,3
<223> OTHER INFORMATION: Xaa = any amino acid
<220> FEATURE:
<221> NAME/KEY: VARIANT
<222> LOCATION: 4
<223> OTHER INFORMATION: Xaa = Ile, Leu or Val
<220> FEATURE:
<221> NAME/KEY: VARIANT
<222> LOCATION: 5
<223> OTHER INFORMATION: Xaa = Asp, Asn or Glu
<220> FEATURE:
<221> NAME/KEY: VARIANT
<222> LOCATION: 6,7
<223> OTHER INFORMATION: Xaa = any amino acid
<220> FEATURE:
<221> NAME/KEY: VARIANT
<222> LOCATION: 8
<223> OTHER INFORMATION: Xaa= Ser, Thr or Asn

<400> SEQUENCE: 150

Xaa Phe Xaa Xaa Xaa Xaa Xaa Xaa Gly
 1               5

<210> SEQ ID NO 151
<211> LENGTH: 4
<212> TYPE: PRT
<213> ORGANISM: UNKNOWN
<220> FEATURE:
<223> OTHER INFORMATION: Representative claudin CAR sequence

<400> SEQUENCE: 151

Ile Tyr Ser Tyr
 1

<210> SEQ ID NO 152
<211> LENGTH: 4
<212> TYPE: PRT
<213> ORGANISM: UNKNOWN
<220> FEATURE:
<223> OTHER INFORMATION: Representative claudin CAR sequence

<400> SEQUENCE: 152

Thr Ser Ser Tyr
 1

<210> SEQ ID NO 153
<211> LENGTH: 4
<212> TYPE: PRT
```

```
<213> ORGANISM: UNKNOWN
<220> FEATURE:
<223> OTHER INFORMATION: Representative claudin CAR sequence

<400> SEQUENCE: 153

Val Thr Ala Phe
1

<210> SEQ ID NO 154
<211> LENGTH: 4
<212> TYPE: PRT
<213> ORGANISM: UNKNOWN
<220> FEATURE:
<223> OTHER INFORMATION: Representative claudin CAR sequence

<400> SEQUENCE: 154

Val Ser Ala Phe
1

<210> SEQ ID NO 155
<211> LENGTH: 14
<212> TYPE: PRT
<213> ORGANISM: UNKNOWN
<220> FEATURE:
<223> OTHER INFORMATION: Trp-containing CAR sequence that may be linked
      in tandem.

<400> SEQUENCE: 155

Cys Asp Trp Val Ile Pro Pro Asp Trp Val Ile Pro Pro Cys
1               5                   10

<210> SEQ ID NO 156
<211> LENGTH: 14
<212> TYPE: PRT
<213> ORGANISM: UNKNOWN
<220> FEATURE:
<223> OTHER INFORMATION: Trp-containing CAR sequence that may be linked
      in tandem.

<400> SEQUENCE: 156

Cys Asp Trp Val Ile Pro Pro Pro Pro Ile Val Trp Asp Cys
1               5                   10

<210> SEQ ID NO 157
<211> LENGTH: 14
<212> TYPE: PRT
<213> ORGANISM: UNKNOWN
<220> FEATURE:
<223> OTHER INFORMATION: Trp-containing CAR sequence that may be linked
      in tandem.

<400> SEQUENCE: 157

Cys Pro Pro Ile Val Trp Asp Asp Trp Val Ile Pro Pro Cys
1               5                   10

<210> SEQ ID NO 158
<211> LENGTH: 4
<212> TYPE: PRT
<213> ORGANISM: UNKNOWN
<220> FEATURE:
<223> OTHER INFORMATION: Sequence which is reacted with the carboxylic
      acid as a method of carbodiimide-mediated lactam
      formation.

<400> SEQUENCE: 158

Glu Asp Ala Cys
1
```

<210> SEQ ID NO 159
<211> LENGTH: 4
<212> TYPE: PRT
<213> ORGANISM: UNKNOWN
<220> FEATURE:
<223> OTHER INFORMATION: Sequence which is reacted with the carboxylic
      acid as a method of carbodiimide-mediated lactam formation.

<400> SEQUENCE: 159

Asp Cys Cys Ile
 1

<210> SEQ ID NO 160
<211> LENGTH: 48
<212> TYPE: PRT
<213> ORGANISM: uNKNOWN
<220> FEATURE:
<223> OTHER INFORMATION: Occludin CAR sequence

<400> SEQUENCE: 160

Gly Val Asn Pro Thr Ala Gln Ser Ser Gly Ser Leu Tyr Gly Ser Gln
 1               5                  10                  15

Ile Tyr Ala Leu Cys Asn Gln Phe Tyr Thr Pro Ala Ala Thr Gly Leu
                20                  25                  30

Tyr Val Asp Gln Tyr Leu Tyr His Tyr Cys Val Val Asp Pro Gln Glu
            35                  40                  45

<210> SEQ ID NO 161
<211> LENGTH: 6
<212> TYPE: PRT
<213> ORGANISM: UNKNOWN
<220> FEATURE:
<223> OTHER INFORMATION: Trp-containing peptide

<400> SEQUENCE: 161

Ala Trp Val Ile Pro Pro
 1               5

<210> SEQ ID NO 162
<211> LENGTH: 6
<212> TYPE: PRT
<213> ORGANISM: UNKNOWN
<220> FEATURE:
<223> OTHER INFORMATION: Trp-containing peptide

<400> SEQUENCE: 162

Asp Trp Val Ile Ala Pro
 1               5

<210> SEQ ID NO 163
<211> LENGTH: 6
<212> TYPE: PRT
<213> ORGANISM: UNKNOWN
<220> FEATURE:
<223> OTHER INFORMATION: Trp-containing peptide

<400> SEQUENCE: 163

Asp Trp Val Ile Pro Ala
 1               5

<210> SEQ ID NO 164
<211> LENGTH: 6
<212> TYPE: PRT
<213> ORGANISM: UNKNOWN
<220> FEATURE:
<223> OTHER INFORMATION: Trp-containing peptide

```
<400> SEQUENCE: 164

Asp Trp Val Ala Pro Pro
1               5

<210> SEQ ID NO 165
<211> LENGTH: 6
<212> TYPE: PRT
<213> ORGANISM: UNKNOWN
<220> FEATURE:
<223> OTHER INFORMATION: Trp-containing peptide

<400> SEQUENCE: 165

Pro Trp Val Ile Pro Pro
1               5

<210> SEQ ID NO 166
<211> LENGTH: 26
<212> TYPE: DNA
<213> ORGANISM: Artificial Sequence
<220> FEATURE:
<223> OTHER INFORMATION: Forward primer

<400> SEQUENCE: 166
tggtcgtgcc gctgcctcct cctcct                                       26

<210> SEQ ID NO 167
<211> LENGTH: 27
<212> TYPE: DNA
<213> ORGANISM: Artificial Sequence
<220> FEATURE:
<223> OTHER INFORMATION: Reverse  primer

<400> SEQUENCE: 167
tgccaaagcc tccagcaagc actgtgc                                      27

<210> SEQ ID NO 168
<211> LENGTH: 6
<212> TYPE: PRT
<213> ORGANISM: Artificial Sequence
<220> FEATURE:
<223> OTHER INFORMATION: Trp-containing CAR sequence
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 4
<223> OTHER INFORMATION: Xaa = Ile, Val or Met
<220> FEATURE:
<221> NAME/KEY: VARIANT
<222> LOCATION: 5
<223> OTHER INFORMATION: Xaa = Pro or Ala

<400> SEQUENCE: 168

Xaa Trp Val Xaa Xaa Pro
1               5

<210> SEQ ID NO 169
<211> LENGTH: 108
<212> TYPE: PRT
<213> ORGANISM: Homo sapiens

<400> SEQUENCE: 169

Asp Trp Val Ile Pro Pro Ile Asn Leu Pro Glu Asn Ser Arg Gly Pro
1               5                   10                  15
```

```
Phe Pro Gln Glu Leu Val Arg Ile Arg Ser Asp Arg Asp Lys Asn Leu
             20                  25                  30

Ser Leu Arg Tyr Ser Val Thr Gly Pro Gly Ala Asp Gln Pro Pro Thr
         35                  40                  45

Gly Ile Phe Ile Leu Asn Pro Ile Ser Gly Gln Leu Ser Val Thr Lys
 50                  55                  60

Pro Leu Asp Arg Glu Gln Ile Ala Arg Phe His Leu Arg Ala His Ala
 65                  70                  75                  80

Val Asp Ile Asn Gly Asn Gln Val Glu Asn Pro Ile Asp Ile Val Ile
                 85                  90                  95

Asn Val Ile Asp Met Asn Asp Asn Arg Pro Glu Phe
                100                 105
```

<210> SEQ ID NO 170
<211> LENGTH: 108
<212> TYPE: PRT
<213> ORGANISM: Mus musculus

<400> SEQUENCE: 170

```
Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
             20                  25                  30

Ser Leu Arg Tyr Ser Val Thr Gly Pro Gly Ala Asp Gln Pro Pro Thr
         35                  40                  45

Gly Ile Phe Ile Ile Asn Pro Ile Ser Gly Gln Leu Ser Val Thr Lys
 50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                 85                  90                  95

Asn Val Ile Asp Met Asn Asp Asn Arg Pro Glu Phe
                100                 105
```

<210> SEQ ID NO 171
<211> LENGTH: 108
<212> TYPE: PRT
<213> ORGANISM: Bos tarus

<400> SEQUENCE: 171

```
Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
             20                  25                  30

Ser Leu Arg Tyr Ser Val Thr Gly Pro Gly Ala Asp Gln Pro Pro Thr
         35                  40                  45

Gly Ile Phe Ile Ile Asn Pro Ile Ser Gly Gln Leu Ser Val Thr Lys
 50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                 85                  90                  95

Asn Val Ile Asp Met Asn Asp Asn Arg Pro Glu Phe
                100                 105
```

<210> SEQ ID NO 172
<211> LENGTH: 108

```
<212> TYPE: PRT
<213> ORGANISM: Homo sapiens

<400> SEQUENCE: 172

Asp Trp Val Val Ala Pro Ile Ser Val Pro Glu Asn Gly Lys Gly Pro
 1               5                  10                  15

Phe Pro Gln Arg Leu Asn Gln Leu Lys Ser Asn Lys Asp Arg Asp Thr
            20                  25                  30

Lys Ile Phe Tyr Ser Ile Thr Gly Pro Gly Ala Asp Ser Pro Pro Glu
        35                  40                  45

Gly Val Phe Ala Val Glu Lys Glu Thr Gly Trp Leu Leu Leu Asn Lys
50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe
            100                 105

<210> SEQ ID NO 173
<211> LENGTH: 108
<212> TYPE: PRT
<213> ORGANISM: Mus musculus

<400> SEQUENCE: 173

Glu Trp Val Met Pro Pro Ile Phe Val Pro Glu Asn Gly Lys Gly Pro
 1               5                  10                  15

Phe Pro Gln Arg Leu Asn Gln Leu Lys Ser Asn Lys Asp Arg Gly Thr
            20                  25                  30

Lys Ile Phe Tyr Ser Ile Thr Gly Pro Gly Ala Asp Ser Pro Pro Glu
        35                  40                  45

Gly Val Phe Thr Ile Glu Lys Glu Ser Gly Trp Leu Leu Leu His Met
50                  55                  60

Pro Leu Asp Arg Glu Lys Ile Val Lys Tyr Glu Leu Tyr Gly His Ala
65                  70                  75                  80

Val Ser Glu Asn Gly Ala Ser Val Glu Glu Pro Met Asn Ile Ser Ile
                85                  90                  95

Ile Val Thr Asp Gln Asn Asp Asn Lys Pro Lys Phe
            100                 105

<210> SEQ ID NO 174
<211> LENGTH: 108
<212> TYPE: PRT
<213> ORGANISM: Homo sapiens

<400> SEQUENCE: 174

Asp Trp Val Ile Pro Pro Ile Ser Cys Pro Glu Asn Glu Lys Gly Pro
 1               5                  10                  15

Phe Pro Lys Asn Leu Val Gln Ile Lys Ser Asn Lys Asp Lys Glu Gly
            20                  25                  30

Lys Val Phe Tyr Ser Ile Thr Gly Gln Gly Ala Asp Thr Pro Pro Val
        35                  40                  45

Gly Val Phe Ile Ile Glu Arg Glu Thr Gly Trp Leu Lys Val Thr Glu
50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
```

```
                    85                  90                  95

Thr Val Thr Asp Gln Asn Asp Asn Lys Pro Glu Phe
            100                 105

<210> SEQ ID NO 175
<211> LENGTH: 108
<212> TYPE: PRT
<213> ORGANISM: Mus musculus

<400> SEQUENCE: 175

Asp Trp Val Ile Pro Pro Ile Ser Cys Pro Glu Asn Glu Lys Gly Glu
 1               5                  10                  15

Phe Pro Lys Asn Leu Val Gln Ile Lys Ser Asn Arg Asp Lys Glu Thr
            20                  25                  30

Lys Val Phe Tyr Ser Ile Thr Gly Gln Gly Ala Asp Lys Pro Pro Val
        35                  40                  45

Gly Val Phe Ile Ile Glu Arg Glu Thr Gly Trp Leu Lys Val Thr Gln
    50                  55                  60

Pro Leu Asp Arg Glu Ala Ile Ala Lys Tyr Ile Leu Tyr Ser His Ala
65                  70                  75                  80

Val Ser Ser Asn Gly Glu Ala Val Glu Asp Pro Met Glu Ile Val Ile
                85                  90                  95

Thr Val Thr Asp Gln Asn Asp Asn Arg Pro Glu Phe
            100                 105

<210> SEQ ID NO 176
<211> LENGTH: 108
<212> TYPE: PRT
<213> ORGANISM: Homo sapiens

<400> SEQUENCE: 176

Asp Trp Val Ile Pro Pro Ile Asn Val Pro Glu Asn Ser Arg Gly Pro
 1               5                  10                  15

Phe Pro Gln Gln Leu Val Arg Ile Arg Ser Asp Lys Asp Asn Asp Ile
            20                  25                  30

Pro Ile Arg Tyr Ser Ile Thr Gly Val Gly Ala Asp Gln Pro Pro Met
        35                  40                  45

Glu Val Phe Ser Ile Asp Ser Met Ser Gly Arg Met Tyr Val Thr Arg
    50                  55                  60

Pro Met Asp Arg Glu Glu His Ala Ser Tyr His Leu Arg Ala His Ala
65                  70                  75                  80

Val Asp Met Asn Gly Asn Lys Val Glu Asn Pro Ile Asp Leu Tyr Ile
                85                  90                  95

Tyr Val Ile Asp Met Asn Asp Asn Arg Pro Glu Phe
            100                 105

<210> SEQ ID NO 177
<211> LENGTH: 108
<212> TYPE: PRT
<213> ORGANISM: Mus musculus

<400> SEQUENCE: 177

Asp Trp Val Ile Pro Pro Ile Asn Val Pro Glu Asn Ser Arg Gly Pro
 1               5                  10                  15

Phe Pro Gln Gln Leu Val Arg Ile Arg Ser Asp Lys Asp Asn Asp Ile
            20                  25                  30

Pro Ile Arg Tyr Ser Ile Thr Gly Val Gly Ala Asp Gln Pro Pro Met
        35                  40                  45
```

```
Glu Val Phe Asn Ile Asp Ser Met Ser Gly Arg Met Tyr Val Thr Arg
    50                  55                  60

Pro Met Asp Arg Glu Glu Arg Ala Ser Tyr His Leu Arg Ala His Ala
65                  70                  75                  80

Val Asp Met Asn Gly Asn Lys Val Glu Asn Pro Ile Asp Leu Tyr Ile
                85                  90                  95

Tyr Val Ile Asp Met Asn Asp Asn Arg Pro Glu Phe
            100                 105

<210> SEQ ID NO 178
<211> LENGTH: 4
<212> TYPE: PRT
<213> ORGANISM: Artificial Sequence
<220> FEATURE:
<223> OTHER INFORMATION: calcium binding motif
<220> FEATURE:
<221> NAME/KEY: VARIANT
<222> LOCATION: 1,3
<223> OTHER INFORMATION: Xaa = any amino acid

<400> SEQUENCE: 178

Xaa Asp Xaa Glu
 1

<210> SEQ ID NO 179
<211> LENGTH: 4
<212> TYPE: PRT
<213> ORGANISM: Artificial Sequence
<220> FEATURE:
<223> OTHER INFORMATION: calcium binding motif

<400> SEQUENCE: 179

Asp Val Asn Glu
 1
```

US 7,456,153 B2

COMPOUNDS AND METHODS FOR MODULATING FUNCTIONS OF CLASSICAL CADHERINS

CROSS-REFERENCE TO RELATED APPLICATIONS

This application claims the benefit of U.S. Provisional Patent Application No. 60/426,194, filed Nov. 14, 2002, where this provisional application is incorporated herein by reference in its entirety.

BACKGROUND OF THE INVENTION

1. Field of the Invention

The present invention relates generally to methods for modulating classical cadherin-mediated functions, and more particularly to the use of modulating agents comprising a classical cadherin cell adhesion recognition sequence, or an antibody that specifically recognizes such a sequence, for inhibiting or enhancing functions mediated by classical cadherins such as cell adhesion.

2. Description of the Related Art

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions, spot and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins (also referred to herein as CADs) are a rapidly expanding family of calcium-dependent CAMs (Munro et al., *In: Cell Adhesion and Invasion in Cancer Metastasis*, P. Brodt, ed., pp. 17-34, RG Landes Co. (Austin Tex.), 1996). The classical cadherins (abbreviated classical CADs) are integral membrane glycoproteins that generally promote cell adhesion through homophilic interactions (a CAD on the surface of one cell binds to an identical CAD on the surface of another cell), although classical CADs also appear to be capable of forming heterotypic complexes with one another under certain circumstances and with lower affinity. Classical CADs have been shown to regulate epithelial, endothelial, neural and cancer cell adhesion, with different CADs expressed on different cell types. N (neural)-cadherin is predominantly expressed by neural cells, endothelial cells and a variety of cancer cell types. E (epithelial)-cadherin is predominantly expressed by epithelial cells. Other CADs are P (placental)-cadherin, which is found in human skin and R (retinal)-cadherin. A detailed discussion of the classical cadherins is provided in Munro S B et al., 1996, *In: Cell Adhesion and Invasion in Cancer Metastasis*, P. Brodt, ed., pp.17-34, RG Landes Company (Austin Tex.), 1996 and Rowlands T M, Symonds J M, Farookhi R and Blaschuk O W, 2000, Cadherins: Crucial regulators of structure and function in reproductive tissues, *Reviews in Reproduction* 5: 53-61.

The structures of the classical CADs are generally similar. As illustrated in FIG. 1, classical CADs are composed of five extracellular domains (EC1-EC5), a single hydrophobic domain (TM) that traverses the plasma membrane (PM), and two cytoplasmic domains (CP1 and CP2). The calcium binding motifs DXNDN (SEQ ID NO: 4), DXD and LDRE (SEQ ID NO: 2) are interspersed throughout the extracellular domains. Each of the extracellular domains comprises about 110 amino acid and has a folding topology that is similar to that of immunoglobulin variable-like domains (Overdulin et al., *Science* 267: 386-9). The first extracellular domain (EC1) contains the classical cadherin cell adhesion recognition (CAR) sequence HAV (His-Ala-Val), along with flanking sequences on either side of the classical CAR sequence that play a role in conferring specificity.

Although cell adhesion is required for certain normal physiological functions, there are situations in which the level of cell adhesion is undesirable. For example, many pathologies (such as autoimmune diseases, cancer and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cancer cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects.

Accordingly, there is a need in the art for compounds that modulate cell adhesion and improve drug delivery across permeability barriers without such disadvantages. The present invention fulfills this need and further provides other related advantages.

BRIEF SUMMARY OF THE INVENTION

The present invention provides cell adhesion modulating agents and methods for modulating CAD-mediated cell adhesion and is described herein with particular reference to the modulation of classical CAD-mediated cell adhesion. However such description is offered for purposes of illustration and not by way of limitation, as it will be understood by the skilled artisan that modulating agents described herein, while having particular utility in the modulation of classical CAD-mediated cell adhesion, may also find utility in the modulation of cell adhesion mediated by other classes of cell adhesion molecules, such as non-classical CADs. Accordingly, all such embodiments are considered within the scope of the instant disclosure.

In one aspect, the present invention provides a cell adhesion modulating agent capable of modulating classical CAD-mediated cell adhesion. Such an agent may comprise the Trp-containing CAR sequence (e.g., D/E-W-V-I/V/M-P/A-P (SEQ ID NO: 168)), a conservative (or nonconservative) analogue, a peptidomimetic of the Trp-containing CAR sequence, or an antibody or antigen-binding fragment thereof that specifically binds to the Trp-containing CAR sequence. In some embodiments, the modulating agent contains at least 3, 4, 5, 6, 7, 8, or 9 amino acids and/or at most 10-50 consecutive amino acid residues (including all integer values therebetween, such as 10, 11, 12, 13, 14, 15, 20, 25, 30, 35, 40, 45, and 50) of a naturally occurring CAD molecule (i.e., a CAD molecule that is present in nature and has not been intentionally modified by man in laboratory). In certain embodiments, the cell adhesion modulating agent comprises a Trp-containing CAR sequence present within a linear peptide or within the ring of a cyclic peptide. The linear peptide may contain at least 3, 4, 5, 6, 7, 8 or 9 amino acids and/or at most 10-100 amino acids including all integer values therebetween (e.g., 10, 15, 20, 25, 30, 40, 50, 60, 80 and 100). The size of the cyclic peptide ring in a modulating agent may be at least 3, 4, 5, 6, 7, 8 or 9 amino acids and/or at most 10-100 amino acids including all integer values therebetween (e.g., 10, 15, 20, 25, 30, 40, 50, 60, 80 and 100). Such a peptide may comprise an N-terminal or C-terminal modification, including N-acetylation.

The cell adhesion modulating agent described above may be linked to one or more of a heterologous compound such as a pharmaceutically active substance, a targeting agent, a detectable marker, or a solid support. In addition, the modulating agent may further comprise (a) a cell adhesion recognition (CAR) sequence other than a Trp-containing CAR sequence directly linked to, or separated by a linker from, the Trp-containing CAR sequence, (b) an antibody or antigen-binding fragments thereof that specifically binds to a CAR sequence other than the Trp-containing CAR sequence, or both (a) and (b).

In another aspect, the present invention provides a composition comprising a cell adhesion modulating agent as described above in combination with a physiologically acceptable carrier.

The present invention also provides a method for modulating cell adhesion that comprises contacting a cell (e.g., epithelial cells, endothelial cells, neural cells, tumor cells and lymphocytes) that expresses a cadherin (e.g., E-cadherin and N-cadherin) with the cell adhesion modulating agent as described above and thereby modulating cell adhesion. In certain embodiments, the modulating agent inhibits CAD-mediated cell adhesion. In other embodiments, it enhances CAD-mediated cell adhesion.

The present invention also provides a method for reducing the progression of a cancer in a mammal that comprises administering to a mammal having a cancer a modulating agent and thereby reducing the progression of the cancer in the mammal.

The present invention also provides a method for reducing unwanted cellular adhesion in a mammal that comprises administering to a mammal with unwanted cellular adhesion a modulating agent that inhibits CAD-mediated cell adhesion and thereby reducing unwanted cellular adhesion.

The present invention also provides a method for enhancing the delivery of a pharmaceutically active substance through the skin of a mammal that comprises contacting epithelial cells of a mammal with a pharmaceutical active substance and a modulating agent that inhibits CAD-mediated cell adhesion and thereby enhancing the delivery of the substance through the skin. The contacting step is performed under conditions and for a time sufficient to allow passage of the substance across the epithelial cells.

The present invention also provides a method for enhancing the delivery of a pharmaceutically active substance to a tumor in a mammal that comprises contacting the tumor with a pharmaceutically active substance and a modulating agent that inhibits CAD mediated cell adhesion and thereby enhancing the delivery of the substance to the tumor. The contacting step is performed under conditions and for a time sufficient to allow passage of the substance into the cells of the tumor.

The present invention also provides a method for inhibiting cancer metastasis comprising administrating to a mammal having a cancer with a modulating agent, thereby inhibiting metastasis of the cancer.

The present invention also provides a method for inducing apoptosis in a CAD-expressing cell that comprises contacting a CAD-expressing cell with a modulating agent that inhibits CAD-mediated cell adhesion, thereby inducing apoptosis in the cell.

The present invention also provides a method for inhibiting angiogenesis in a mammal that comprises administering to a mammal a modulating agent that inhibits CAD-mediated cell adhesion, thereby inhibiting angiogenesis in the mammal.

The present invention also provides a method for enhancing the delivery of a pharmaceutically active substance to the central nervous system of a mammal, comprising administering to a mammal a modulating agent that inhibits CAD mediated cell adhesion, thereby enhancing the delivery of a pharmaceutically active substance.

The present invention also provides a method for ameliorating a demyelinating neurological disease in a mammal, comprising administering to a mammal with a demyelinating neurological disease a modulating agent that inhibits CAD mediated cell adhesion, thereby ameliorating the demyelinating neurological disease.

The present invention also provides a method for modulating the immune system of a mammal, comprising administering to a mammal a modulating agent that inhibit CAD mediated cell adhesion, thereby modulating the immune system of the mammal.

The present invention also provides a method for preventing pregnancy in a mammal, comprising administering to a mammal a modulating agent that inhibit CAD mediated cell adhesion, thereby preventing pregnancy in the mammal.

The present invention also provides a method for increasing vasopermeability in a mammal, comprising administering to a mammal a modulating agent that inhibits CAD mediated cell adhesion, thereby increasing vasopermeability in the mammal.

The present invention also provides a method for inhibiting synaptic stability in a mammal that comprises administering to a mammal a modulating agent that inhibits CAD mediated cell adhesion, thereby inhibiting synaptic stability in the mammal.

The present invention also provides a method for facilitating blood sampling in a mammal that comprises contacting epithelial cells of a mammal with a cell adhesion modulating agent that inhibits CAD mediated cell adhesion, thereby facilitating blood sampling in the mammal. The contacting step is performed under conditions and for a time sufficient to allow passage of one or more blood components across the epithelial cells.

The present invention also provides a method for facilitating migration of an N-cadherin expressing cell on astrocytes that comprises contacting an N-caderin expressing cell with a cell adhesion modulating agent that inhibits CAD mediated cell adhesion and one or more astrocytes, thereby facilitating migration of the N-cadherin expressing cell on the astrocytes.

The present invention also provides a method for stimulating blood vessel regression that comprises administering to a mammal a cell adhesion modulating agent that inhibits CAD mediated cell adhesion, thereby stimulating blood vessel regression.

The present invention also provides a method for reducing aggregation of cultured stem cells that comprises contacting cultured stem cells with a cell adhesion modulating agent that inhibits CAD mediated cell adhesion, thereby reducing aggregation of stem cells.

The present invention also provides a method for increasing blood flow to a tumor in a mammal that comprises administering to a mammal a cell adhesion modulating agent that inhibits CAD mediated endothelial cell adhesion, thereby increasing blood flow to a tumor in the mammal.

The present invention also provides a method of disrupting neovasculature in a mammal that comprises administering to a mammal a cell adhesion modulating agent that inhibits CAD mediated cell adhesion, thereby disrupting neovasculature.

The present invention also provides a method for inhibiting endometriosis in a mammal that comprises administering to a mammal a cell adhesion modulating agent that inhibits CAD mediated cell adhesion, thereby inhibiting endometriosis.

The present invention also provides a method for enhancing inhaled compound delivery in a mammal that comprising contacting lung epithelial cells of a mammal with a cell adhesion modulating agent that inhibits CAD mediated cell adhesion, thereby enhancing inhaled compound delivery.

The present invention also provides a method for facilitating wound healing in a mammal that comprises contacting a wound in a mammal with a cell adhesion modulating agent that enhances CAD-mediated cell adhesion, thereby facilitating wound healing.

The present invention also provides a method for enhancing adhesion of a foreign tissue implanted within a mammal that comprises contacting a site of implantation of a foreign tissue in a mammal with a cell adhesion modulating agent that enhances CAD-mediated cell adhesion, thereby enhancing adhesion of the foreign tissue.

The present invention also provides a method for enhancing and/or directing neurite outgrowth that comprises contacting a neuron with a cell adhesion modulating agent that enhances CAD-mediated cell adhesion, thereby enhancing and directing neurite outgrowth, wherein the modulating agent enhances CAD-mediated cell adhesion.

The present invention also provides a method of ameliorating a spinal cord injury in a mammal that comprises administering to a mammal having a spinal cord injury a cell adhesion modulating agent that enhances CAD-mediated cell adhesion, thereby ameliorating the spinal cord injury.

In other embodiments of the invention, there are provided methods for modulating the behavior, e.g., cell adhesion, proliferation, migration and/or survival, of vascular smooth muscle cells (VSMC) or pericytes, comprising contacting a CAD expressing VSMC or pericyte cell with, or administering to a mammal, a cell adhesion modulating agent as described herein.

In a related embodiment, there are provided methods for regulating the overgrowth and/or migration of VSMCs or pericytes, comprising contacting a CAD expressing cell with, or administering to a mammal, a cell adhesion modulating agent as described herein, wherein the modulating agent is preferably an inhibitor of CAD-mediated cell adhesion. Particularly illustrative uses according to this embodiment relate to preventing the formation or advance of restenosis, vein bypass graft failure, allograft vasculopathy, dialysis graft failure, thin cap fibroatheroma, and other vessel stenoses. Related embodiments include the treatment of essential and secondary hypertension, atheroma, arteriosclerosis, or other indications in which endothelial injury or trauma has occurred.

In another related embodiment, there are provided methods for maintaining vessel luminal area following vascular trauma, comprising contacting a CAD expressing cell with, or administering to a mammal, a cell adhesion modulating agent as provided herein, wherein the modulating agent is preferably an inhibitor of CAD-mediated cell adhesion.

In another related embodiment, there are provided methods for treating a traumatized vessel, comprising contacting a CAD expressing cell with, or administering to a mammal, a cell adhesion modulating agent as provided herein, wherein the modulating agent is preferably an inhibitor of CAD-mediated cell adhesion. Particularly illustrative uses according to this embodiment include the treatment of trauma that may occur during stent placement, organ transplant, vein bypass, angioplasty, dialysis graft placement, and the like.

In still other embodiments, one or more modulating agents are provided as an active component of a medical device (e.g. a balloon, stent, shunt, catheter, stent graft, vascular graft, vascular patch, filter, adventitial wrap, intraluminal paving system, cerebral stent, cerebral aneurysm filter coil, myocardical plug, pacemaker lead, dialysis access graft, heart valve, etc.). For example, the modulating agents of the invention may be linked to, coated on, or dispersed within essentially any medical device using known techniques in order to provide or deliver modulating agent in a desired physiological and/or anatomical context.

In these and other embodiments, the modulating agents of the present invention may be delivered to a CAD expressing cell, or a subject, by essentially any delivery approach suitable to a given indication and compatible with the delivery of modulating agents provided herein. In one embodiment, administration of a modulating agent provided herein is accomplished via a catheter. In another embodiment, administration of an agent is accomplished using an infusion needle.

There are also provided according to the invention methods for enhancing the survival of neurons and/or suppressing neural injury, for example as a result of stroke or other type of brain ischemia, comprising contacting a CAD expressing neural cell with, or administering to a mammal, a cell adhesion modulating agent as described above, wherein the modulating agent preferably is one that enhances cadherin-mediated cell adhesion.

Related embodiments of the invention are provided for treatment for stroke recovery, reversing or establishing plateau in dementias, treatment for trauma to the CNS, spine and peripheral nerves, as well as treatment of neuropathies.

In another embodiment, there are provided methods for enhancing neurite outgrowth comprising contacting a CAD expressing neural cell with, or administering to a mammal, a cell adhesion modulating agent as described above, wherein the modulating agent is preferably one that enhances CAD-mediated cell adhesion.

In another embodiment, there are provided methods for facilitating the removal of hair follicles from skin, e.g., viable or intact hair follicles, comprising contacting a CAD expressing cell with, or administering to a mammal, a cell adhesion modulating agent of the invention. Certain aspects of this embodiment find particular utility in removing unwanted hair follicles and/or in the re-transplantation of hair follicles at a site of the body different from that in which they originated.

In other embodiments, methods are provided for stimulating angiogenesis comprising contacting a CAD expressing cell with, or administering to a mammal, a modulating agent provided herein, wherein the modulating agent enhances cadherin-mediated cell adhesion.

In still other embodiments, there are provided methods for modulating endothelial cell behavior, e.g., endothelial cell migration, proliferation, survival and/or adhesion comprising contacting a CAD expressing cell with, or administering to a mammal, a modulating agent provided herein.

Within further embodiments, methods are provided for modulating endothelial cell adhesion, comprising contacting a CAD-expressing endothelial cell with, or administering to a mammal, a cell adhesion modulating agent as described herein. In certain preferred embodiments, the modulating agent inhibits N-cadherin mediated cell adhesion, resulting in the reduction of unwanted endothelial cell adhesion in the mammal.

In another embodiment, method are provided for modulating adipogenesis (a process dependent on angiogenesis) comprising contacting a CAD-expressing cell with, or administering to a mammal, a modulating agent described herein, wherein the modulating agent is preferably one that inhibits CAD-mediated cell adhesion.

In another embodiment, methods are provided for modulating tumor blood flow, comprising contacting a cadherin-expressing endothelial cell with, or administering to a mammal, a modulating agent described herein. Depending on the application, in certain embodiments, the modulating agent is preferably one that enhances CAD-mediated cell adhesion while in others the modulating agent is preferably one that inhibits CAD-mediated cell adhesion.

In still further embodiments, methods are provided for the treatment of disease conditions that are dependent on angiogenesis and neovascularization. Disruption of neovasculature is therapeutic for conditions in which the presence of newly formed blood vessels is related to the underlying disorder, its symptoms or its complications. For example, disorders that may be treated include, but are not limited to, benign prostatic hyperplasia, diabetic retinopathy, vascular restenosis, arteriovenous malformations, meningioma, hemangioma, neovascular glaucoma, psoriasis, angiofiboma, arthritis, atherosclerotic plaques, corneal graft neovascularization, hemophilic joints, hypertrophic scars, hemorrhagic telangiectasia, pyogenic granuloma, retrolental fibroplasias, scleroderma trachoma, vascular adhesions, synovitis, dermatitis, endometriosis, macular degeneration and exudative macular degeneration. These methods comprise contacting an N-cadherin-expressing cell with, or administering to a mammal, a modulating agent described herein, wherein the modulating agent preferably is one that inhibits CAD-mediated cell adhesion.

In other embodiments, methods are provided for modulating FGF receptor activity. In one such embodiment, modulating agents that preferably inhibit CAD-mediated cell adhesion are used for preventing the interaction between FGF receptor monomers. In another embodiment, modulating agents that enhance N-cadherin cell adhesion are preferably employed for their ability to promote the interaction between FGF receptor monomers.

In yet another embodiment, methods are provided for modulating tumor permeability barriers to drugs, such as chemotherapeutic agents, comprising contacting a CAD-expressing cell with, or administering to a mammal, a modulating agent described herein.

In another embodiment, methods are provided for the modulation of bone adhesion, for example in the context of bone grafts, comprising contacting a CAD-expressing cell with, or administering to a mammal, a modulating agent described herein, preferably a modulating agent that enhances CAD-mediated cell adhesion. Modulating agents according to the invention may be effective, for example, in promoting bone adhesion to grafts.

In one aspect, the present invention provides a kit for enhancing transdermal delivery of a pharmaceutically active substance, comprising: a skin patch and a cell adhesion modulating agent.

In another aspect, the present invention provides a method for screening a candidate compound for the ability to modulate classical CAD-mediated cell adhesion that comprises comparing a three-dimensional structure of a candidate compound to a three-dimensional structure of a Trp-containing CAR sequence (e.g., D/E-W-V-I/V/M-P/A-P (SEQ ID NO: 168)), therefrom evaluating the ability of the candidate compound to modulate classical CAD-mediated cell adhesion. For such a method, the similarity between the structure of the candidate compound and the structure of the peptide is indicative of the ability of the candidate compound to modulate classical CAD-mediated cell adhesion.

The present invention also provides a method for identifying a compound that modulates classical CAD-mediated cell adhesion that comprises: (a) determining a level of similarity between a three-dimensional structure of a candidate compound and a three-dimensional structure of a Trp-containing CAR sequence; and (b) identifying an alteration in the structure of the candidate compound that results in a three-dimensional structure with an increased similarity to the three-dimensional structure of the peptide; therefrom identifying a compound that has the ability to modulate classical CAD-mediated cell adhesion.

The present invention also provides a method for evaluating a peptidomimetic for the ability to modulate classical CAD-mediated cell adhesion that comprises (a) culturing neurons on a monolayer of cells that express N-cadherin in the presence and absence of a peptidomimetic, under conditions and for a time sufficient to allow neurite outgrowth, wherein the peptidomimetic has a three-dimensional structure that is substantially similar to a three-dimensional structure of a Trp-containing CAR sequence; (b) determining a mean neurite length for said neurons; and (c) comparing the mean neurite length for neurons cultured in the presence of peptidomimetic to the neurite length for neurons cultured in the absence of the peptidomimetic, therefrom determining whether the peptidomimetic modulates classical CAD-mediated cell adhesion.

The present invention also provides a method for evaluating a peptidomimetic for the ability to modulate classical CAD-mediated cell adhesion that comprises: (a) culturing cells that express a classical CAD in the presence and absence of a peptidomimetic, under conditions and for a time sufficient to allow cell adhesion, wherein the peptidomimetic has a three-dimensional structure that is substantially similar to a three-dimensional structure of a Trp-containing CAR squence; and (b) visually evaluating the extent of cell adhesion among said cells, and therefrom identifying a peptidomimetic capable of modulating cell adhesion.

The present invention also provides a method for evaluating a peptidomimetic for the ability to modulate classical CAD-mediated cell adhesion that comprises: (a) culturing NRK cells in the presence and absence of a peptidomimetic, under conditions and for a time sufficient to allow cell adhesion, wherein the peptidomimetic has a three-dimensional structure that is substantially similar to a three-dimensional structure of a Trp-containing CAR sequence; and (b) comparing the level of cell surface E-cadherin for cells cultured in the presence of the peptidomimetic to the level for cells cultured in the absence of the peptidomimetic, and therefrom determining whether the peptidomimetic modulates cell adhesion.

The present invention also provides a method for evaluating a peptidomimetic for the ability to modulate classical CAD-mediated cell adhesion that comprises: (a) contacting an epithelial surface of skin with a test marker in the presence and absence of a peptidomimetic, wherein the peptidomimetic has a three-dimensional structure that is substantially similar to a three-dimensional structure of a Trp-containg CAR sequence; and (b) comparing the amount of test marker that passes through said skin in the presence of the peptidomimetic to the amount that passes through skin in the absence of the peptidomimetic, therefrom determining whether the peptidomimetic modulates cell adhesion.

The present invention also provides a method for evaluating the ability of a peptidomimetic to modulate classical CAD-mediated cell adhesion that comprises: (a) contacting a blood vessel with a peptidomimetic, wherein the peptidomimetic has a three-dimensional structure that is substantially similar to a three-dimensional structure of a peptide having a Trp-containing CAR sequence; and (b) comparing the extent of angiogenesis of the blood vessel to a predetermined extent of angiogenesis observed for a blood vessel in the absence of the peptidomimetic, therefrom determining whether the peptidomimetic modulates cell adhesion.

The present invention also provides cell adhesion modulating agents that are peptidomimetics of Trp-containing CAR sequences (e.g., Compound I).

The present invention further provides a process for manufacturing a compound that modulates cell adhesion that comprises the steps of performing the methods for identifying a compound that modulates classical CAD-mediated cell adhesion as described above and producing the identified compound.

In a related aspect, the present invention provides a process for manufacturing a peptidomimetic that modulates cell adhesion comprising the steps of performing any one of the methods for evaluating the ability of a peptidomimetic to modulating classical CAD-mediated cell adhesion as described above; and producing the peptidomimetic if the peptidomemitic has the ability to modulate cell adhesion.

It is appreciated that to successfully perform various methods of the present invention, an effective amount of the modulating agents are used under conditions and for a time sufficient to achieve the desired results. Determining the effective amount, the appropriate conditions and the sufficient time period may either be within the ordinary skill in the art, and/or accomplished in view of the teachings provided herein.

BRIEF DESCRIPTION OF THE DRAWINGS

FIG. 2 provides the amino acid sequences of mammalian classical cadherin EC1 domains: human N-cadherin (SEQ ID NO: 169), mouse N-cadherin (SEQ ID NO; 170), cow N-cadherin (SEQ ID NO; 171), human E-cadherin (SEQ ID NO: 172), mouse E-cadherin, (SEQ ID NO: 173) human P-cadherin, (SEQ ID NO: 174) mouse P-cadherin (SEQ ID NO: 175), human R-cadherin (SEQ ID NO: 176) and mouse R-cadherin (SEQ ID NO: 177).

DETAILED DESCRIPTION OF THE INVENTION

Figure 1:
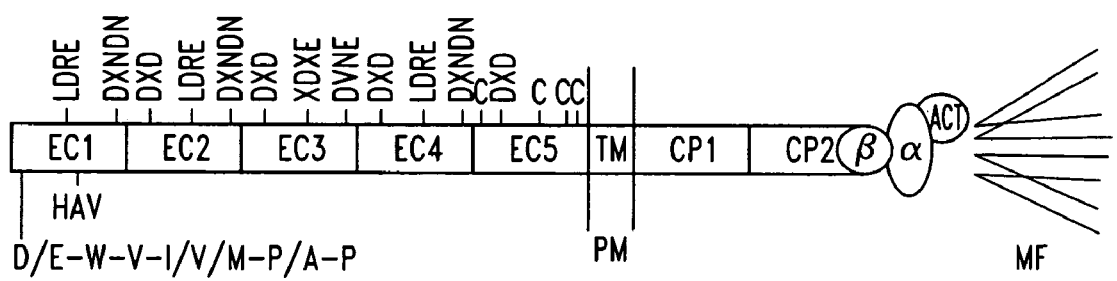
FIG. 1 is a diagram depicting the structure of classical CADs. The five extracellular domains are designated EC1-EC5, the hydrophobic domain that transverses the plasma membrane (PM) is represented by TM, and the two cytoplasmic domains are represented by CP1 and CP2. The calcium binding motifs are shown by DXNDN (SEQ ID NO: 4), DXD, XDXE (SEQ ID NO: 178), DVNE (SEQ ID NO: 179) and LDRE (SEQ ID NO: 2). The classical CAR sequence (HAV) and a Trp-containing CAR sequence (D/E-W-V-I/V/M-P/A-P, SEQ ID NO: 168), is shown within EC1. Cytoplasmic proteins β-catenin (β), α-catenin (α) and α-actinin (ACT), which mediate the interaction between CADs and microfilaments (MF) are also shown.
Figure 3:
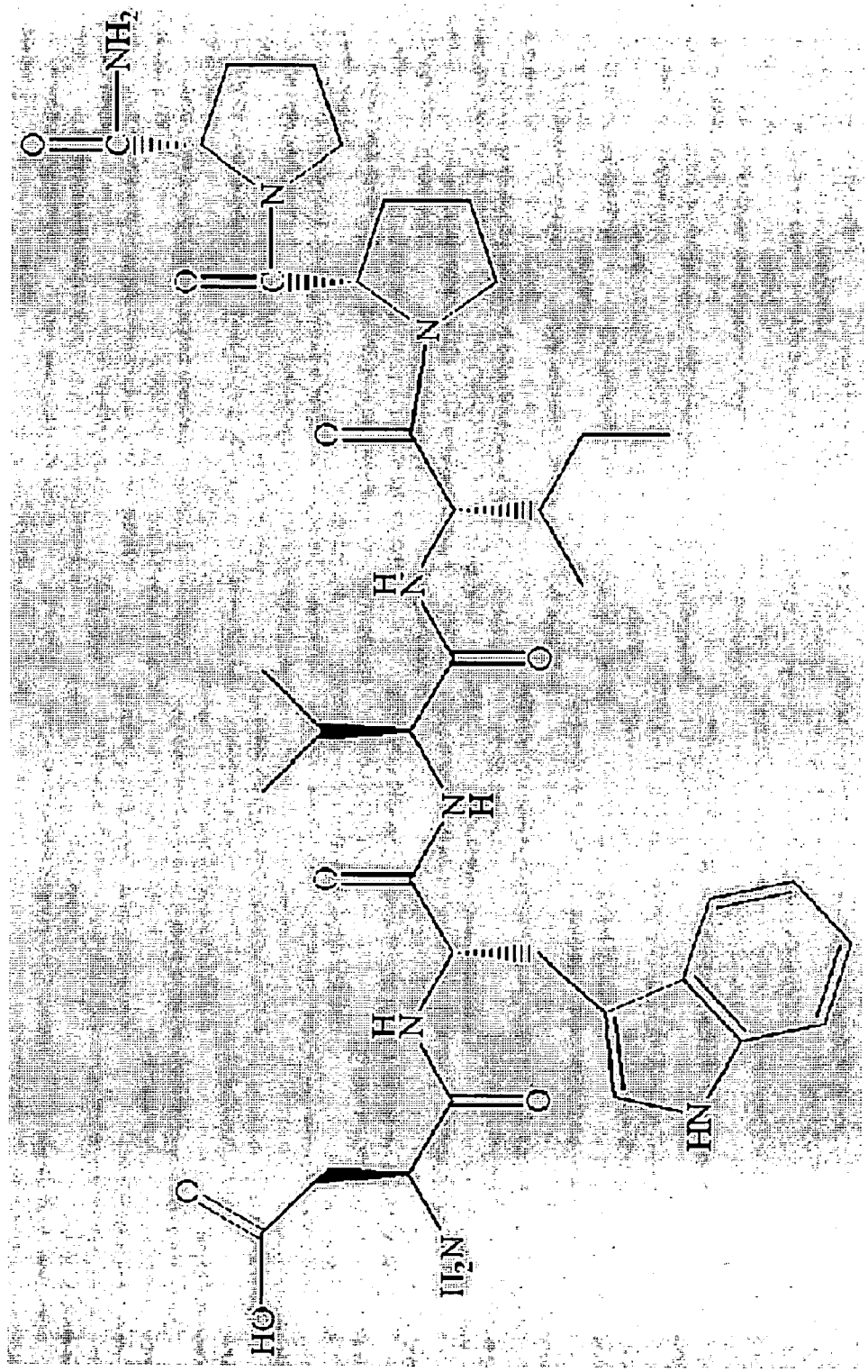
FIG. 3 provides the structure of an exemplary cell adhesion modulating agent H-DWVIPP-NH$_2$ (SEQ ID NO: 3).
Figure 4:
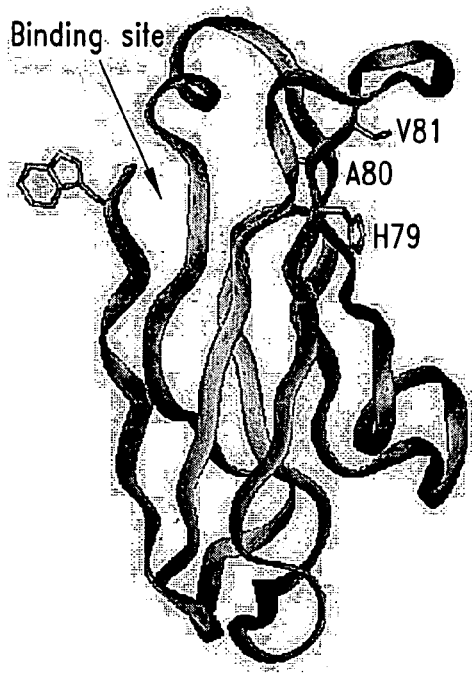
FIG. 4 shows schematic representation of a 3-D structure of the N-terminal domain (EC1) of N-cadherin protein (PDB code: 1NCG).

As noted above, the present invention provides methods for modulating classical cadherin-mediated processes, such as cell adhesion. The present invention is based upon the identification of a previously unknown cell adhesion recognition (CAR) sequence in classical cadherins.

In general, to modulate a classical cadherin-mediated function, a cell that expresses a classical cadherin is contacted with a modulating agent either in vivo or in vitro. A modulating agent may comprise one or more Trp-containing CAR sequences or conservative analogues or peptidomimetics (used interchangeably with "mimetics") of such sequences, with or without one or more additional CAR sequences (which may be derived from classical cadherins or from other adhesion molecules), as described below. Trp-containing CAR sequences may be present within a linear or cyclic peptide. Alternatively, or in addition, a modulating agent may comprise an antibody or antigen-binding fragment thereof that specifically binds a Trp-containing CAR sequence.

Certain methods provided herein employ modulating agents for inhibiting (lessening, reducing, or disrupting) or enhancing cadherin-mediated cell adhesion. Inhibition of cell adhesion may generally be used, for example, to treat diseases or other conditions characterized by undesirable cell adhesion or to facilitate drug delivery either through the skin, or to a specific tissue or tumor. Within other aspects, the methods provided herein may be used to enhance cell adhesion (e.g., to supplement or replace stitches or to facilitate wound healing). Within still further aspects, methods are provided for enhancing and/or directing neurite outgrowth.

Cell Adhesion Modulating Agents

As noted above, the term "cell adhesion modulating agent," as used herein, generally refers to a compound that (1) comprises (a) a Trp-containing CAR sequence, (b) a conservative analogue of the above sequence, (c) a peptidomimetic of the above sequence, or (d) an antibody or antigen-binding fragment thereof that specifically binds to the above sequence.

A modulating agent may comprise entirely one or more of the above elements, or may additionally comprise further peptide and/or non-peptide regions. Additional peptide regions may be derived from a classical cadherin (preferably an extracellular domain that comprises a Trp-containing CAR sequence) and/or may be heterologous.

A modulating agent is further capable of modulating a function (such as cell adhesion) mediated by a classical cadherin. Such activity may generally be assessed using, for example, representative assays provided herein. Certain modulating agents inhibit (reduce) an interaction between classical cadherin molecules and/or between a classical cadherin and a different adhesion molecule. Alternatively, to enhance adhesion of classical cadherin-expressing cells, a modulating agent may comprise an antibody or antigen-binding fragment thereof and/or multiple peptides or mimetics linked to a support material. Such modulating agents may function as a biological glue to bind classical cadherin-expressing cells, and should result in a detectable enhancement of cell adhesion.

A "Trp-containing CAR sequence" of a classical cadherin is an amino acid sequence that comprises a Trp residue, is present within the extracellular domain of a naturally occurring classical cadherin, and is capable of detectably modulating a classical cadherin-mediated function, such as cell adhesion, as described herein. In other words, contacting a classical cadherin-expressing cell with a peptide comprising a Trp-containing CAR sequence results in a detectable change in a classical cadherin-mediated function using at least one of the representative assays provided herein. Trp-containing CAR sequences are generally recognized in vivo by a classical cadherin or other adhesion molecule (i.e., a molecule that mediates cell adhesion via a receptor on the cell surface), and are necessary for maximal heterophilic and/or homophilic interaction. Trp-containing CAR sequences may be of any length, but generally comprise at least 3, 4, 5, 6, 7, 8, or 9 amino acid residues and/or at most 10-50 amino acid residues (including all the integer values therebetween).

It has been found, within the context of the present invention, that certain classical cadherin Trp-containing CAR sequences share the consensus sequence:

(SEQ ID NO: 1)
Asp/Glu-Trp-Val-Ile/Val/Met-Pro/Ala-Pro

Within the above consensus sequence, "Asp/Glu" is an amino acid that is either Asp or Glu, "Ile/Val/Met" is an amino acid that is Ile, Val or Met, and "Pro/Ala" is either Pro or Ala. In addition, a Trp-containing CAR sequence is also able to modulate cell adhesion.

The present invention further contemplates classical cadherin Trp-containing CAR sequences from organisms other than human. Such Trp-containing CAR sequences may be identified based upon sequence similarity to the sequences provided herein, and the ability to modulate a classical cadherin-mediated function, such as cell adhesion, may be confirmed as described herein.

It will be apparent that certain of the peptide sequences provided above may modulate a function mediated by multiple classical cadherins. In general, peptides comprising a greater number of consecutive residues derived from a particular classical cadherin have a greater specificity for that cadherin. In addition, further flanking sequences may be included to enhance specificity. Such flanking sequences may be identified based on the sequences provided in FIG. 2, or based on published sequences. To achieve specificity (i.e., modulation of a particular classical cadherin function that is enhanced relative to the modulation of a function mediated by a different cadherin), the addition of 2 to 5 flanking residues is generally sufficient. Specificity may be evaluated using assays for the ability to inhibit functions mediated by particular cadherins, as described herein.

Modulating agents, or peptide portions thereof, may generally comprise from about 3 to about 100 amino acid residues. In certain embodiments, the modulating agents contain at least 3, 4, 5, 6, 7, 8, or 9 amino acids and/or at most 10-100 amino acid residues, including all the integer values therebetween. In some embodiments where non-peptide linkers are employed, each Trp-containing CAR sequence or its conservative analogue thereof may be present within a peptide that contains at least 3, 4, 5, 6, 7, 8, or 9 amino acids an/or at most 10-50 amino acids, including all integer values therebetween, e.g., 10, 15, 20, 25, 30, 35, 40, 45, or 50 amino acid residues. In certain preferred embodiments, modulating agents or peptide portions thereof contain at least 3, 4, 5, 6, 7, 8, or 9 amino acids and/or at most 10-50 amino acids including all integer values therebetween, e.g., 10, 15, 20, 25, 30, 35, 40, 45, and 50 consecutive residues from a naturally occurring (used interchangeably with "native") cadherin molecule.

As noted above, modulating agents as described herein may comprise an analogue or mimetic of a classical cadherin Trp-containing CAR sequence. An analogue generally retains at least 50% identity to a native classical cadherin Trp-containing CAR sequence and at least 50% of a classical cadherin-mediated function as described herein. In this context, the percent identity of two amino acid sequences or of two nucleic acids is determined using BLAST programs of Altschul et al. (*J. Mol. Biol.* 215: 403-10, 1990) with their default parameters. These programs implement the algorithm of Karlin and Altschul (*Proc. Natl. Acad. Sci. USA* 87:2264-8, 1990) modified as in Karlin and Altschul (*Proc. Natl. Acad. Sci. USA* 90:5873-7, 1993). BLAST programs are available, for example, at the web site http://www.ncbi.nlm.nih.gov.

The analogues of the present invention preferably contain at least three, four or five consecutive residues of a classical cadherin Trp-containing CAR sequence. An analogue may contain any of a variety of amino acid substitutions, additions, deletions and/or modifications (e.g., side chain modifications).

A "conservative analogue" of a Trp-containing CAR sequence is a Trp-containing CAR sequence with one, two, three or more conservative amino acid substitutions and without any non-conservative amino acid substitutions.

A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Exemplary Trp-containing CAR sequences or conservative analogues thereof include, but are not limited to, DWV, DWVI (SEQ ID NO: 5), DWVV (SEQ ID NO: 6), DWVM (SEQ ID NO: 7), DWVIP (SEQ ID NO: 8), DWVIA (SEQ ID NO: 9), DWVVP (SEQ ID NO: 10), DWVVPP (SEQ ID NO: 11), DWVVAP (SEQ ID NO: 12), DWVMPP (SEQ ID NO: 13), DWVMAP (SEQ ID NO: 14), EWV, EWVI (SEQ ID NO: 15), EWVV (SEQ ID NO: 16), EWVM (SEQ ID NO: 17), EWVIP (SEQ ID NO: 18), EWVIA (SEQ ID NO: 19), EWVVP (SEQ ID NO: 20), EWVVPP (SEQ ID NO: 21), EWVVAP (SEQ ID NO: 22), EWVMPP (SEQ ID NO: 23), EWVMAP (SEQ ID NO: 24), WVI, WVIP (SEQ ID NO: 25), WVIA (SEQ ID NO: 26), WVV, WVVP (SEQ ID NO: 27), WVVA (SEQ ID NO: 28), WVM, WVMP (SEQ ID NO: 29), WVMA (SEQ ID NO: 30), WVIPP (SEQ ID NO: 31), WVIAP (SEQ ID NO: 32), WVVPP (SEQ ID NO: 33), WVVAP (SEQ ID NO: 34), WVMPP (SEQ ID NO: 35), WVMAP (SEQ ID NO: 36), DWI, DWII (SEQ ID NO: 37), DWIV (SEQ ID NO: 38), DWIM (SEQ ID NO: 39), DWIIP (SEQ ID NO: 40), DWIIA (SEQ ID NO: 41), DWIVP (SEQ ID NO: 42), DWIVPP (SEQ ID NO: 43), DWIVAP (SEQ ID NO: 44), DWIMPP (SEQ ID NO: 45), DWIMAP (SEQ ID NO: 46), EWI, EWII (SEQ ID NO: 47), EWIV (SEQ ID NO: 48), EWIM (SEQ ID NO: 49), EWIIP (SEQ ID NO: 50), EWIIA (SEQ ID NO: 51), EWIVP (SEQ ID NO: 52), EWIVPP (SEQ ID NO: 53), EWIVAP (SEQ ID NO: 54), EWIMPP (SEQ ID NO: 55), EWIMAP (SEQ ID NO: 56), WII, WIIP (SEQ ID NO: 57), WIIA (SEQ ID NO: 58), WIV, WIVP (SEQ ID NO: 59), WIVA (SEQ ID NO: 60), WIM, WIMP (SEQ ID NO: 61), WIMA (SEQ ID NO: 62), WIIPP (SEQ ID NO: 63), WIIAP (SEQ ID NO: 64), WIVPP (SEQ ID NO: 65), WIVAP (SEQ ID NO: 66), WIMPP (SEQ ID NO: 67), WIMAP (SEQ ID NO: 68), DWL, DWLI (SEQ ID NO: 69), DWLV (SEQ ID NO: 70), DWLM (SEQ ID NO: 71), DWLIP (SEQ ID NO: 72), DWLIA (SEQ ID NO: 73), DWLVP (SEQ ID NO: 74), DWLVPP (SEQ ID NO: 75), DWLVAP (SEQ ID NO: 76), DWLMPP (SEQ ID NO: 77), DWLMAP (SEQ ID NO: 78), EWL, EWLI (SEQ ID NO: 79), EWLV (SEQ ID NO: 80), EWLM (SEQ ID NO: 81), EWLIP (SEQ ID NO: 82), EWLIA (SEQ ID NO: 83), EWLVP (SEQ ID NO: 84), EWLVPP (SEQ ID NO: 85), EWLVAP (SEQ ID NO: 86), EWLMPP (SEQ ID NO: 87), EWLMAP (SEQ ID NO: 88), WLI, WLIP (SEQ ID NO: 89), WLIA (SEQ ID NO: 90), WLV, WLVP (SEQ ID NO: 91), WLVA (SEQ ID NO: 92), WLM, WLMP (SEQ ID NO: 93), WLMA (SEQ ID NO: 94), WLIPP (SEQ ID NO: 95), WLIAP (SEQ ID NO: 96), WLVPP (SEQ ID NO: 97), WLVAP (SEQ ID NO: 98), WLMPP (SEQ ID NO: 99), WLMAP (SEQ ID NO: 100), DWVL (SEQ ID NO: 101), DWIL (SEQ ID NO: 102), DWLL (SEQ ID NO: 103), EWVL (SEQ ID NO: 104), EWIL (SEQ ID NO: 105), EWLL (SEQ ID NO: 106), DWVLP (SEQ ID NO: 107), DWILP (SEQ ID NO: 108), DWLLP (SEQ ID NO: 109), EWVLP (SEQ ID NO: 110), EWILP (SEQ ID NO: 111), EWLLP (SEQ ID NO: 112), DWVLA (SEQ ID NO: 113), DWILA (SEQ ID NO: 114), DWLLA (SEQ ID NO: 115), EWVLA (SEQ ID NO: 116), EWILA (SEQ ID NO: 117), EWLLA (SEQ ID NO: 118), DWVLPP (SEQ ID NO: 119), DWILPP (SEQ ID NO: 120), DWLLPP (SEQ ID NO: 121), EWVLPP (SEQ ID NO: 122), EWILPP (SEQ ID NO: 123), EWLLPP (SEQ ID NO: 124), DWVLAP (SEQ ID NO: 125), DWILAP (SEQ ID NO: 126), DWLLAP (SEQ ID NO: 127), EWVLAP (SEQ ID NO: 128), EWILAP (SEQ ID NO: 129), EWLLAP (SEQ ID NO: 130), WVL, WIL, WLL, WVLP (SEQ ID NO: 131), WILP (SEQ ID NO: 132), WLLP (SEQ ID NO: 133), WVLA (SEQ ID NO: 134), WILA (SEQ ID NO: 135), WLLA (SEQ ID NO: 136), WVLPP (SEQ ID NO: 137), WILPP (SEQ ID NO: 138), WLLPP (SEQ ID NO: 139), WVLAP (SEQ ID NO: 140), WILAP (SEQ ID NO: 141), and WLLAP (SEQ ID NO: 142).

A "non-conservative analogue" of a Trp-containing CAR sequence is a Trp-containing CAR sequence with at least one amino acid substitution (i.e., non-conservative amino acid substitution) other than a conservative amino acid substitution as is defined above, at least one amino acid deletion, and/or at least one amino acid insertion.

A "peptidomimetic" is a compound in which at least a portion of a Trp-containing CAR sequence is replaced with a non-peptide structure, but the three-dimensional structure of the Trp-containing CAR sequence remains substantially the same as that of the Trp-containing CAR sequence. In other words, one, two, three, four, five or six amino acid residues within the Trp-containing CAR sequence may be replaced by one or more chemical structures so that at least one peptide bond in the Trp-containing CAR sequence is eliminated. A peptidomimetic of the present invention is also capable of modulating a function mediated by a classical cadherin.

Modulating agents, or peptide portions thereof, may be linear or cyclic peptides. In certain embodiments, the linear or cyclic peptides may contain at least one terminal amino acid residue that is modified (e.g., the N-terminal amino group is modified by, for example, acetylation or alkoxybenzylation and/or an amide or ester is formed at the C-terminus).

The term "cyclic peptide," as used herein, refers to a peptide or salt thereof that comprises (1) an intramolecular covalent bond between two non-adjacent residues and (2) at least one Trp-containing CAR sequence or a conservative analogue thereof present within the peptide ring. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. As described below, in addition to one or more Trp-containing CAR sequences or a conservative analogue thereof, a modulating agent may comprise additional CAR sequence(s), which may or may not be cadherin CAR sequences, and/or antibodies or fragments thereof that specifically recognize a CAR sequence. These additional CAR sequence(s) may or may not be present within a cyclic peptide portion of a modulating agent. Antibodies and antigen-binding fragments thereof are typically present in a non-cyclic portion of a modulating agent.

The size of a cyclic peptide ring generally ranges from 3, 4, 5, 6, 7, or 8 to 10, 11, 12, 13, 14, 15, 16, 17, 18, 19 or 20 residues, preferably from 5 or 6 to 10 or 15 residues. Additional residue(s) may be present on the N-terminal and/or C-terminal side of a Trp-containing CAR sequence or a conservative analogue thereof, and may be derived from sequences that flank a native Trp-containing CAR sequence, with or without amino acid substitutions and/or other modifications. Flanking sequences at C-terminal side for endogenous N-, E-, P- and R-cadherin are shown in FIG. 2. Database accession numbers for representative naturally occurring cadherins are as follows: human N-cadherin M34064, mouse N-cadherin M31131 and M22556, cow N-cadherin X53615, human P-cadherin X63629, mouse P-cadherin X06340, human E-cadherin Z13009, mouse E-cadherin X06115, mouse R-cadherin D14888, and human R-cadherin NM_001794. Alternatively, additional residues present on one or both sides of the Trp-containing CAR sequence(s) may be unrelated to an endogenous sequence (e.g., residues that facilitate cyclization, purification or other manipulation and/or residues having a targeting or other function).

In certain preferred embodiments, a modulating agent comprises a cyclic peptide having one of the following structures:

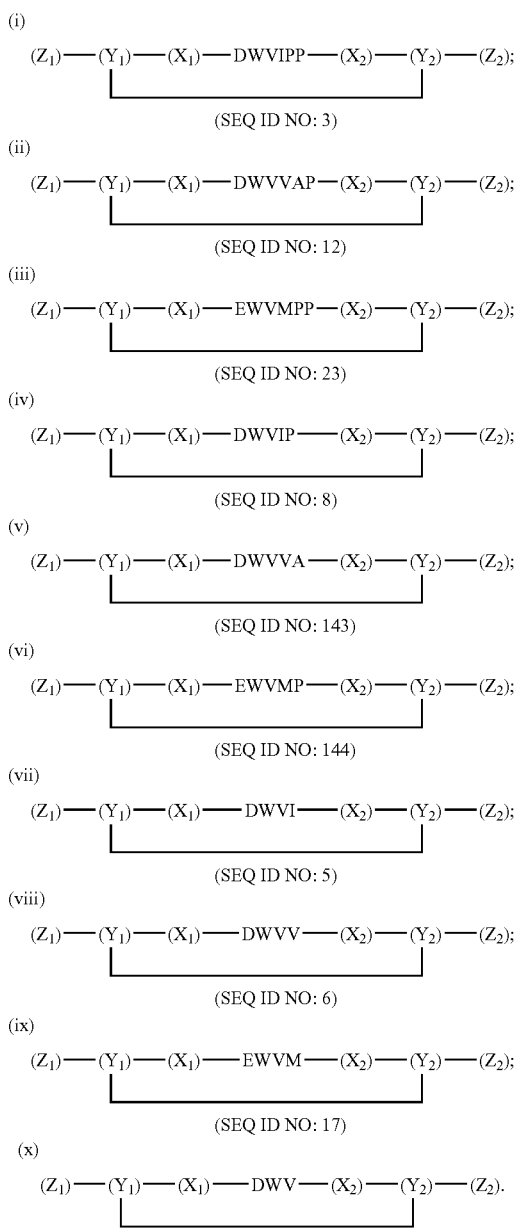

(i)

$(Z_1)$—$(Y_1)$—$(X_1)$—DWVIPP—$(X_2)$—$(Y_2)$—$(Z_2)$;

(SEQ ID NO: 3)

(ii)

$(Z_1)$—$(Y_1)$—$(X_1)$—DWVVAP—$(X_2)$—$(Y_2)$—$(Z_2)$;

(SEQ ID NO: 12)

(iii)

$(Z_1)$—$(Y_1)$—$(X_1)$—EWVMPP—$(X_2)$—$(Y_2)$—$(Z_2)$;

(SEQ ID NO: 23)

(iv)

$(Z_1)$—$(Y_1)$—$(X_1)$—DWVIP—$(X_2)$—$(Y_2)$—$(Z_2)$;

(SEQ ID NO: 8)

(v)

$(Z_1)$—$(Y_1)$—$(X_1)$—DWVVA—$(X_2)$—$(Y_2)$—$(Z_2)$;

(SEQ ID NO: 143)

(vi)

$(Z_1)$—$(Y_1)$—$(X_1)$—EWVMP—$(X_2)$—$(Y_2)$—$(Z_2)$;

(SEQ ID NO: 144)

(vii)

$(Z_1)$—$(Y_1)$—$(X_1)$—DWVI—$(X_2)$—$(Y_2)$—$(Z_2)$;

(SEQ ID NO: 5)

(viii)

$(Z_1)$—$(Y_1)$—$(X_1)$—DWVV—$(X_2)$—$(Y_2)$—$(Z_2)$;

(SEQ ID NO: 6)

(ix)

$(Z_1)$—$(Y_1)$—$(X_1)$—EWVM—$(X_2)$—$(Y_2)$—$(Z_2)$;

(SEQ ID NO: 17)

(x)

$(Z_1)$—$(Y_1)$—$(X_1)$—DWV—$(X_2)$—$(Y_2)$—$(Z_2)$.

-continued (xi)

$(Z_1)$—$(Y_1)$—$(X_1)$—EWV—$(X_2)$—$(Y_2)$—$(Z_2)$.

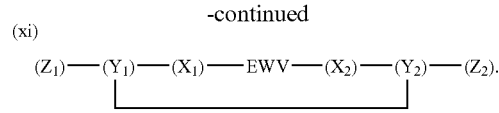

In these structures, $X_1$ and $X_2$ are optional, and if present, are amino acid residues or combinations of amino acid residues linked by peptide bonds. $X_1$ and $X_2$ may be identical to, or different from, each other. In general, $X_1$ and $X_2$ independently range in size from 0 to 10 residues, such that the sum of residues contained within $X_1$ and $X_2$ ranges from 1 to 12. $Y_1$ and $Y_2$ are amino acid residues, and a covalent bond is formed between residues $Y_1$ and $Y_2$. $Y_1$ and $Y_2$ may be identical to, or different from, each other. $Z_1$ and $Z_2$ are optional, and if present, are amino acid residues or combinations of amino acid residues linked by peptide bonds. $Z_1$ and $Z_2$ may be identical to, or different from, each other.

A modulating agent that contains sequences that flank the Trp-containing CAR sequence on one or both sides may be specific for cell adhesion mediated by one or more specific cadherins, resulting in tissue and/or cell-type specificity. Suitable flanking sequences for conferring specificity include, but are not limited to, endogenous sequences present in one or more naturally occurring cadherins. Modulating agents having a desired specificity may be identified using the representative screens provided herein.

In certain embodiments, a modulating agent may comprise multiple CAR sequences (including CAR sequences other than a Trp-containing CAR sequence). The total number of CAR sequences (including both Trp-containing CAR sequence and CAR sequences other than Trp-containing CAR sequences) present within a modulating agent may range from 1 to a large number, such as 100 or 50, preferably from 1 to 10, and more preferably from 1 to 5 (including all integer values in between). CAR sequences that may be included within a modulating agent are any sequences that are an extracellular portion of an adhesion molecule and involved in interaction of the adhesion molecule with another adhesion molecule. As used herein, a "modulating molecule" (also referred to as "cell adhesion modulating molecule") is a molecule that mediates cell adhesion via a receptor on the cell's surface. Adhesion molecules include members of the cadherin gene superfamily that are not classical cadherins (e.g., proteins that do not contain an HAV sequence and/or one or more of the other characteristics recited above for classical cadherins), such as desmogleins (Dsg) and desmocollins (Dsc); integrins; members of the immunoglobulin supergene family, such as N-CAM and JAM; and other transmembrane proteins, such as the tight junction associated proteins occludin and claudins, as well as extracellular matrix proteins such as laminin, fibronectin, collagens, vitronectin, entactin and tenascin. Within certain embodiments, preferred CAR sequences for inclusion within a modulating agent include (a) Arg-Gly-Asp (RGD), which is bound by integrins (see Cardarelli et al., *J. Biol. Chem.* 267:23159-64, 1992); (b) Tyr-Ile-Gly-Ser-Arg (YIGSR) (SEQ ID NO: 145), which is bound by $\alpha6\beta1$ integrin; (c) KYSFNYDGSE (SEQ ID NO: 146), which is bound by N-CAM; (d) the junctional adhesion molecule (JAM; see Martin-Padura et al., *J. Cell. Biol.* 142:117-127, 1998) CAR sequence SFTIDPKSG (SEQ ID NO: 147) or DPK; (e) the occludin CAR sequence LYHY (SEQ ID NO: 148); (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO: 149), wherein Aaa, Baa and Caa indicate amino acid residues that may be identical to, or different from, one another; Lys/Arg is an amino acid that is lysine or arginine; Ser/Ala is an amino acid that is serine or alanine; and Tyr/Phe is an amino acid that is tyrosine or phenylalanine; and (g) nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO: 150), wherein Aaa, Baa, Caa and Daa are amino acid residues that may be identical to, or different from, one another; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO: 151), TSSY (SEQ ID NO: 152), VTAF (SEQ ID NO: 153) and VSAF (SEQ ID NO: 154). Representative nonclassical cadherin CAR sequences include the VE-cadherin (cadherin-5) CAR sequence DAE-and the OB-cadherin (cadherin-11) CAR sequence DDK. These and other representative CAR sequences useful in conjunction with the Trp-containing CAR sequences described herein can be found, for example, in U.S. Pat. Nos. 6,031,072, 6,169,071, 6,207,639, 6,562,786, 6,346,512, 6,333,307, 6,417,325, 6,465,427, 6,326,352, 6,203,788, 6,277,824, 6,472,368, 6,248,864, 6,110,747, 6,310,177, 6,472,367, 6,358,920, 6,433,149, 6,303,576, and 6,391,855, the disclosures of which are incorporated herein by reference in their entireties.

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Exemplary linkers include, but are not limited to, $(H_2N(CH_2)_nCO_2H)_m$ or derivatives thereof (where n ranges from 1 to 10 and integer values therebetween, and m ranges from 1 to 4000 and integer values therebetween), glycine ($H_2NCH_2CO_2H$), aminopropanoic acid, aminobutanoic acid, aminopentanoic acid, amino hexanoic acid, 2,3-diaminopropanoic acid, lysine or ornithine, or multimers of the above compounds. Peptide and non-peptide linkers may generally be incorporated into a modulating agent using any appropriate method known in the art.

Using a linker, peptides comprising Trp-containing CAR and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR (SEQ ID NO: 145) and a Trp-containing CAR sequence. Within another embodiment, modulating agents having a branched structure may comprise RGD, YIGSR (SEQ ID NO: 145), a Trp-containing CAR sequence and KYSFNYDGSE (SEQ ID NO: 146). In a third embodiment, modulating agents having a branched structure comprise a Trp-containing CAR sequence, one or more desmocollin (Dsc) CAR sequences, one or more desmoglein (Dsg) CAR sequences and the occludin CAR sequence LYHY (SEQ ID NO: 148).

In certain embodiments, modulating agents comprise two, three, four, or more Trp-containing CAR sequences, which may be adjacent to one another (i.e., without intervening sequences) or separated by peptide and/or non-peptide linkers. At least one of the Trp-containing CAR sequences of the modulating agents is within a cyclic peptide ring. In certain embodiments, all the multiple Trp-containing CAR sequences in the modulating agents are within cyclic peptide rings. The cyclic peptide rings may contain at most 100, 80, 60, 50, 40, 30, 25, 20, or 15 amino acid residues. These Trp-containing CAR sequence in the cyclic peptides may be linked in tandem (e.g., in CDWVIPPDWVIPPC (SEQ ID NO: 155)). Alternatively, at least some of the Trp-containing CAR sequences may be linked with each other in a trans configuration (e.g., in CDWVIPPPPIVWDC (SEQ ID NO: 156) or in CPPWWDDWVIPPC (SEQ ID NO: 157)). The linkers that separate Trp-containing CAR sequences in certain embodiments may comprise one or more amino acid residues that flank (i.e., are adjacent to) the Trp-containing CAR sequence on either side of the sequence in a naturally occurring cadherin molecule. Within one such embodiment, the cyclic peptide contains two Trp-containing CAR sequences. The two Trp-containing CAR sequences may be linked in a cis configuration (i.e., in tandem) or in a trans configuration.

Whether a modulating agent that comprises multiple Trp-containing CAR sequences inhibits or enhances cell adhesion may depend on whether multiple Trp-containing CAR sequences are capable of adopting the natural structure of the Trp-containing CAR sequences (i.e., the structure of the Trp-containing CAR sequence in a naturally occurring cadherin molecule) to facilitate binding among cadherin molecules. For instance, certain modulating agents having two or more Trp-containing CAR sequences may adopt a structure that would allow for the presentation of two or more Trp-containing CAR sequences in their natural configurations (used interchangeably with "conformations"). Such presentation allows the modulating agents to simultaneously interact with two or more cadherin molecules in the cell membrane and therefore promote dimerization or the formation of multimer of these cadherin molecules. In contrast, some other modulating agents incapable of adopting a structure that allow for the presentation of more than one Trp-containing CAR sequence in its natural configuration would be expected to inhibit, rather than facilitate, the interaction among cadherin molecules.

The configuration of a candidate modulating agent may be determined by any appropriate methods known in the art, including NMR techniques and computational techniques (see, Bowen et al., *J. Clin. Pharmacol.* 33:1149-64, 1993; Lesyng and McCammon, *Pharmacol. Ther.* 60: 149-67, 1993; Nikiforovich, Int. *J. Pept. Protein Res.* 44:513-31, 1994; Shoichet and Kuntz, *Protein Eng.* 6: 723-32, 1993; DesJarlais and Dixon, *J. Comput. Aided Mol. Des.* 8: 231-42, 1994; Oshiro et al., *J. Comput. Aided Mol. Des.* 9:113-30, 1995). In addition, molecular modeling of a modulating agent may also be used to facilitate the determination as to whether two or more Trp-containing CAR sequences in the modulating agent have the potential to simultaneously interact with two or more cadherin molecules. Such molecular modeling may be facilitated by the use of known crystal structures of the amino-terminal domain (i.e., EC1) of various cadherin molecules.

The above modulating agents may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the Trp-containing CAR sequence(s) and/or each other. Such modulating agents may be used within methods in which it is desirable to simultaneously disrupt cell adhesion mediated by multiple adhesion molecules. Within certain preferred embodiments, the second CAR sequence is derived from fibronectin and is recognized by an integrin (i.e., RGD; see Cardarelli et al., *J Biol. Chem.* 267:23159-23164, 1992), or is an occludin CAR sequence (e.g., LYHY). One or more antibodies, or fragments thereof, may similarly be used within such embodiments.

As described above, modulating agents that enhance cell adhesion may contain multiple Trp-containing CAR sequences, and/or antibodies that specifically bind to such sequences, joined directly or by linkers with each other. Enhancement of cell adhesion may also be achieved by attachment of multiple modulating agents to a support molecule or material, as discussed further below. Such modulating agents may additionally comprise one or more CAR sequence for one or more different adhesion molecules (including, but not limited to, other CAMs) and/or one or more antibodies or fragments thereof that bind to such sequences, to enhance cell adhesion mediated by multiple adhesion molecules.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; $\alpha$- and $\beta$-amino acids are generally preferred. The 20 L-amino acids commonly found in proteins are identified herein by the conventional three-letter or one-letter abbreviations.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, $\alpha$-aminoadipic acid, m-aminomethylbenzoic acid and $\alpha,\beta$-diaminopropionic acid.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solid phase peptide synthesis techniques, in which a peptide linkage occurs through the direct condensation of the $\alpha$-amino group of one amino acid with the $\alpha$-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for $\alpha$-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the $\alpha$-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-$\alpha$-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline.

Within another embodiment, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC (SEQ ID NO: 158) or DCCI (SEQ ID NO: 159), resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction byproducts. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino)phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC (SEQ ID NO: 158)) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

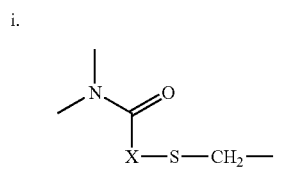

$X = (CH_2)_4$
$= CH_2$

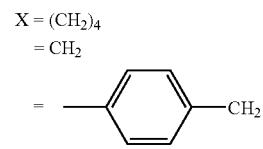

ii.

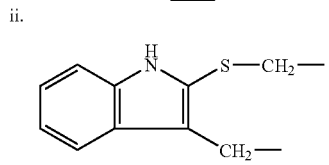

Cyclization may also be achieved using $\delta_1,\delta_1$-Ditryptophan.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol. Biol.* 211:679-682, 1990), or from sequences isolated by screening an appropriate library with probes designed based on the sequences of known cadherins. Such screens may generally be performed as described in Sambrook et al., *Molecular Cloning: A Laboratory Manual,* Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, the modulating agent of the present invention may comprise a peptidomimetic instead of (or in addition to) a Trp-containing CAR sequence. The peptidomimetic must have a detectable cell adhesion modulating activity. Peptidomimetics generally have improved oral availability, which makes them especially suited to treatment of conditions such as cancer. It should be noted that peptidomimetics may or may not have similar two-dimensional chemical structures, but share common three-dimensional structural features and geometry. Each peptidomimetic may further have one or more unique additional binding elements. The present invention provides methods for designing, screening and/or identifying peptidomimetics.

In certain embodiments, the pharmacophore of one or more Trp-containing CAR sequences described above is first mapped to facilitate the designing of peptidomimetics. The term "pharmacophore" refers to the collection of functional groups on a compound that are arranged in three-dimensional space in a manner complementary to the target protein, and that are responsible for biological activity as a result of compound binding to the target protein. Useful three-dimensional pharmacophore models may be derived from either crystallographic or nuclear magnetic resonance (NMR) structures of the target (e.g., X-ray structure of N-cadherin and X-ray structure or NMR structure of E-cadherin). Alternatively, ligand structure-activity relationships may be used to map the binding site of the ligand. More specifically, structure-activity relationships of structurally diverse and conformationally informative molecules are used to propose a pharmacophore. Such relationships establish the required groups for the activities of the ligands. Conformationally constrained compounds that are also active may help establish the bioactive conformation of all the ligands. The molecules are superimposed, in their proposed bioactive conformations, over the atoms of the pharmacophore or their projected binding points on the macromolecule (i.e., receptor). The union of the volumes occupied by the active compounds as superimposed suggests the regions that can be occupied by any newly designed active ligand. In addition, regions occupied by compounds that meet the pharmacophore requirements but are inactive define "forbidden regions" that, if occupied, destroy activity.

The three-dimensional structures of Trp-containing CAR sequences may generally be determined using nuclear magnetic resonance (NMR) techniques that are well known in the art. NMR data acquisition is preferably carried out in aqueous systems that closely mimic physiological conditions to ensure that a relevant structure is obtained. Briefly, NMR techniques use the magnetic properties of certain atomic nuclei (such as $^1H$, $^{13}C$, $^{15}N$ and $^{31}P$), which have a magnetic moment or spin, to probe the chemical environment of such nuclei. The NMR data can be used to determine distances between atoms in the molecule, which can be used to derive a three-dimensional model or the molecule.

For determining three-dimensional structures of Trp-containing CAR sequences (and candidate peptidomimetics, as discussed below) proton NMR is preferably used. More specifically, when a molecule is placed in a strong magnetic field, the two spin states of the hydrogen atoms are no longer degenerate. The spin aligned parallel to the field will have a lower energy and the spin aligned antiparallel to the field will have a higher energy. At equilibrium, the spin of the hydrogen atoms will be populated according to the Boltzmann distribution equation. This equilibrium of spin populations can be perturbed to an excited state by applying radio frequency (RF) pulses. When the nuclei revert to the equilibrium state, they emit RF radiation that can be measured. The exact frequency of the emitted radiation from each nucleus depends on the molecular environment of the nucleus and is different for each atom (except for those atoms that have the same molecular environment). These different frequencies are obtained relative to a reference signal and are called chemical shifts. The nature, duration and combination of applied RF pulses can be varied greatly and different molecular properties can be probed by those of ordinary skill in the art, by selecting an appropriate combination of pulses.

For three-dimensional structure determinations, one-dimensional NMR spectra are generally insufficient, as limited information pertaining to conformation may be obtained. One-dimensional NMR is generally used to verify connectivity within a molecule and yields incomplete data concerning the orientation of side chains within a peptide. Two-dimensional NMR spectra are much more useful in this respect and allow for unambiguous determination of side-chain-to-side-chain interactions and the conformation of the peptide backbone.

Two-dimensional NMR spectra are generally presented as a contour plot in which the diagonal corresponds to a one-dimensional NMR spectrum and the cross peaks off the diagonal result from interactions between hydrogen atoms that are directly scalar coupled. Two-dimensional experiments generally contain a preparation period, an evolution period where spins are "labeled" as they process in the XY plane according to their chemical shift, a mixing period, during which correlations are made with other spins and a detection period in which a free induction decay is recorded.

Two-dimensional NMR methods are distinguished by the nature of the correlation that is probed during the mixing period. A DQF-COSY (double quantum filtered correlation spectroscopy) analysis gives peaks between hydrogen atoms that are covalently connected through one or two other atoms. Nuclear Overhauser effect spectroscopy (NOESY) gives peaks between pairs of hydrogen atoms that are close together in space, even if connected by way of a large number of intervening atoms. In total correlation spectroscopy (TOCSY), correlations are observed between all protons that share coupling partners, whether or not they are directly coupled to each other. Rotating-frame Overhauser Spectroscopy (ROESY) experiments may be thought of as the rotating frame analogue of NOESY, and yields peaks between pairs of hydrogen atoms that are close together in space. One or more such methods may be used, in conjunction with the necessary water-suppression techniques such as WATERGATE and water flip-back, to determine the three-dimensional structure of a Trp-containing CAR sequence or candidate peptidomimetic under aqueous conditions. Such techniques are well known and are necessary to suppress the resonance of the solvent (HDO) during acquisition of NMR data.

By way of example, both TOCSY and NOESY may be applied to representative Trp-containing CAR sequences for the purpose of determining the conformation and the assignment. The water solvent resonance may be suppressed by application of the WATERGATE procedure. A water flipback pulse may also be applied at the end of the mixing period for both TOCSY and NOESY experiments to maintain the water signal at equilibrium and to minimize the loss of amide proton resonances due to their rapid exchange at the near neutral pH conditions (i.e., pH 6.8) used in the experiment. NMR data may be processed using spectrometer software using a squared cosine window function along both directions. Baseline corrections may be applied to the NOESY, ROESY and TOCSY spectra using the standard Bruker polynomial method.

NOESY data may be acquired at several mixing times ranging from 80 ms to 250 ms. The shorter mixing time NOESY may be acquired to ensure that no diffusion effects were present in the NOESY spectrum acquired at the longer mixing times. The interproton distances may generally be determined from the 250 ms NOESY. The sequence-specific assignment of the proton resonances may be determined by standard methods (see Wuthrich, *NMR of Proteins and Nucleic Acids*, Wiley & Sons, New York, 1986), making use of both the results of the TOCSY and NOESY data. The spin systems of Ala3 and Val4 may be assigned based on the presence of strong NOEs between the amide protons and the respective side chains in conjunction with the relevant TOCSY data.

For conformational calculations, the NOE cross peaks may be initially converted to a uniform distance upper and lower bounds of 1.8-5.0 angstroms regardless of the NOE intensities. The NOE distances may be refined iteratively through a comparison of computed and experimental NOEs at the various mixing times. This refinement may be much in the spirit of the PEPFLEX-II procedure (Wang et al., Techniques in Protein Chemistry IV, 1993, Evaluation of NMR Based Structure Determination for Flexible Peptides: Application to Desmopressin p. 569), although preferably initial NOE-based distances with very loose upper bounds (e.g., 5 angstroms) are used to permit the generation of a more complete set of conformations in agreement with experimental data. Dihedral-angle constraints may be derived from the values of the $^3J_{C\alpha H}$ coupling constants. A tolerance value of 40 degrees may be added to each of the dihedral angle constraints to account for the conformational flexibility of the peptide. Distance geometry calculations may be carried out utilizing fixed bond lengths and bond angles provided in the ECEPP/2 database (Ni et al., *Biochemistry* 31:11551-11557, 2989). The $\omega$-angles are generally fixed at 180 degrees, but all other dihedral angles may be varied during structure optimization.

Structures with the lowest constraint violations may be subjected to energy minimization using a distance-restrained Monte Carlo method (Ripoll and Ni, *Biopolymers* 32:359-365, 1992; Ni, *J. Magn. Reson.* B106:147-155, 1995), and modified to include the ECEPP/3 force field (Ni et al., *J. Mol. Biol.* 252:656-671, 1995). All ionizable groups may be treated as charged during constrained Monte Carlo minimization of the ECEPP/3 energy. Electrostatic interactions among all charges may be screened by use of a distance-dependent dielectric to account for the absence of solvent effects in conformational energy calculations. In addition, hydrogen-bonding interactions can be reduced to 25% of the full scale, while van der Waals and electrostatic terms are kept to full strengths. These special treatments help to ensure that the conformational search is guided primarily by the experimental NMR constraints and that the computed conformations are less biased by the empirical conformational energy parameters (Warder et al., *FEBS Lett.* 411:19-26, 1997).

Low-energy conformations of the peptide from Monte Carlo calculations may be used in NOE simulations to identify proximate protons with no observable NOEs and sets of distance upper bounds that warrant recalibration. The refined set of NOE distances including distance lower bounds derived from absent NOEs are used in the next cycles of Monte Carlo calculations, until the resulting conformations produced simulate NOE spectra close to those observed experimentally (Ning et al., *Biopolymers* 34:1125-1137, 1994; Ni et al., *J. Mol. Biol.* 252:656-671, 1995). Theoretical NOE spectra may be calculated using a tumbling correlation time of 1.5 ns based on the molecular weight of the peptide and the experimental temperature (Cantor, C. R. and Schimmel, P. R. (1980) *Biophysical Chemistry*, W. H. Freeman & Co., San Francisco). All candidate peptide conformations are included with equal weights in an ensemble-averaged relaxation matrix analysis of interconverting conformations (Ni and Zhu *J. Magn. Reson.* B102:180-184, 1994). NOE simulations may also incorporate parameters to account for the local motions of the methyl groups and the effects of incomplete relaxation decay of the proton demagnitizations (Ning et al., *Biopolymers* 34:1125-1137, 1994). The computed NOE intensities are converted to the two-dimensional FID's (Ni, *J. Magn. Reson.* B106: 147-155, 1995) using the chemical shift of assignments, estimated linewidths and coupling constants for all resolved proton resonances. Calculated FIDs may be converted to simulated NOESY spectra using identical processing procedures as used for the experimental NOE data sets.

As noted above, the peptidomimetics of the present invention have a three-dimensional structure that is substantially similar to a three-dimensional structure of a Trp-containing CAR sequence as described above. In general, two three-dimensional structures are said to be substantially structurally similar to each other if their pharmacophore atomic coordinates have a root-mean square deviation (RMSD) less than or equal to 1 angstrom, as calculated using the Molecular Similarity module within the QUANTA program (QUANTA, available from Molecular Simulations Inc., San Diego, Calif.). All peptidomimetics provided herein have at least one low-energy three-dimensional structure that is substantially similar to at least one low-energy three-dimensional structure of a Trp-containing CAR sequence as described above.

Low energy conformations may be identified by conformational energy calculations using, for example, the CHARMM program (Brooks et al., *J. Comput. Chem.* 4:187-217, 1983). The energy terms include bonded and non-bonded terms, including bond length energy, angle energy, dihedral angle energy, Van der Waals energy and electrostatic energy. It will be apparent that the conformational energy can be also calculated using any of a variety of other commercially available quantum mechanic or molecular mechanic programs. A low energy structure has a conformational energy that is within 50 kcal/mol of the global minimum.

The low energy conformation(s) of candidate peptidomimetics are compared to the low energy solution conformations of the Trp-containing CAR sequence (as determined by NMR) to determine how closely the conformation of the candidate mimics that of the Trp-containing CAR sequence. In such comparisons, particular attention should be given to the locations and orientations of the elements corresponding to the crucial side chains. If at least one of the candidate low energy conformations is substantially similar to a solution conformation of a Trp-containing CAR sequence (i.e., differs with a root-mean square deviation (RMSD) of 1 angstrom or less), the candidate compound is considered a peptidomimetic. Within such analyses, low energy conformations of candidate peptidomimetics in solution may be studied using, for example, the CHARMM molecular mechanics and molecular dynamics program (Brooks et al., *J. Comput. Chem.* 4:187-217, 1983), with the TIP3P water model (Jorgensen et al., *J. Chem Phys.* 79:926-935, 1983) used to represent water molecules. The CHARM22 force field may be used to represent the designed peptidomimetics.

By way of example, low energy conformations may be identified using a combination of two procedures. The first procedure involves a simulated annealing molecular dynamics simulation approach. In this procedure, the system (which includes the designed peptidomimetics and water molecules) is heated up to above room temperature, preferably around 600 K, and simulated for a period of 100 picoseconds (ps) or longer; then gradually reduced to 500 K and simulated for a period of 100 ps or longer; then gradually reduced to 400 K and simulated for a period of 100 ps or longer; gradually reduced to 300 K and simulated for a period of 500 ps or longer. The trajectories are recorded for analysis. This simulated annealing procedure is known for its ability for efficient conformational search.

The second procedure involves the use of the self-guided molecular dynamics (SGMD) method (Wu and Wang, *J. Physical Chemistry* 102:7238-7250, 1998). The SGMD method has been demonstrated to have an extremely enhanced conformational searching capability. Using the SGMD method, simulation may be performed at 300 K for 1000 ps or longer and the trajectories recorded for analysis.

Conformational analysis may be carried out using the QUANTA molecular modeling package. First, cluster analysis may be performed using the trajectories generated from molecular dynamic simulations. From each cluster, the lowest energy conformation may be selected as the representative conformation for this cluster and may be compared to other conformational clusters. Upon cluster analysis, major conformational clusters may be identified and compared to the solution conformations of the Trp-containing CAR sequence(s). The conformational comparison may be carried out using the Molecular Similarity module within the QUANTA program.

Similarity in structure may also be evaluated by visual comparison of the three-dimensional structures displayed in a graphical format, or by any of a variety of computational comparisons. For example, an atom equivalency may be defined in three-dimensional structures of the peptidomimetic and a Trp-containing CAR sequence, and a fitting operation used to establish the level of similarity. As used herein, an "atom equivalency" is a set of conserved atoms in the two structures. A "fitting operation" may be any process by which a candidate compound structure is translated and rotated to obtain an optimum fit with the structure of the Trp-containing CAR sequence. A fitting operation may be a rigid fitting operation (e.g., the three-dimensional structure of the Trp-containing CAR sequence can be kept rigid and the three-dimensional structure of the peptidomimetic can be translated and rotated to obtain an optimum fit with the Trp-containing CAR sequence). Alternatively, the fitting operation may use a least squares fitting algorithm that computes the optimum translation and rotation to be applied to the moving compound structure, such that the root mean square difference of the fit over the specified pairs of equivalent atoms is a minimum. Preferably, atom equivalencies may be established by the user and the fitting operation is performed using any of a variety of available software applications (e.g., QUANTA, available from Molecular Simulations Inc., San Diego, Calif.). Three-dimensional structures of candidate compounds for use in establishing substantial similarity may be determined experimentally (e.g., using NMR techniques as described herein or x-ray crystallography), or may be computer-generated using, for example, methods provided herein.

Figure 5:
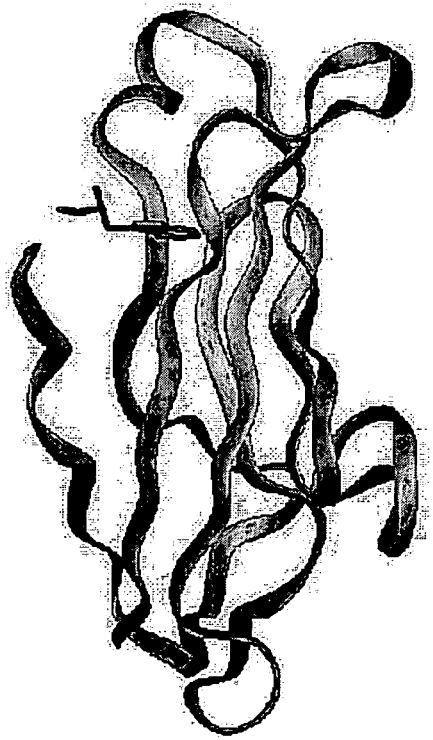
FIG. 5 shows schematic representation of the binding between the N-terminal residue Trp2 in an N-cadherin molecule (the "ligand") and the N-terminal domain (EC1) of another N-cadherin molecule (the "receptor").

Certain peptidomimetics may be designed, based on the structure of a Trp-containing CAR sequence. For example, such peptidomimetics may mimic the local topography about the cleavable amide bonds (amide bond isosteres). These mimetics often match the peptide backbone atom-for-atom, while retaining functionality that makes important contacts with the binding sites. Amide bond mimetics may also include the incorporation of unusual amino acids or dipeptide surrogates (see FIG. 5, and other examples in Gillespie et al., *Biopolymers* 43:191-217, 1997). The conformationally rigid substructural elements found in these types of mimetics are believed to result in binding with highly favorable entropic driving forces, as compared to the more conformationally flexible peptide linkages. Backbone modifications can also impart metabolic stability towards peptidase cleavage relative to the parent peptide. Other peptidomimetics may be secondary structure mimics.

To design a peptidomimetic, heuristic rules that have been developed through experience may be used to systematically modify a Trp-containing CAR sequence. Within such modification, empirical data of various kinds are generally collected throughout an iterative refinement process. As noted above, optimal efficiency in peptidomimetic design requires a three-dimensional structure of the pharmacophore.

Peptidomimetics can also be designed based on a visual comparison of the pharmacophore of a Trp-containing CAR sequence with a three-dimensional structure of a candidate compound, using knowledge of the structure-activity relationships of the Trp-containing CAR sequence. Structure-activity studies should establish important binding elements in the Trp-containing CAR sequences, which in turn should be retained in the designed peptidomimetics.

As an alternative to design by visual inspection, libraries may be made using combinatorial chemical techniques. Combinatorial chemical technology enables the parallel synthesis of organic compounds through the systematic addition of defined chemical components using highly reliable chemical reactions and robotic instrumentation. Large libraries of compounds result from the combination of all possible reactions that can be done at one site with all the possible reactions that can be done at a second, third or greater number of sites. Combinatorial chemical methods can potentially generate tens to hundreds of millions of new chemical compounds as mixtures, attached to a solid support, or as individual compounds. Methods for constructing peptidomimetic synthetic combinatorial libraries are known in the art and discussed in many journal articles (e.g., Eichler et al., *Medicinal Research Review* 15: 481-96, 1995; Al-Obeidi et al., *Molecular Biotechnology* 9: 205-23, 1998; Hruby et al., *Current Opinion in Chemical Biology* 1: 114-9, 1997; and Ripka and Rich, *Current Opinion in Chemical Biology* 2: 441-52, 1998).

Pharmacophores can be used to facilitate the screening of such chemical libraries. For example, instead of producing all possible members of every library (resulting in an unwieldy number of compounds), library synthesis can focus on the library members with the greatest probability of interacting with the target. The integrated application of structure-based design and combinatorial chemical technologies can produce synergistic improvements in the efficiency of drug discovery.

Further peptidomimetics are compounds that appear to be unrelated to the original peptide, but contain functional groups positioned on a nonpeptide scaffold that serve as topographical mimics. This type of peptidomimetic may be identified using library screens of large chemical databases. Such screens use the three-dimensional conformation of a pharmacophore to search such databases in three-dimensional space. A single three-dimensional structure may be used as a pharmacophore model in such a search. Alternatively, a pharmacophore model may be generated by considering the crucial chemical structural features present within multiple three-dimensional structures.

Any of a variety of databases of three-dimensional structures may be used for such searches. A database of three-dimensional structures may be prepared by generating three-dimensional structures of a database of compounds, and storing the three-dimensional structures in the form of data storage material encoded with machine-readable data. The three-dimensional structures can be displayed on a machine capable of displaying a graphical three-dimensional representation and programmed with instructions for using the data. Within preferred embodiments, three-dimensional structures are supplied as a set of coordinates that define the three-dimensional structure.

Preferably, the 3D-database contains at least 100,000 compounds, with small, non-peptidyl molecules having relatively simple chemical structures particularly preferred. It is also important that the 3D co-ordinates of the compounds in the database be accurately and correctly represented. The National Cancer Institute (NCI) 3D-database (Milne et al., *J. Chem. Inf. Comput. Sci.* 34:1219-1224, 1994) and the Available Chemicals Directory (ACD; available from MDL Information Systems, San Leandro, Calif.) are two excellent databases that can be used to generate a database of three-dimensional structures, using molecular modeling, as discussed above. For flexible molecules, which can have several low-energy conformations, it is desirable to store and search multiple conformations. The Chem-X program (Oxford Molecular Group PLC; Oxford UK) is capable of searching thousands or even millions of conformations for a flexible compound. This capability of Chem-X provides a real advantage in dealing with compounds that can adopt multiple conformations. Using this approach, hundreds of millions of conformations can be searched in a 3D-pharmacophore searching process.

The Available Chemical Database may also be screened for appropriate peptidomimetics. To facilitate pharmacophore searching, the entire ACD database is converted into 3-D conformations, which can be searched using the Chem-X program.

A pharmacophore search typically involves three steps. The first step is the generation of a pharmacophore query. Such queries may be developed from an evaluation of critical distances in the three dimensional structure of a Trp-containing CAR sequence. Using the pharmacophore query of interest, a distance bit screening is performed on the database to identify compounds that fulfill the required geometrical constraints. In other words, compounds that satisfy the specified critical pair-wise distances are identified. After a compound passed the distance bit screening step, the program next checks whether the compound meets the substructural requirements as specified in the pharmacophore query. After a compound passes this sub-structural check, it is finally subjected to a conformational analysis. In this step, conformations are generated and evaluated with regard to geometric requirements specified in the pharmacophore query. Compounds that have at least one conformation satisfying the geometric requirements, are considered as 'hits' and are recorded in a result database.

In some embodiments, computer modeling without the identification of a pharmacophore may also be used to search for appropriate peptidomimetics. For instance, computer program DOCK, which uses spheres to describe the active site of a molecule ("receptor") known from, for example, X-ray crystallography. The "negative" image of this receptor site is then used to test out compounds from a database (e.g., Cambridge Crystallographic Database, Maybridge Structural Database, and ChemDiv Database). Using a score to rank these molecules docked onto the receptor site, compounds that fit well onto the receptor site may be obtained.

Another computer program CAVEAT may also be used to peptidomimetic searches. For every molecule in a database, the program stores the intramolecular bonds as vectors. The resulting new database of vectors is then searched for vector matching. In other words, this approach starts with the crystal structure of a ligand in complex with a receptor and then search for new templates based on the spatial arrangements of the bonds of this known ligand.

While compounds (i.e., hits) selected from databases satisfy the requirements for three-dimensional similarity, it will be apparent to those of ordinary skill in the art that further biological testing may be used to select compounds with optimal activity. It will further be apparent that other criteria may be considered when selecting specific compounds for particular applications, such as the simplicity of the chemical structure, low molecular weight, chemical structure diversity and water solubility. The application of such criteria is well understood by medicinal, computational and structural chemists.

It will be apparent that a compound structure may be optimized using screens as provided herein. Within such screens, the effect of specific alterations of a candidate compound on three-dimensional structure may be evaluated to optimize three-dimensional similarity to a Trp-containing CAR sequence. Such alterations include, for example, changes in hydrophobicity, steric bulk, electrostatic properties, size and bond angle.

Biological testing of candidate compounds may be used to confirm peptidomimetic activity. In general, peptidomimetics should function in a substantially similar manner as a structurally similar Trp-containing CAR sequence. In other words, a peptidomimetic of a Trp-containing CAR sequence should bind to a classical cadherin with an affinity that is at least half the affinity of the Trp-containing CAR sequence, as measured using standard binding assays. Further, a peptidomimetic of the Trp-containing CAR sequence should modulate a classical cadherin-mediated function using a representative assay provided herein at a level that is at least half the level of modulation achieved using the Trp-containing CAR sequence.

Once an active peptidomimetic has been identified, related analogues may be identified using two-dimensional similarity searching. Such searching may be performed, for example, using the program ISIS Base (Molecular Design Limited). Two-dimensional similarity searching permits the identification of other available, closely related compounds, which may be readily screened to optimize biological activity. The active peptidomimetic and its related analogues may be prepared or produced by any methods or chemical reactions known in the art.

As noted above, instead of (or in addition to) a Trp-containing CAR sequence, a modulating agent may comprise an antibody, or antigen-binding fragment thereof, that specifically binds to a Trp-containing CAR sequence. As used herein, an antibody, or antigen-binding fragment thereof, is said to "specifically bind" to a Trp-containing CAR sequence (with or without flanking amino acids) if it reacts at a detectable level with a peptide containing that sequence, and does not react detectably with peptides containing a different CAR sequence or a sequence in which the order of amino acid residues in the cadherin CAR sequence and/or flanking sequence is altered. Such antibody binding properties may be assessed using an ELISA, as described by Newton et al., *Develop. Dynamics* 197:1-13, 1993. In certain embodiments, the dissociation constant of the interaction between an antibody molecule and a Trp-containing CAR sequence is at most $10^{-7}$ M. In other embodiments, the dissociation constant is at most $10^{-8}$ M.

Polyclonal and monoclonal antibodies may be raised against a Trp-containing CAR sequence using conventional techniques. See, e.g., Harlow and Lane, *Antibodies: A Laboratory Manual*, Cold Spring Harbor Laboratory, 1988. In one such technique, an immunogen comprising the Trp-containing CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for the Trp-containing CAR sequence may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within preferred embodiments, such monoclonal antibodies are specific for particular cadherins (e.g., the antibodies bind to E-cadherin, but do not bind significantly to N-cadherin, or vise versa). Such antibodies may be prepared as described above, using an immunogen that comprises (in addition to a minimal Trp-containing CAR sequence) sufficient flanking sequence to generate the desired specificity. To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628-29).

Within certain embodiments, antibodies may be used within methods in which enhanced cell adhesion is desired, as described above. For example, antibodies may be used within the above methods for enhancing and/or directing neurite outgrowth in vitro or in vivo. Antibodies may be used within the lumen of a tubular nerve guide or may be attached to a fiber nerve guide, suture or other solid support and used as described above for peptide modulating agents. Antibody dosages are sufficient to enhance or direct neurite outgrowth, and will vary with the method of administration and the condition to be treated.

Antibodies may also be used as a "biological glue," as described above to bind multiple cadherin-expressing cells within a variety of contexts, such as to enhance wound healing and/or reduce scar tissue, and/or to facilitate cell adhesion in skin grafting or prosthetic implants. In general, the amount of matrix-linked antibody administered to a wound, graft or implant site varies with the severity of the wound and/or the nature of the wound, graft, or implant, but may vary as discussed above. Antibodies may also be linked to any of a variety of support materials, as described above, for use in tissue culture or bioreactors.

Antibodies (or, preferably, antigen-binding fragments thereof) may also be used in situations where inhibition of cell adhesion is desired. Such antibodies or fragments may be used, for example, for treatment of demyelinating diseases, such as multiple sclerosis (MS), or to inhibit interactions between tumor cells, as described above. The use of Fab fragments is generally preferred.

Evaluation of Modulating Agent Activity

As noted above, the modulating agent of the present invention specifically binds to a classical cadherin and modulates a cadherin-mediated response. The ability to bind to a cadherin sequence may generally be evaluated using any binding assay known to those of ordinary skill in the art. For example, a Pharmacia Biosensor machine may be used, as discussed in Jonsson et al., *Biotechniques* 11:520-27, 1991. A specific example of the technology that measures the interaction of peptides with molecules can be found in Williams et al., *J. Biol. Chem.* 272:8539-8545, 1997. Real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule (for example, fc-E-cad; referred to as the ligand) to the surface of a Biosensor chip, followed by binding of the interacting molecule (referred to as the analyte) to the ligand. Binding to the chip is measured in real-time in arbitrary units of resonance (RU).

For example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 µg/ml) in 10 mM Sodium Acetate, pH 4.0, according to the manufacturer's protocol. Approximately 2100-2600 resonance units (RU) of target protein/ligand (for example, fc-E-cadherin) may be immobilized, corresponding to a concentration of about 2.1-2.6 ng/mm$^2$. Any non-specifically bound target protein is removed. To determine binding, test analytes (e.g., peptides) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds a classical cadherin at a detectable level within such as assay.

An alternative method may also be used to detect specific binding of a modulating agent and a classical cadherin. In this method, E-cadherin molecules are used to coat a plate. The resulting plate is then contacted by E-cadherin-expressing cancer cells. The interaction between the E-cadherin coated on the plate and the E-cadherin expressed on the surface of cancer cells allows the cancer cells to stick to the plate during washing processes. Such interaction may be disrupted or interfered by a candidate modulating agent subsequently added to the plate. By measuring the number of the cells still attached to the plate or dissociated from the plate, the affinity between the candidate modulating agent and E-cadherin may be determined. In certain embodiments, a candidate modulating agent may be added to the plate at the same time as E-cadherin expressing cancer cells, and the ability of the candidate modulating agent to bind E-cadherin may be determined by comparing the number of cancer cells stricken to the plate in the presence of the candidate modulating agent and that in the absence of the candidate modulating agent.

The ability to modulate a cadherin-mediated function may be evaluated using any of a variety of in vitro assays designed to measure the effect of the peptide on a typical cadherin response. As noted above, modulating agents may be capable of enhancing or inhibiting a cadherin-mediated function. The ability of an agent to modulate cell adhesion may generally be evaluated in vitro by assaying the effect on one or more of the following: (1) neurite outgrowth, (2) Schwann cell-astrocyte adhesion, (3) Schwann cell migration on astrocyte monolayers, (4) adhesion between endothelial cells, (5) adhesion between epithelial cells (e.g., normal rat kidney cells and/or human skin) and/or (6) adhesion between cancer cells. In general, a modulating agent is an inhibitor of cell adhesion if, within one or more of these representative assays, contact of the test cells with the modulating agent results in a discernible disruption of cell adhesion. Modulating agents that enhance cell adhesion (e.g., agents comprising multiple Trp-containing CAR sequences and/or linked to a support material) are considered to be modulators of cell adhesion if they are capable of enhancing neurite outgrowth as described below or are capable of promoting cell adhesion, as judged by plating assays to assess epithelial cell adhesion to a modulating agent attached to a support material, such as tissue culture plastic.

Within a representative neurite outgrowth assay, neurons may be cultured on a monolayer of cells (e.g., 3T3 fibroblasts) that express N-cadherin. Neurons grown on such cells (under suitable conditions and for a sufficient period of time) extend neurites that are typically, on average, twice as long as neurites extended from neurons cultured on 3T3 cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49-55, 1994; Williams et al., *Neuron* 13:583-594, 1994; Hall et al., *Cell Adhesion and Commun.* 3:441-450, 1996; Doherty and Walsh, *Mol. Cell. Neurosci.* 8:99-111, 1994; and Safell et al., *Neuron* 18:231-242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent that modulates N-cadherin-mediated cell adhesion may inhibit or enhance such neurite outgrowth. Under the conditions described above, the presence of 500 µg/mL of a modulating agent that disrupts neural cell adhesion should result in a decrease in the mean neurite length by at least 50%, relative to the length in the absence of modulating agent or in the presence of a negative control peptide. Alternatively, the presence of 10 µg/mL of a modulating agent that enhances neural cell adhesion should result in an increase in the mean neurite length by at least 50%. Certain peptides having N-cadherin agonist activity have been described (e.g., Williams et al., Dimeric versions of two short N-cadherin binding motifs (HAVDI and INPISG) function as N-cadherin agonists. *J Biol Chem* 277: 4361-4367, 2002).

The effect of a modulating agent on Schwann cell adhesion to astrocytes may generally be evaluated using a cell adhesion assay. Briefly, Schwann cells fluorescently labeled with Di-I may be plated onto an astrocytic surface (e.g., a glass coverslip coated with a monolayer of astrocytes) and incubated on a shaking platform (e.g., 25 rpm for 30 minutes) in the presence and absence of modulating agent at a concentration of approximately 1 mg/mL. Cells may then be washed (e.g., in Hanks medium) to remove non-attached cells. The attached cells may then be fixed and counted (e.g., using a fluorescent microscope). In general, 1 mg/mL of a modulating agent results in a decrease in cell adhesion of at least 50%. This assay evaluates the effect of a modulating agent on N-cadherin mediated cell adhesion.

Schwann cell migration may generally be evaluated using a micro-inverted-coverslip assay. In this assay, a dense Schwann cell culture is established on coverslip fragments and Schwann cell migration away from the fragment edge is measured. Briefly, Schwann cells fluorescently labeled with Di-I may be plated on polylysine- and laminin-coated fragments of a glass coverslip and allowed to bind to the surface for 16-18 hours. Cells may then be washed (e.g., in Hanks medium) to remove non-attached cells, and then inverted, with cells facing downward onto an astrocyte-coated surface. Cultures are then incubated further for 2 days in the presence or absence of modulating agent at a concentration of approximately 1 mg/mL and fixed. The maximum migration distance from the edge of the coverslip fragment may then be measured. At a level of 1 mg/mL, a modulating agent results in an increase or decrease in the maximum migration distance of at least 50%. This assay evaluates the effect of a modulating agent on N-cadherin mediated cell adhesion.

Within certain cell adhesion assays, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (e.g., Blaschuk and Farookhi, *Dev. Biol.* 136:564-567, 1989). Cadherin-expressing cells include endothelial, epithelial and/or cancer cells. For example, such cells may be plated under standard conditions that, in the absence of modulating agent, permit cell adhesion. In the presence of modulating agent (e.g., 500 μg/mL), disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/$cm^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 μg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC #1571-CRL) may be plated at 10-20,000 cells per 35 mm tissue culture flasks containing DMEM with 10% FCS and subcultured periodically (Laird et al., *J. Cell Biol.* 131:1193-1203, 1995). Cells may be harvested and replated in 35 mm tissue culture flasks containing 1 mm coverslips and incubated until 50-65% confluent (24-36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., *J. Cell Biol.* 131:1193-1203, 1995), of at least 75% within 48 hours.

Another cell adhesion assay involves evaluating the effect of a modulating agent on permeability of adherent epithelial and/or endothelial cell layers. For example, the effect of permeability on human skin may be evaluated. Such skin may be derived from a natural source or may be synthetic. Human abdominal skin for use in such assays may generally be obtained from humans at autopsy within 24 hours of death. Briefly, a modulating agent (e.g., 500 μg/ml) and a test marker (e.g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, *Curr. Prob. Dermatol.* 7:58-68, 1978; Franz, *J. Invest. Dermatol.* 64:190-195, 1975). The penetration of the markers through the skin may be assessed at, for example, 6, 12, 24, 36, and 48 hours after the start of the experiment. In general, a modulating agent that enhances the permeability of human skin results in a statistically significant increase in the amount of marker in the receptor compartment after 6-48 hours in the presence of 500 μg/mL modulating agent. This assay evaluates the effect of a modulating agent on E-cadherin mediated cell adhesion.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support material, such as a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., HAV, RGD or LYHY (SEQ ID NO: 148)) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects, the present invention also provides compositions (e.g., pharmaceutical compositions) comprising one or more modulating agents as described herein. An exemplary composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a composition of the present invention may further comprise a modulator of cell adhesion that is mediated by one or more molecules other than cadherins. Such modulators may generally be prepared as described above, incorporating one or more non-cadherin CAR sequences and/or antibodies thereto in place of Trp-containing CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., Dsg and Dsc); integrins; members of the immunoglobulin supergene family, such as N-CAM and JAM; and other transmembrane proteins, such as occludin and claudins, as well as extracellular matrix proteins such as laminin, fibronectin, collagens, vitronectin, entactin and tenascin. Preferred CAR sequences for use within such a modulator include HAV, RGD, YIGSR (SEQ ID NO: 145), KYSFNYDGSE (SEQ ID NO: 146), a Dsc or Dsg CAR sequence, a claudin CAR sequence, a JAM CAR sequence, a claudin CAR sequence and/or the occludin CAR sequence LYHY (SEQ ID NO: 148).

A composition of the present invention may also, or alternatively, contain one or more pharmaceutically active substances, which may be linked to a modulating agent or may be free within the composition. A "pharmaceutically active substance" (used interchangeably with "drug") is a compound or composition useful in treating and/or preventing a disease or disorder. Virtually any pharmaceutically active substance may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a composition of the present invention, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Compositions of the present invention may be administered in a manner appropriate to the disease or disorder to be treated (or prevented). Appropriate dosages and a suitable duration and frequency of administration will be determined by such factors as the condition of the patient, the type and severity of the patient's disease or disorder and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 μg to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Therapeutic Methods Employing Modulating Agents

In general, the modulating agents and compositions described herein may be used for modulating the adhesion of cadherin-expressing cells (i.e., cells that express one or more of E-cadherin, N-cadherin, P-cadherin, R-cadherin and/or other cadherin(s), including as yet undiscovered cadherins). Such modulation may be performed in vitro and/or in vivo, preferably in a mammal such as a human. As noted above, modulating agents for purposes that involve the disruption of cadherin-mediated cell adhesion may comprise a Trp-containing CAR sequence, multiple Trp-containing CAR sequences in close proximity and/or an antibody (or an antigen-binding fragment thereof) that recognizes a Trp-containing CAR sequence. When it is desirable to also disrupt cell adhesion mediated by other adhesion molecules, a modulating agent may additionally comprise one or more CAR sequences (other than a Trp-containing CAR sequence) bound by such adhesion molecules (and/or antibodies or fragments thereof that bind such sequences), preferably separated from each other and from the Trp-containing CAR sequence by linkers. As noted above, such linkers may or may not comprise one or more amino acids. For enhancing cell adhesion, a modulating agent may contain multiple Trp-containing CAR sequences or antibodies (or fragments), preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of cadherin-expressing cells. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

In general, within methods for modulating cell adhesion, a cadherin-expressing cell is contacted with a modulating agent under conditions and for a time sufficient to permit inhibition or enhancement of a cadherin-mediated function. Cadherin-expressing cells include, but are not limited to, epithelial cells, endothelial cells, neural cells, tumor cells and lymphocytes. Such contact may be achieved in vitro, or in vivo by administration of a pharmaceutical composition as provided herein.

Within certain aspects, methods are provided in which cell adhesion is diminished. In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), <u>DWVIPP</u> (SEQ ID NO: 3), <u>DWVVAP</u> (SEQ ID NO: 12), or <u>EWVMPP</u> (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. Preferably, such sequences are separated from the Trp-containing CAR sequence via a linker. Alternatively, a separate modulator of cell adhesion (e.g., integrin- and/or occludin-mediated) may be administered in conjunction with the modulating agent(s), either within the same pharmaceutical composition or separately. Additional embodiments may employ antibody or Fab fragments directed against these or other CAR sequences.

Topical administration of the modulating agent(s) is generally preferred, but other means may also be employed.

Preferably, a fluid composition for topical administration (comprising, for example, physiological saline) comprises an amount of modulating agent as described above, and more preferably from 10 μg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within another such aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomemic of one of the foregoing sequences. In addition, a modulating agent may comprise the sequence RGD, which is bound by integrins, the sequence LYHY (SEQ ID NO: 148), which is bound by occludin, a JAM CAR sequence, a Dsg CAR sequence, a Dsc CAR sequence, a claudin CAR sequence and/or one or more of HAV and/or a non-classical cadherin CAR sequence. Preferably, such sequences are separated from the Trp-containing CAR sequence via a linker. Alternatively, a separate modulator of cell adhesion (e.g., Dsg- and/or Dsc- and/or integrin- and/or occludin-mediated) may be administered in conjunction with the modulating agent(s), either within the same pharmaceutical composition or separately. Additional embodiments may employ antibody or Fab fragments directed against these or other CAR sequences.

Contact may be achieved by direct application of the modulating agent, generally within a composition formulated as a cream or gel, or using any of a variety of skin contact devices for transdermal application (such as those described in European Patent Application No. 566,816A; U.S. Pat. Nos. 5,613,958; 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin that is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provides a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, the use of modulating agents as described herein to increase the permeability of endothelial and epithelial cell layers, thereby facilitating sampling of the blood compartment by passive diffusion. Such methods permit the detection and/or measurement of the levels of specific molecules circulating in the blood. In general, to sample the blood compartment, it is necessary to perturb adhesion between the epithelial cells (keratinocytes) and the endothelial cells of the microvasculature. Using currently available techniques, only small, uncharged molecules may be detected across skin in vivo. The methods described herein are not subject to the same degree of limitation. Accordingly, a wide variety of blood components may be sampled across epithelial and endothelial cell layers. Such sampling may be achieved across any such cell layers, including skin and gums.

For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

To facilitate sampling of blood in a patient, a modulating agent as described herein is contacted with the skin surface. Multifunctional modulating agents comprising a Trp-containing CAR sequence linked to one or more of the classical cadherin CAR sequence HAV, a non-classical cadherin CAR sequence, the occludin CAR sequence LYHY (SEQ ID NO: 148), a claudin CAR sequence, the Dsc and/or Dsg CAR sequences may also be used to disrupt epithelial cell adhesion. Such modulating agents may also, or alternatively, comprise the fibronectin CAR sequence RGD, which is recognized by integrins, and a JAM CAR sequence. Additional embodiments may employ antibody or Fab fragments directed against these or other CAR sequences. Alternatively, a separate modulator of non-classical cadherin-mediated cell adhesion may be administered in conjunction with the modulating agent(s), either within the same pharmaceutical composition or separately.

Contact may be achieved as described herein for transdermal drug delivery. Modulating agent(s) and reagents for assaying blood components may, but need not, be contained within the same composition or skin patch. In general, the amount of modulating agent administered via the skin may vary as described above. Such levels may be achieved by appropriate adjustments to the device used, or by applying a cream formulated as described above. Transfer of the blood component across the skin may be predicted based on in vitro studies using, for example, a Franz cell apparatus, and evaluated in vivo by appropriate means that will be apparent to those of ordinary skill in the art.

Kits for sampling blood component via, for example, the skin or gums of a mammal, are also provided within the present invention. Such kits generally comprise a device for transdermal application (i.e., skin patch) in combination with, or impregnated with, one or more modulating agents. A reagent for detection of a blood component may additionally be included within such kits.

Within another related aspect, methods are provided for enhancing delivery of inhaled compounds (e.g., drugs) in a mammal, comprising contacting lung epithelial cells of a mammal with a cell adhesion modulating agent that inhibits cadherin-mediated cell adhesion. Lung is another site for the delivery of drugs, which provide rapid absorption, especially for the delivery of high molecular weight pharmaceutical agents (see, U.S. Pat. No. 6,294,153). The delivery of drugs may be further facilitated by the use of cell adhesion modulating agent that inhibits cadherin-mediated cell adhesion.

To enhance the delivery of an inhaled compound, a modulating agent as described herein and an inhaled compound are contacted with lung epithelial cells. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence, a Dsg CAR sequence, a Dsc CAR sequence and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately. Additional embodiments may employ antibody or Fab fragments directed against these or other CAR sequences.

Contact of a cell adhesion modulating agent with lung epithelial cells may be achieved by a device such as an inhaler, a nebulizer or the like. The modulating agent and the compound to be inhaled may be contained within the same composition and administered together. Alternatively, they may be separately administered, although administration at the same time is preferred. In general, the amount of modulating agent administrated via the lung varies with the nature of the condition to be treated or prevented, but may vary. Such levels may be achieved by appropriate adjustment to the device used. Transfer of the drug to the lung may be evaluated by appropriate means that will be apparent to those of ordinary skill in the art, such as monitoring the serum level of the administered drug.

Similar to the enhanced transdermal drug delivery, a wide variety of drugs may be administered according to the methods provided herein. Exemplary drugs include: heparin, hirulog, hirugen, huridine, interferons, interleukins, cytokines, antibodies, immunoglobulins, chemotherapeutic agents, vaccines, glycoproteins, bacterial toxoids, calcitonins, hormones (e.g., insulin), DNA, RNA, antisense oligonucleotides, narcotics, hypnotics, steroids and non-steroidal anti-inflammatory drugs.

Within a further aspect, methods are provided for enhancing delivery of a drug to a tumor in a mammal, comprising administering a modulating agent in combination with a drug to a tumor-bearing mammal. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), <u>DWVIPP</u> (SEQ ID NO: 3), <u>DWVVAP</u> (SEQ ID NO: 12), or <u>EWVMPP</u> (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence, a Dsc CAR sequence, a Dsc CAR sequence, and/or one or more of HAV and/or a non-classical cadherin CAR sequence. Preferably, such sequences are separated from the Trp-containing CAR sequence via a linker. Alternatively, a separate modulator of cell adhesion (e.g., integrin- and/or occludin-mediated) may be administered in conjunction with the modulating agent(s), either within the same pharmaceutical composition or separately. Additional embodiments may employ antibody or Fab fragments directed against these or other CAR sequences.

In another preferred embodiment, a modulating agent is capable of disrupting cell adhesion mediated by multiple adhesion molecules. For example, a single branched modulating agent (or multiple agents linked to a single molecule or support material) may disrupt E-cadherin, N-cadherin, occludin, claudin, JAM, Dsc and Dsg mediated cell adhesion, thereby disrupting adherens junctions, tight junctions and desmosomes. Such an agent may comprise one or more of the Trp-containing CAR sequence, as well as a Dsg and/or Dsc CAR sequence; a JAM CAR sequence; a claudin CAR sequence; the OB-cadherin CAR sequence DDK; the occludin CAR sequence LYHY; and/or one or more of HAV and/or a non-classical cadherin CAR sequences. Such agents serve as multifunctional disrupters of cell adhesion. Alternatively, a separate modulator of non-classical cadherin-mediated cell adhesion may be administered in conjunction with the modulating agent(s), either within the same pharmaceutical composition or separately. Preferred antibody modulating agents include Fab fragments directed against a Trp-containing CAR sequence from a N-cadherin or an E-cadherin. Fab fragments directed against the occludin CAR sequence GVNPTAQSSGSLYGSQIYALCNQFYT-PAATGLYVDQYLYHYCVVDPQE (SEQ ID NO: 160) may also be employed, either incorporated into a modulating agent or within a separate modulator that is administered concurrently. Additional embodiments may employ antibody or Fab fragments directed against these or other CAR sequences.

Preferably, the modulating agent and the drug are formulated within the same composition or drug delivery device prior to administration. In general, a modulating agent may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 1 μg/mL to about 2 mg/mL, and more preferably from about 10 μg/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting (lessening or reducing) cancer metastasis in a mammal. Cancer tumors are solid masses of cells, growing out of control, which require nourishment via blood vessels. The formation of new capillaries is a prerequisite for tumor growth and the emergence of metastases. Administration of modulating agents as described herein may disrupt the growth of such blood vessels, thereby providing effective therapy for the cancer (e.g., reduce or inhibit cancer progression, including tumor growth) and/or inhibiting metastasis. Cancer metastasis refers to a multi-step process that comprises cancer cell invasion (i.e., penetration of cancer cells through the barriers that separate cancer cells from healthy tissues and blood vessels), dispersal of small clumps of tumor cells to other organs or parts of the body, and the growth of secondary tumors in those sites. Modulating agents may also be used to treat leukemias.

Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence (e.g. DDK). Preferably, such sequences are separated from the Trp-containing CAR sequence via a linker. and/or one or more of HAV and/or a non-classical cadherin CAR sequence. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as the level of serum tumor markers (e.g., CEA or PSA).

In yet another related aspect, the present invention provides methods for modulating (enhancing, inducing, inhibiting or reducing) apoptosis in a cadherin-expressing cell. In general, patients afflicted with cancer may benefit from the treatment of a modulating agent that induces or enhances apoptosis whereas a modulating agent that inhibits or reduces apoptosis may be used to prevent cell deaths (such as neuron death caused by lack of blood flowing to the brain as a result of stroke). Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence, a Dsg CAR sequence, a Dsc CAR sequence, and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

Within a further related aspect, a modulating agent may be used to inhibit (i.e., reduce or lessen) angiogenesis (i.e., the growth of blood vessels from pre-existing blood vessels) in a mammal. Inhibition of angiogenesis may be beneficial, for example, in patients afflicted with diseases such as cancer or arthritis. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327-343, 1995). Briefly, a modulating agent may be embedded in a mesh composed of vitrogen at one or more concentrations (e.g., ranging from about 1 to 100 µg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 33 µg/mesh.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In another embodiment, methods are provided for causing the regression of blood vessels for the treatment of conditions such as cancer, psoriasis, arthritis, and age-related macular degeneration. Cancer tumors are solid masses of cells, growing out of control, which require nourishment via blood vessels. The formation of new capillaries is a prerequisite for tumor growth and the emergence of metastases. Administration of the modulating agents described herein may disrupt blood vessels and cause them to regress, thereby providing effective therapy for patients afflicted with diseases such as cancer. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

Administration may be topical, via injection or by other means, and the addition of a targeting agent may be beneficial, particularly when the administration is systemic. Suitable modes of administration and dosages depend upon the location and nature of the endothelial cells and/or pericytes for which disruption of cell adhesion is desired but, in general, dosages may vary as described above. The addition of a targeting agent may be beneficial, particularly when the administration is systemic. Suitable modes of administration and dosages depend upon the condition to be prevented or treated but, in general, administration by injection is appropriate. Dosages may vary as described above.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately. Preferably, the peptide portion(s) of such modulating agents comprise 6-16 amino acids. Modulating agents may further comprise antibodies or Fab fragments directed against an N-cadherin Trp-containing sequence. Fab fragments directed against the occludin CAR sequence GVNPTAQSSGSLYGSQIYALCNQFYT-PAATGLYVDQYLYH-YCVVDPQE (SEQ ID NO: 160) may also be employed, either incorporated into the modulating agent or administered concurrently as a separate modulator.

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

Within one aspect, the present invention provides methods for reducing aggregation of cultured cells (e.g., cultured stem cells) by contacting the cells with a cell adhesion modulating agent that inhibits cadherin-mediated cell adhesion. Stem cell therapy offers an opportunity to treat many degenerative diseases caused by the premature death of malfunction of specific cell types and the body's failure to replace or restore them. Possible therapeutic uses of stem cells include immunological conditioning of patients for organ transplants, treatment of autoimmune diseases such as muscular dystrophy, multiple sclerosis and rheumatoid arthritis, repair of damaged tissues such as stroke, spinal injury and burn, treatment of neurodegenerative disease like Lou Gehrig's disease, and neurological conditions such as Parkinson's Huntington's and Alzheimer's diseases, treatment of leukaemia, sickle cell anaemia, heart disease, and diabetes. For most stem cell therapy, embryonic stem cells or adult stem cells may be cultured in vitro, induced to differentiate to the desired cell type and transplant to a patient. For successful culture of stem cells, aggregation among these cells needs to be minimized.

To reduce aggregation of stem cells, a modulating agent as described herein may be used. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence, a Dsg CAR sequence, a Dsc CAR sequence, and/or one or more of HAV and/or a non-classical cadherin CAR sequence. and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

The modulating agent of the present invention may be used at various stages of stem cell culture. For instance, it may be used to reduce cell adhesion of stem cells when they are isolated from their source tissue. Alternatively, it may be added to culture media when excessive cell aggregation occurs. It may also be continuously present in culture media to minimize cell aggregation. The concentration of the modulating agent may be optimized by adjusting the amount of the modulating agent to the level at which cell aggregation is reduced with respect to cultured stem cells in the absence of the modulating agent, and other aspects of the cell culture (e.g., cell viability rate and cell reproduction rate) is not adversely affected.

Although the above description focuses on the reduction of stem cell aggregation using the modulating agents of the present invention, one of ordinary skill in the art appreciates that such agents may be used in in vitro culture of other types of animal cells to minimize cell aggregation.

In certain other aspects, the present invention provides methods for enhancing adhesion of cadherin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising an RGD sequence may be attached to the same matrix, preferably in an alternating pattern). Such matrices may be used in contexts in which it is desirable to enhance adhesion mediated by multiple cell adhesion molecules. Alternatively, the modulating agent itself may comprise multiple Trp-containing sequences or antibodies (or fragments thereof), separated by linkers as described above. Either way, the modulating agent(s) function as a "biological glue" to bind multiple cadherin-expressing cells within a variety of contexts.

Within one aspect, such modulating agents may be used to enhance wound healing and/or reduce scar tissue in a mammal. Peptides that may be linked to a support, and/or to one another via a linker, to generate a suitable modulating agent include, but are not limited to, those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a derivative of one of the foregoing sequences. Modulating agents that are linked to a biocompatible and biodegradable matrix such as cellulose or collagen are particularly preferred. For use within such methods, a modulating agent should have a free amino or hydroxyl group. Multi-functional modulating agents comprising the Trp-containing sequence, the fibronectin CAR sequence RGD, which is recognized by integrins, the OB-cadherin CAR sequence DDK, a JAM CAR sequence and/or a Dsc or Dsg CAR sequence may also be used as potent stimulators of wound healing and/or to reduce scar tissue. Such agents may also, or alternatively, comprise the occludin CAR sequence LYHY (SEQ ID NO: 148) and/or a claudin CAR sequence. Additional embodiments may employ antibody or Fab fragments directed against these or other CAR sequences. Alternatively, one or more separate modulators of integrin-, Dsc-, Dsg-, claudin- and/or occludin-mediated cell adhesion may be administered in conjunction with the modulating agent(s), either within the same pharmaceutical composition or separately. and/or one or more of HAV and/or a non-classical cadherin CAR sequence.

The modulating agents are generally administered topically to the wound, where they may facilitate closure of the wound and may augment, or even replace, stitches. Similarly, administration of matrix-linked modulating agents may facilitate cell adhesion in foreign tissue implants (e.g., skin grafting and prosthetic implants) and may prolong the duration and usefulness of collagen injection. In general, the amount of matrix-linked modulating agent administered to a wound, graft or implant site varies with the severity of the wound and/or the nature of the wound, graft, or implant, but may vary as discussed above.

Within another aspect, one or more modulating agents (antibodies and/or Fab fragments against these sequences) may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

The present invention also provides, within further aspects, methods for enhancing and/or directing neurological growth. In one such aspect, neurite outgrowth may be enhanced and/or directed by contacting a neuron with one or more modulating agents. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins and/or one or more of HAV and/or a non-classical cadherin CAR sequence and/or an NCAM CAR sequence and or an antibody or Fab fragments directed against these or other CAR sequences. Preferably, such sequences are separated from the Trp-containing CAR sequence via a linker. Alternatively, a separate modulator of cell adhesion (e.g., integrin-mediated modulators) may be administered in conjunction with the modulating agent(s), either within the same pharmaceutical composition or separately.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

Within another aspect, one or more modulating agents may be used for therapy of a demyelinating neurological disease in a mammal. There are a number of demyelinating diseases, such as multiple sclerosis, characterized by oligodendrocyte death. Since Schwann cell migration on astrocytes is inhibited by N-cadherin, modulating agents that disrupt N-cadherin mediated cell adhesion as described herein, when implanted with Schwann cells into the central nervous system, may facilitate Schwann cell migration and permit the practice of Schwann cell replacement therapy.

Multiple sclerosis patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise one or more of a N-CAM CAR sequence, a classical cadherin CAR sequence HAV and/or a non-classical cadherin CAR sequence and or an antibody or Fab fragments directed against these or other CAR sequences. Preferably, such sequences are separated from the Trp-containing CAR sequence via a linker. Alternatively, a separate modulator of cell adhesion (e.g., non-classical cadherin-mediated) may be administered in conjunction with the modulating agent(s), either within the same pharmaceutical composition or separately.

Preferred separate modulators of cell adhesion may include, for example, antibodies or Fab fragments directed against cadherin CAR sequences, such as the N-cadherin CAR sequence or Fab fragments directed against neuronal cell adhesion molecule (N-CAM) CAR sequence. Such antibodies and fragments can be prepared using standard techniques, as discussed above. Suitable amounts of modulating agent generally range as described above, preferably from about 10 µg/mL to about 1 mg/mL.

Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453-55, 1993; Baron-Van Evercooren et al., *Glia* 16:147-64, 1996). OPs can be isolated using routine techniques known in the art (see e.g., Milner and French-Constant, *Development* 120:3497-3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS.

OPs can be expanded in vitro if cultured as "homotypic aggregates" or "spheres" (Avellana-Adalid et al, *J. Neurosci. Res.* 45:558-70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al, *J. Neurosci. Res.* 45:558-70, 1996).

An alternative source of OP may be spheres derived from CNS stem cells. Recently, Reynolds and Weiss, *Dev. Biol.* 165:1-13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1-13, 1996). Spheres derived from CNS stem cells provide an alternative source of OP that may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy.

Neurosphere grafts may be implanted directly into the central nervous system along with the modulating agent(s) using standard techniques. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise one or more of a N-CAM CAR sequence, classical cadherin CAR sequence HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., non-classical cadherin-mediated) may be administered in conjunction with the modulating agent(s), either within the same pharmaceutical composition or separately.

Preferred separate modulators of cell adhesion may include, for example, antibodies or Fab fragments directed against cadherin CAR sequences, such as the N-CAD CAR sequence LRAHAVDING and/or antibodies or Fab fragments directed against neuronal cell adhesion molecule (N-CAM) CAR sequences. Such antibodies and fragments can be prepared using standard techniques, as discussed above. Suitable amounts of modulating agent generally range as described above, preferably from about 10 μg/mL to about 1 mg/mL. Modulating agents comprising one or more of these sequences (or analogues or peptidomimetics thereof) are also preferred. Preferred antibody modulating agents include Fab fragments directed against an N-cadherin Trp-containing CAR sequence. Such antibodies and fragments can be prepared using standard techniques, as discussed above. Suitable amounts of modulating agent generally range as described above, preferably from about 10 μg/mL to about 1 mg/mL.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the modulating agent or pharmaceutical composition may be administered at a dosage ranging from 0.1 mg/kg to 20 mg/kg although appropriate dosages may be determined by clinical trials. Methods of administration include injection, intravenous or intrathecal (i.e., directly in cerebrospinal fluid). A modulating agent or pharmaceutical composition may further comprise a drug (e.g., an immunomodulatory drug).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573-79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

Within a related aspect, the present invention provides methods for facilitating migration of an N-cadherin expressing cell on astrocytes. The modulating agents of the present invention may be used to contact an N-cadherin expressing cell and one or more astrocytes. Preferred N-cadherin expressing cells include Schwann cells, oligodendrocytes and oligodendrocyte progenitor cells. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise one or more of HAV and/or a non-classical cadherin CAR sequence. Preferably, such sequences are separated from the Trp-containing CAR sequence via a linker. Alternatively, a separate modulator of cell adhesion (e.g., non-classical cadherin-mediated) may be administered in conjunction with the modulating agent(s), either within the same pharmaceutical composition or separately.

Preferred separate modulators of cell adhesion can include, for example, antibodies or Fab fragments directed against Trp containing peptides described herein and/or cadherin CAR sequences, such as the N-cadherin CAR sequence LRA-HAVDING. Such antibodies and fragments can be prepared using standard techniques, as discussed above. Suitable amounts of modulating agent generally range as described above, preferably from about 10 μg/mL to about 1 mg/mL.

Within further aspects, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies (see Lee et al., *J. Immunol.* 152:5653-5659, 1994; Munro et al., *Cellular Immunol.* 169:309-312, 1996; Tsutsui et al., *J. Biochem.* 120:1034-1039, 1996; Cepek et al., *Proc. Natl. Acad. Sci. USA* 93:6567-6571, 1996). Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-Tcells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a modulating agent. Such treatment may also benefit patients undergoing transplantation with peripheral blood stem cells.

Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of the classical cadherin CAR sequence HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

Within the above methods, the modulating agent(s) are preferably administered systemically (usually by injection) or topically. A modulating agent may be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages generally range as described above.

Within further aspects, the present invention provides methods and kits for preventing pregnancy in a mammal. In general, disruption of E-cadherin function prevents the adhesion of trophoblasts and their subsequent fusion to form syncitiotrophoblasts. In one embodiment, one or more modulating agents as described herein may be incorporated into any of a variety of well-known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

Suitable methods for incorporation into a contraceptive device depend upon the type of device and are well known in the art. Such devices facilitate administration of the modulating agent(s) to the uterine region and may provide a sustained release of the modulating agent(s). In general, modulating agent(s) may be administered via such a contraceptive device at a dosage ranging from 0.1 to 50 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more modulating agents.

Alternatively, a sustained release formulation of one or more modulating agents may be implanted, typically subdermally, in a mammal for the prevention of pregnancy. Such implantation may be performed using well-known techniques. Preferably, the implanted formulation provides a dosage as described above, although the minimum effective dosage may be determined by those of ordinary skill in the art using, for example, an evaluation of hCG levels in the urine of women.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability. Accordingly, modulating agents as described herein that decrease N-cadherin mediated adhesion may be used to increase vascular permeability. Preferred modulating agents for use within such methods include those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. For example, a modulating agent may further comprise an E-cadherin HAV sequence. Alternatively, separate modulating agents capable of disrupting N— and E-cadherin mediated adhesion may be administered concurrently.

In one particularly preferred embodiment, a modulating agent is further capable of disrupting cell adhesion mediated by multiple adhesion molecules. Such an agent may comprise a Trp-containing CAR sequence, as well as an RGD sequence, a Dsc CAR sequence, a Dsg CAR sequence, a claudin CAR sequence, a JAM CAR sequence, and/or one or more of HAV and/or a non-classical cadherin CAR sequence, and/or the occludin CAR sequence LYHY. Additional embodiments may employ antibody or Fab fragments directed against these or other CAR sequences. Alternatively, a separate modulator cell adhesion that comprises a CAR sequence other than a Trp-containing sequence may be administered in conjunction with the modulating agent(s), either within the same pharmaceutical composition or separately.

Treatment with the modulating agents provided herein may serve to increase blood flow to a tumor. Such treatment may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within further aspects, the present invention provides methods for disrupting neovasculature (i.e., newly formed blood vessels). Such methods may be used to disrupt normal or pathological neovasculature in a variety of contexts. Disruption of neovasculature is therapeutic for conditions in which the presence of newly formed blood vessels is related to the underlying disorder, its symptoms or its complications. For example, disorders that may be treated include, but are not limited to, benign prostatic hyperplasia, diabetic retinopathy, vascular restenosis, arteriovenous malformations, meningioma, hemangioma, neovascular glaucoma, psoriasis, angiofiboma, arthritis, atherosclerotic plaques, corneal graft neovascularization, hemophilic joints, hypertrophic scars, hemorrhagic telangiectasia, pyogenic granuloma, retrolental fibroplasias, scleroderma trachoma, vascular adhesions, synovitis, dermatitis, endometriosis, macular degeneration and exudative macular degeneration. Preferred modulating agents for use within such methods include those comprising one or more of the D/E-W-V-IV/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP(SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately.

Within a further aspect, modulating agents as described herein may be used for controlled inhibition (i.e., reduction) of synaptic stability, resulting in increased synaptic plasticity. Within this aspect, administration of one or more modulating agents may be advantageous for repair processes within the brain, as well as learning and memory, in which neural plasticity is a key early event in the remodeling of synapses. Cell adhesion molecules, particularly N-cadherin and E-cadherin, can function to stabilize synapses, and loss of this function is thought to be the initial step in the remodeling of the synapse that is associated with learning and memory (Doherty et al., *J. Neurobiology,* 26:437-446, 1995; Martin and Kandel, *Neuron,* 17:567-570, 1996; Fannon and Colman, *Neuron,* 17:423-434, 1996). Inhibition of cadherin function by administration of one or more modulating agents that inhibit cadherin function may stimulate learning and memory. Preferred modulating agents for use within such methods include those that disrupt E-cadherin and/or N-cadherin mediated cell adhesion, such as those comprising one or more of the D/E-W-V-I/V/M-P/A-P (SEQ ID NO: 168) sequences (e.g., DWVIPP (SEQ ID NO: 3), DWVVAP (SEQ ID NO: 12), EWVMPP (SEQ ID NO: 23), DWVIPP (SEQ ID NO: 3), DWVVAP (SEQ ID NO: 12), or EWVMPP (SEQ ID NO: 23) in which cyclization is indicated by an underline). Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 148), which is bound by occludin, a JAM CAR sequence, a claudin CAR sequence and/or one or more of HAV and/or a non-classical cadherin CAR sequence. Preferably, such sequences are separated from the Trp-containing CAR sequence via a linker. Additional embodiments may employ antibody or Fab fragments directed against these or other CAR sequences. Alternatively, a separate modulator of cell adhesion (e.g., integrin- and/or occludin-mediated) may be administered in conjunction with the modulating agent(s), either within the same pharmaceutical composition or separately. For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

Assays Employing Antibodies that Specifically Bind to Trp-Containing CAR Sequences Other aspects of the present invention provide methods that employ antibodies raised against a Trp-containing CAR sequence for diagnostic and assay purposes. Such polyclonal and monoclonal antibodies may be raised against a peptide using conventional techniques and as described above. Assays employing antibodies typically involve using an antibody to detect the presence or absence of a cadherin (free or on the surface of a cell), or proteolytic fragment containing the EC1 or EC4 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual,* Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment thereof, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody and, as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of a cadherin in a sample is a two-antibody sandwich assay. This assay may be performed by first contacting an antibody that has been immobilized on a solid support, commonly the well of a microtiter plate, with the biological sample, such that the cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well-known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing different cadherins (or different cadherin levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating cadherin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate cadherin-mediated cell adhesion.

Identification of Compounds that Bind to Trp-Containing CAR Sequences

The present invention further provides methods for identifying compounds that bind to a Trp-containing CAR sequence. Such agents may generally be identified by contacting a polypeptide as provided herein with a candidate compound or agent under conditions and for a time sufficient to allow interaction with a polypeptide comprising a Trp-containing CAR sequence. Any of a variety of well-known binding assays may then be performed to assess the ability of the candidate compound to bind to the polypeptide. In general, a candidate compound that binds to the polypeptide at a significantly greater level than a similar polypeptide that does not contain a Trp-containing CAR sequence, is considered a compound that binds to a Trp-containing CAR sequence. Preferably, the candidate compound generates a signal within a binding assay that is at least three standard deviations above the level of signal detected for a polypeptide that does not contain a Trp-containing CAR sequence. Depending on the design of the assay, a polypeptide comprising a Trp-containing CAR sequence may be free in solution, affixed to a solid support, present on a cell surface or located within the cell. Large scale screens may be performed using automation.

Within certain embodiments, the polypeptide may be immobilized onto a solid support material, and used to affinity purify binding compounds from, for example, cell or tissue extracts. The solid support material may be any material known to those of ordinary skill in the art to which the polypeptide may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The polypeptide may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the polypeptide and functional groups on the support or may be a linkage by way of a cross-linking agent). Adsorption may be achieved by contacting the polypeptide, in a suitable buffer, with the solid support for a suitable amount of time. The contact time varies with temperature, but is typically between about 1 hour and 1 day. Covalent attachment of polypeptide to a solid support may also generally be achieved by first reacting the support with a bifunctional reagent that will react with both the support and a functional group, such as a hydroxyl or amino group, on the polypeptide using well known techniques.

Alternatively, a polypeptide may be incubated with whole cells, and interacting proteins may then be cross-linked to the polypeptide using standard techniques. Such polypeptides may be labeled with a detectable marker (e.g., a radionuclide) or may be subsequently detected using a detection reagent (e.g., an antibody) that is linked to such a marker. Within other assays, cDNA expression libraries may be screened with a labeled polypeptide to identify polynucleotides encoding proteins that interact with the labeled polypeptide. Similarly, a yeast two-hybrid system may be employed to identify interacting proteins. Other assays may be performed in a Western blot format, wherein a protein preparation from a biological sample such as a cell or tissue extract is submitted to gel electrophoresis, transferred to a suitable membrane and allowed to react with the polypeptide. The presence of the polypeptide on the membrane may then be detected using a label linked to the polypeptide or to a suitable detection reagent, such as an antibody. All of the above assays are well known to those of ordinary skill in the art, and may be performed according to standard protocols. These assays are representative only, and it will be apparent that other assays designed to evaluate binding may also be employed.

Following identification of a compound that binds to a Trp-containing CAR sequence (or a polynucleotide encoding such a compound), standard structural analyses may be performed. In general, a polynucleotide may be sequenced using well known techniques employing such enzymes as Klenow fragment of DNA polymerase I, Sequenase® (US Biochemical Corp., Cleveland Ohio) Taq polymerase (Perkin Elmer, Foster City Calif.) or thermostable T7 polymerase (Amersham, Chicago, Ill.). An automated sequencing system may be used, using instruments available from commercial suppliers such as Perkin Elmer and Pharmacia. Proteins may be partially sequenced using standard techniques, and the sequence information used to retrieve a cDNA molecule encoding the protein (e.g., using PCR or hybridization screens employing degenerate oligonucleotides).

The following Examples are offered by way of illustration and not by way of limitation.

EXAMPLES

Example 1

Preparation of Representative Cyclic Peptides

This Example illustrates the solid phase synthesis of representative cyclic peptides as cell adhesion modulating agents.

The peptides are assembled on methylbenzhydrylamine resin (MBHA resin) for the C-terminal amide peptides. The traditional Merrifield resins are used for any C-terminal acid peptides. Bags of a polypropylene mesh material are filled with the resin and soaked in dichloromethane. The resin packets are washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane is added to activate the coupling reaction. The bottle is shaken for one hour to ensure completion of the reaction. The reaction mixture is discarded and the packets washed with DMF. The N-$\alpha$-Boc is removed by acidolysis using a 55% TFA in dichloromethane for 30 minutes leaving the TFA salt of the a-amino group. The bags are washed and the synthesis completed by repeating the same procedure while substituting for the corresponding amino acid at the coupling step. Acetylation of the N-terminal is performed by reacting the peptide resins with a solution of acetic anhydride in dichloromethane in the presence of diisopropylethylamine. The peptide is then side-chain deprotected and cleaved from the resin at 0° C. with liquid HF in the presence of anisole as a carbocation scavenger.

The crude peptides are purified by reversed-phase high-performance liquid chromatography. Purified linear precursors of the cyclic peptides are solubilized in 75% acetic acid at a concentration of 2-10 mg/mL. A 10% solution of iodine in methanol is added dropwise until a persistent coloration is obtained. A 5% ascorbic acid solution in water is then added to the mixture until discoloration. The disulfide bridge containing compounds are then purified by HPLC and characterized by analytical HPLC and by mass spectral analysis.

Example 2

BiaCore

The binding of representative peptide modulating agents to Fc-E-cadherin chimeric protein in either the presence (3 mM $CaCl_2$) or absence of calcium was assessed using a BIAcore X™ Biosensor (Pharmacia Ltd., Sweden). Protein A was immobilized on the flow cells of a CM 5 sensor chip using a standard amine coupling method. The surfaces were activated with a 7 min injection of NHS/EDC, followed by a 7 min injection of protein A in 10 mM acetate pH 5.0 at a concentration of 50 ug/mL and blocked with a 7 min injection of 8 M ethanolamine, pH 8.2. This immobilization procedure resulted in the immobilization of ~8,000 RU of protein A on the CM5 chip surface. Next, Fc-E-cadherin was injected over the protein A surface to be captured on the sensor chip. These capturing steps resulted in surface densities of 3500 RU for Fc-E-cadherin.

To test compound binding to these surfaces, candidate modulating agents were injected in a three-fold dilution series over the Fc-E-cadherin-coated surfaces using six concentrations and each concentration was repeated twice. Binding responses were measured and fit to simple binding isotherms to obtain affinities, which are shown in the following table.

| Sequence | SEQ ID NO: | KD Fc-ECAD with $Ca^{++}$ (mM) | KD Fc-ECAD no $Ca^{++}$ (mM) |
|---|---|---|---|
| H-DWVIPP-$NH_2$ | 3 | 0.034 | no binding |
| H-DWVIP-$NH_2$ | 8 | 0.0361 | 0.066 |
| H-AWVIPP-$NH_2$ | 161 | 0.042 | no binding |
| H-DWVIAP-$NH_2$ | 162 | 0.017 | no binding |
| H-DWVIPA-$NH_2$ | 163 | 0.059 | no binding |
| H-DWVAPP-$NH_2$ | 164 | 21 | no binding |
| H-PWVIPP-$NH_2$ | 165 | 0.543 | no binding |

Example 3

Disruption of Human Ovarian Cancer Cell Adhesion

This Example illustrates an assay that can be used to detect the ability of candidate cell adhesion modulating agents to disrupt adhesion of human ovarian cancer cells.

The human ovarian cancer cell line SKOV3 (ATCC #HTB-77) expresses N-cadherin. SKOV3 cells are cultured in a modified MEM-based media containing 10% FCS. Cells are grown in T-250 culture flasks and maintained by periodic subculturing. Candidate modulating agents are tested on cells grown in individual wells of 96-well culture dishes (surface area of each well was 0.32 $cm^2$). Cells are harvested from flasks and seeded at a density of 50,000 cells per well in 0.1 mL media containing a candidate modulating agent at concentrations of 1, 0.1, or 0.01 mg/mL, or in the absence of the candidate modulating agent. Media control wells are also established. Cultures are evaluated periodically by microscopic examination under both bright field and phase contrast conditions. If a candidate modulating agent is incapable of disrupting cell adhesion, the SKOV3 cells will form tightly adherent monolayers. In contrast, if the candidate modulating agent is active in disrupting cell adhesion, the SKOV3 cells will not spread onto the substrata or form tightly adherent monolayers.

Example 4

Disruption of Angiogenesis

Blood vessels are composed of adherent endothelial cells. This Example illustrates an assay to detect the ability of candidate cell adhesion modulating agents to block angiogenesis (the growth of blood vessels from pre-existing blood vessels).

The chick chorioallantoic membrane assay is used to assess the effects of cyclic peptides on angiogenesis (Iruela-Arispe et al., *Molecular Biology of the Cell* 6:327-343, 1995). Candidate modulating agents are embedded in a mesh composed of vitrogen at various concentrations (e.g., 3, 17, and 33 μg/mesh). The meshes are then applied to 12-day-old chick embryonic chorioallantoic membranes. After 24 hours, the effects of the peptides on angiogenesis are assessed by computer assisted morphometric analysis.

Example 5

Disruption of Human Ovarian Cancer Cell Adhesion

This Example illustrates another assay that can be used to detect the ability of candidate cell adhesion modulating agents to disrupt human ovarian cancer cell adhesion.

The human ovarian cancer cell line OVCAR-3, which expresses E-cadherin, are cultured in RPMI supplemented with insulin and containing 20% FCS. Cells are grown in T-250 culture flasks and maintained by periodic subculturing. These cells are then harvested from flasks and seeded in individual wells of 96-well culture dishes (surface area of each well was 0.32 $cm^2$) at a density of 50,000 cells per well in 0.1 ml media containing a candidate modulating agent (at various concentrations, such as 1, 0.1, or 0.01 mg/ml). Media control wells are also established. Cultures are evaluated periodically by microscopic examination under both bright field and phase contrast conditions, and are maintained for 48 hours. If a candidate modulating agent is incapable of disrupting cell adhesion, the OVCAR-3 cells will form tightly adherent monolayers. In contrast, if the candidate modulating agent is active in disrupting cell adhesion, the OVCAR-3 cells will not form tightly adherent monolayers.

Example 6

Disruption of Melanoma Cell Adhesion

This Example illustrates an assay to detect the ability of candidate cell adhesion modulating agents to disrupt melanoma cell adhesion.

Melanoma ME115 cells are plated on glass coverslips and cultured for 24 hours in 50% keratinocyte growth medium (Clonetics, San Diego, Calif.) and 50% L15. Fresh medium containing a candidate modulating agent is then added. Following 24 hours of culture in the presence of the agent, the medium is removed and fresh medium containing the candidate modulating agent (at various concentrations such as 500 μg/ml media) is added. The cells are fixed 24 hours later with cold methanol and stored in phosphate buffered saline (PBS).

Coverslips are blocked for 1 hour in 3% ovalbumin/PBS and incubated for a further 1 hour in the presence of rabbit pan-cadherin antibody (Sigma Chemical Co., St. Louis, Mo.) diluted 1:500. Primary and secondary antibodies are diluted in PBS containing 6% normal goat serum. Following incubation in the primary antibody, coverslips are washed 3 times for 5 minutes each in PBS and incubated for 1 hour in goat anti-rabbit immunoglobulin G conjugated to fluorescein (Kiekegard and Perry, South San Francisco, Calif.) diluted 1:100. Following a further wash in PBS (3×5 minutes) coverslips are mounted in Vectashield (Vector Labs, Burlingame, Calif.) and viewed with a Zeiss infinity corrected microscope. The absence of cell membrane staining indicates that the candidate modulating agent is capable of disrupting melanoma cell adhesion. In contrast, the presence of cadherin staining over the cell membrane indicates that the candidate modulating agent is incapable of disrupting melanoma cell adhesion.

Example 7

Disruption of Breast Cancer Cell Adhesion

This Example illustrates an assay to detect the ability of candidate cell adhesion modulating agents to disrupt human breast epithelial cell adhesion.

A1N4 human breast epithelial cells are plated on glass coverslips and cultured in F12/DME containing 0.5% FCS and 10 ng/mL EGF for 24 hours. Fresh medium containing a candidate modulating agent (at various concentrations, such as 500 µg/ml media) is then added. Following 24 hours of culture in the presence of the peptides, the medium is removed and fresh medium containing the modulating agent is added. The cells are fixed 24 hours later with cold methanol and stored in phosphate buffered saline (PBS).

Coverslips are blocked for 1 hour in 3% ovalbumin/PBS and incubated for a further 1 hour in the presence of 1 µg/mL mouse anti-E-cadherin antibody (Zymed, Gaithersburg, Md.). Primary and secondary antibodies are diluted in PBS containing 6% normal goat serum. Following incubation in the primary antibody, coverslips are washed 3 times for 5 minutes each in PBS and incubated for 1 hour with goat anti-mouse conjugated to fluorescein (Kiekegard and Perry, South San Francisco, Calif.) diluted 1:100. Following a further wash in PBS (3×5 minutes) coverslips are mounted in Vectashield (Vector Labs, Burlingame, Calif.) and viewed with a Zeiss infinity corrected microscope. If the candidate modulating agent is capable of disrupting cell adhesion, the treated cells will show reduced E-cadherin staining with a stitched appearance. In addition, holes may present in the monolayer where the cells have retracted from one another. In contrast, if the candidate modulating agent is incapable of disrupting cell adhesion, cells exposed to the agent will display E-cadherin staining concentrated at points of cell-cell contact and form a tightly adherent monolayer.

Example 8

Induction of Apoptosis in Cancer Cells

This Example illustrates an assay to detect the ability of candidate cell adhesion modulating agents to induce apoptosis in human ovarian cancer cells.

SKOV3 human ovarian cancer cells cultured in the presence of a candidate modulating agent at various concentrations (e.g., 0.5 or 0.25 mg/mL) in MEM with 10% FBS are plated onto poly-L-lysine coated glass slides. Cells cultured in the absence of the candidate modulating agent is used as a control. After being cultured for 24 or 48 hours, the cells (including the control cells) are fixed with 4% paraformaldehyde for 30 minutes at room temperature. The slides are then washed three times with PBS and assessed for cell death as described by Gavrieli et al, *J. Cell. Biol.* 119:493-501, 1992 and using the in situ cell death detection kit (Boehringer Mannheim; Laval, Quebec).

Example 9

Modulating Agent-Induced Reduction in Tumor Volume

This Example illustrates an assay to detect the ability of candidate cell adhesion modulating agents to reduce tumor volume in vivo.

SKOV3 cells (ATCC) are grown to 70% confluence in Minimum Essential Medium (Life Technologies, Grand Island, N.Y.) supplemented with 10% Fetal Bovine Serum (Wisent, St. Bruno, Quebec) in a humidified atmosphere containing 5% $CO_2$. Cells were then dissociated with 0.02% PBS/EDTA. Total cell count and viable cell number are determined by trypan blue stain and a hemacytometer.

Approximately $1 \times 10^7$ cells are resuspended in 400 µl saline and injected in 6-week-old CD-1 nude mice (female, Charles River) subcutaneously. After 20 days of continuous tumor growth, the tumor-bearing animals are then injected intraperitoneally every day for 4 consecutive days with a candidate modulating agent at an appropriate concentration (e.g., 2 mg/kg and 20 mg/kg) and saline, for experimental and control respectively. Mice are sacrificed by cervical dislocation 4 days after final injection.

Tumor tissue is weighed, dissected and fixed in PBS with 4% paraformaldehyde for 48 hours. Specimens are then dehydrated in a series of alcohol incubations, and embedded in paraffin wax. Tissues are sectioned, rehydrated and stained with hematoxylin/eosin for morphological purposes, including examination of blood vessels using a blood vessel-specific marker (e.g., Von Willebrand Factor VIII) and assessment of apoptosis using the Apoptag kit (Intergen, Purchase N.Y.) according to the manufacturer's protocol, with minor modifications. More specifically, sections are deparaffinized and re-hydrated. After a five minute wash with PBS, the slides are treated with 20 µg/ml Proteinase K in PBS for 15 minutes at room temperature. This is followed by two washes with distilled water (2 minutes each wash). Endogenous peroxidase activity is blocked by incubation with 3% hydrogen peroxide (in PBS) for 5 minutes. Slides are washed twice with PBS (5 minutes/wash). Seventy-five pl of equilibration buffer (supplied with kit) is applied briefly (approximately 10 seconds) to the sections, and is followed by the application of working strength TdT (concentrated enzyme and dilution buffer solutions supplied with kit) and the enzymatic reaction allowed to proceed for 30 minutes at 37° C. The reaction is terminated by incubation in stop/wash buffer for 10 minutes (room temperature). The specimens are washed three times in PBS (1 minute/wash). Peroxidase-conjugated anti-digoxigenin antibody is added (65 µl of a diluted stock solution (supplied with kit)) to the slides, which are incubated overnight in a humidified chamber at 4° C. Subsequent visualization of apoptotic cells is achieved by washing (4×) the slides with PBS, followed by the application of the peroxidase substrate (DAB; diaminobenzidine tetrahydrochloride) for approximately 3-6 minutes at room temperature. The reaction is terminated by washing with distilled water, after which the slides were counterstained with hematoxylin. The specimens are then dehydrated through brief washes in ethanol, followed by washes in xylene, then mounted with Permount and coverslipped.

Example 10

Peptidomimetic Screening

Structure-based database screening has been performed to identify potential small molecule inhibitors that can bind to the so-called "tryptophan binding pocket" of a classical cadherin molecule (i.e., the pocket where the conserved residue tryptophan 2 of another classical cadherin molecule is located).

The Maybridge (MCC) structural database, which consists of 66,569 compounds, was one of two databases used in the structure-based screen. The 3D coordinates of the compounds were generated using the Sybyl (TRIPOS Inc., St. Louis, Mo.) program and each of the 3D structures was energetically minimized and stored in mol2 format. Hydrogen atoms and Gasteiger-Marsili atomic charges were added to these compounds using a Sybyl SPL macro, and special attention was given to the protonation state of the ionizable groups (amines, amidines) of all compounds assumed to be ionized at physiological pH (7.4). The other database used in the structure-based screen, ChemDiv (CDC) database, includes 298,440 compounds, 175,316 compounds from the international diversity collection and 123,124 compounds from 213 CombiLab 'Probe' Libraries. The 2D structural database was converted into 3D structures as described for the Maybridge databasese. The 3D structures of both databases were then used as ligands in the virtual screening.

Figure 6:
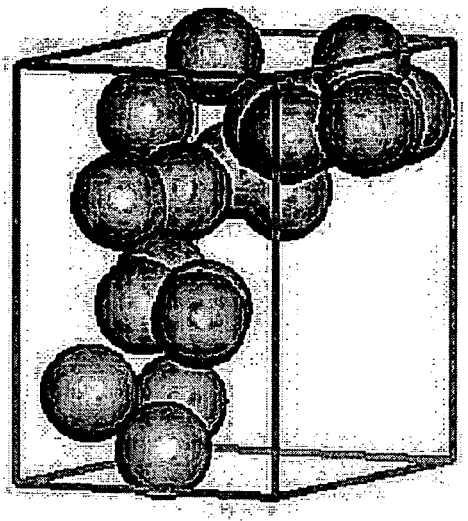
FIG. 6 shows schematic representation of a sphere cluster (sphere cluster No. 1) that represents a potential ligand or the negative image of the Trp-binding site of N-cadherin.

There were two 3D protein structures that could be used to provide the coordinates for the so-called 'tryptophan pocket' and used for virtual screening of the ligand databases. The first is the x-ray structure of N-cadherin (PDB code: 1NCJ and 1NCG). The second is the X-ray structure (PDB code: 1EDH) and NMR structure (PDB code: 1SUH) of the E-cadherin. The crystal structure of the N-cadherin (PDB code: 1NCG) (FIG. 5) was used to screen the ligand databases. No water molecules were included in the protein. Hydrogen atoms were added using standard Sybyl geometries. The N-terminal residue Trp2 in N-cadherin was selected as a bound ligand to define the active site (FIG. 6). The active site was defined as the collection of amino acids in the target enclosed with non-H contacts within a 7.0 Å radius sphere centered on the bound ligand. It comprised 23 amino acids: TRP2, ILE24, ARG25, SER26, GLY27, ARG28, LEU34, ARG35, TYR36, SER37, ILE53, ARG77, ALA78, HIS79, ALA80, VAL81, GLN87, VAL88, GLU89, ASN90, PRO91, ILE92 and ASP93.

DOCK 4.01, developed by Dr. Kuntz of USCF, was used for the identification of specific small molecule inhibitors of N-cadherin. The DOCK program is specifically designed for the identification of putative ligands that are complementary to a targeted surface area. In brief, DOCK first generates a negative image of the ligand-binding site with a set of overlapping spheres whose centers become the potential locations for ligand atoms. To rank each potential ligand, a precalculated contact-scoring grid, based on distances between potential ligand and target area atoms, and a force field-scoring grid, based on molecular mechanics interaction energies consisting of van der Waals and electrostatic components, are generated. The resulting output file for each screening contains the highest scoring compounds ranked in the order of their scores. These high scoring compounds can then be subjected to further examination and/or supplied for biological evaluation.

The calculation to generate the molecular surface for the receptor was performed using Mike Connolly's MS program from the Quantum Chemistry Program Exchange (QCPE). A Connolly surface of each protein's active site was created using a 1.50 Å probe radius. The shape of the cavities within the receptor was used to define spheres; the centers of the spheres became potential locations for the ligand atoms.

Figure 7:
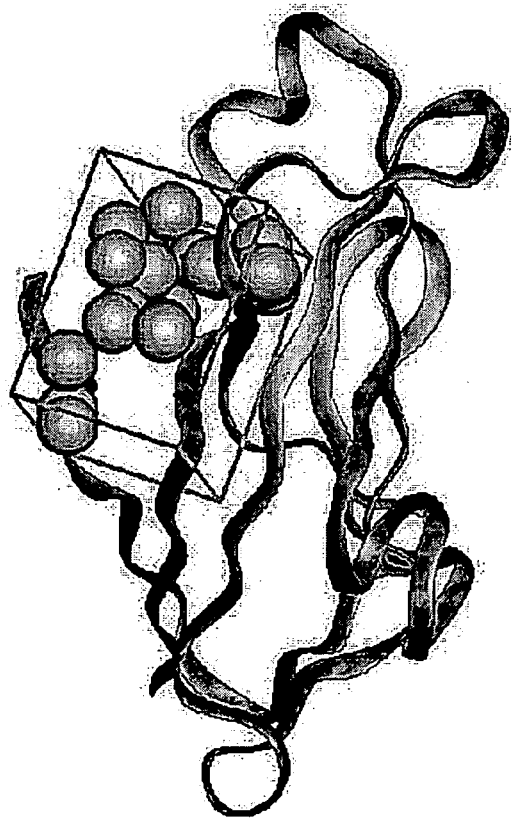
FIG. 7 shows schematic representation of the binding between a potential ligand represented by a sphere cluster (sphere cluster No. 1) and the N-terminal domain (EC1) of N-cadherin.
Figure 8:
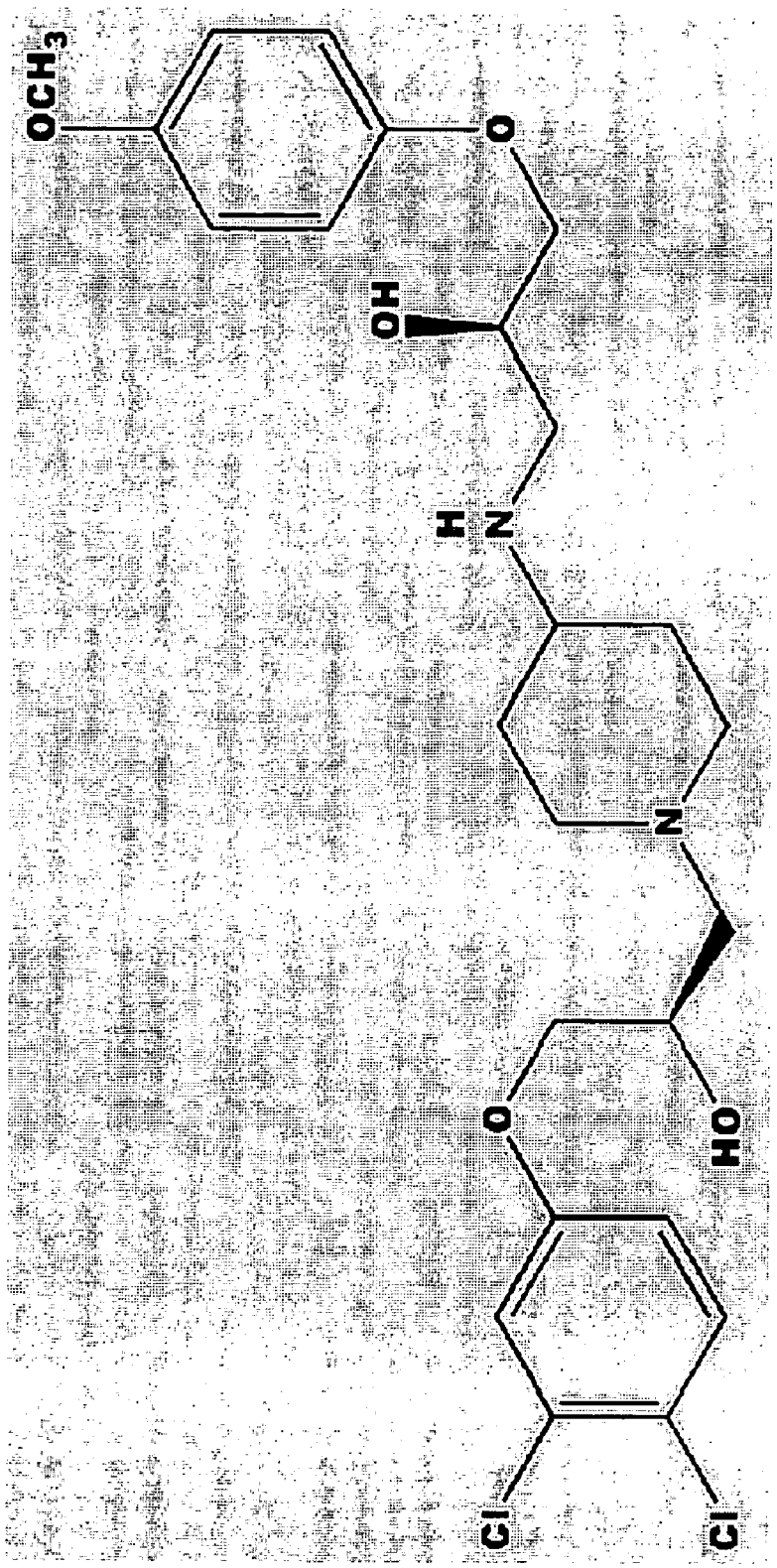
FIG. 8 shows the structure of a peptidomimetic (Compound I).

The calculation for the generation of the sphere sites was carried out using the Sphere program. Seven sphere clusters were generated. The numbers of spheres in these clusters were 24, 24, 11, 7, 3, 3, and 2, respectively. The cluster No. 1 was selected to compute scoring grids, which contains a set of 24 overlapping spheres (FIGS. 7 and 8).

The calculation of grid was accomplished using the Grid program. The Grid program generates the steric and electrostatic environment of each point. To compute interaction energies, a three-dimensional grid of 0.20 Å resolution was centered on the protein active sites. Energy scoring grids were obtained using an all atom model and a distance-dependent dielectric function ($\epsilon=4r$) with a 10 Å cutoff. Amber95 atomic charges were assigned to all protein atoms. Final grids containing 255600 (dimension: 14.10×13.87×9.64 Å) points were obtained. Theses results were used in the score calculation of the ligand orientation The small molecules from both databases were then docked into the protein active site by matching sphere centers with ligand atoms to determine the possible orientations for the ligands. A flexible docking of all molecules (peripheral search and torsion drive) with subsequent energy minimization was performed. Each molecule orientation is then scored for its fit into the so-called 'tryptophan pocket'. There are three scoring schemes in the Dock program:

1) Shape scoring, which uses a loose approximation to the Lennard-Jones potential;
2) Electrostatic scoring, which uses the program DELPHI (from where) to calculate electrostatic potential; and
3) Force-field scoring, which uses the amber potential The top scoring orientation for each molecule was then saved, and used to compare to scores of other molecules. The final result was ordered by score. For each dock run, the top 1000 compounds corresponding to the best Dock energy score for each ligand were then stored into a single multi mol2 file and rescored with 3 scoring functions: ChemScore, LB, Ludi and PMF. The top 200 are compounds for each database were then chosen for biological screening.

Example 11

Exemplary Peptidomimetic

This example illustrates the structure and cell adhesion modulating activities of an exemplary peptidomimetic.

Figure 9:
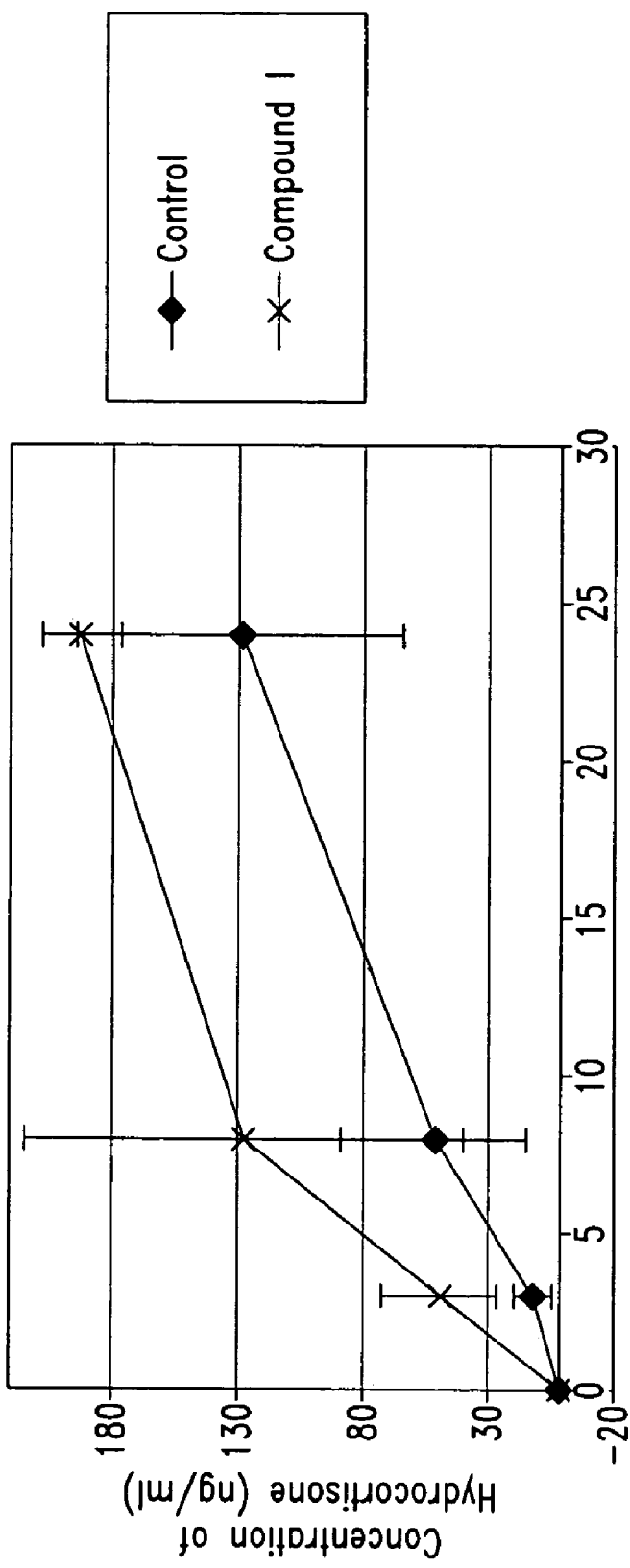
FIG. 9 shows the effect of Compound I (10 μg/ml) on the transdermal delivery of hydrocortisone through nude mouse skin in Fraz cell assay.
Figure 10:
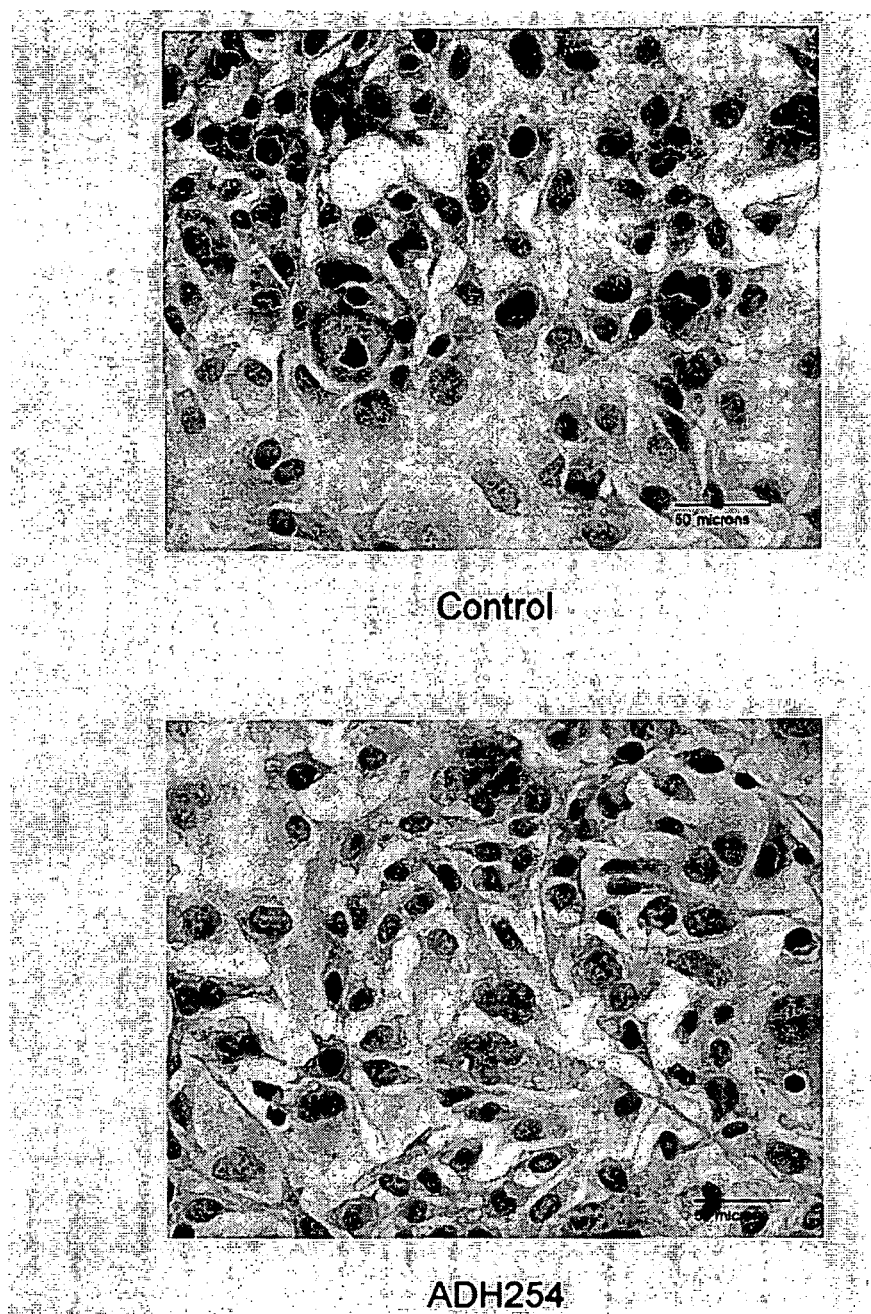
FIG. 10 demonstrates the cell adhesion modulating effects of the Trp-containing CAR sequence ADH254 (H-DWVIPP-NH2 (SEQ ID NO: 3); classical cadherin derived peptide) on SKOV3 human ovarian cancer cells.

The structure of Compound I is shown in FIG. 9.

The activity of Compound I in enhancing transdermal drug permeation was assayed using a Franz Cell apparatus. Nude, athymic, CD1 mice skins were sandwiched between the upper and lower chambers of a Franz Cell apparatus. Hydrocortisone in the absence or presence of Compound I (10 µg/ml in HBSS+1% BSA containing 2 mM $CaCl_2$) was added to the top chamber, while the lower chamer was filled with PBS. Samples from the lower chamber were taken via a sampling port at three hour intervals, and at that time the lower chamber was re-filled with fresh PBS. The results of this assay show that Compound I significantly increased the permeation of hydrocortisone through intact mouse skin (FIG. 11).

Example 12

Effects of ADH254 (H-DWVIPP-NH2; Classical Cadherin Derived Peptide) on SKOV3 Human Ovarian Cancer Cells We investigated the effects of the linear peptide ADH254 (H-DWVIPP-NH2; classical cadherin derived peptide) on confluent cultures of SKOV3 cells. SKOV3 human ovarian cancer cells express N-cadherin. The cells were cultured in minimum essential medium (MEM) supplemented with 10% fetal calf serum, non-essential amino acids, fungizone, penicillin-streptomycin, and gentamicin in a humidified atmosphere (5% $CO_2$) at 37° C. All culture reagents were purchased from GIBCO (Burlington, ON). ADH254 (1 mg/ml of culture medium) was added to confluent cultures of SKOV3 cells. After 24 hours of treatment, the cells were fixed with 4% paraformaldehyde, followed by 3 washes with phosphate buffered saline, and then stained with hematoxylin. Control cultures were grown in the absence of peptide.

Microscopic examination of SKOV3 confluent cultures treated with ADH254, for 24 hours revealed that this peptide caused disruption of the confluent SKOV3 monolayers within 24 hours of addition to the tissue culture medium (see FIG. 12). The peptide caused the SKOV3 cells to detach from one another and adopt an elongated, fibroblast-like morphology. These observations indicate that Trp containing peptides can disrupt cell adhesion.

From the foregoing, it will be evident that although specific embodiments of the invention have been described herein for the purpose of illustrating the invention, various modifications may be made without deviating from the spirit and scope of the invention.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

What is claimed is:

1. A cell adhesion modulating agent ranging in size from 6 to 15 amino acid residues that
   (a) modulates cadherin-mediated cell adhesion; and
   (b) comprises the amino acid sequence DWVIPP (SEQ ID NO: 3)

2. The cell adhesion modulating agent of claim 1 wherein the agent is a linear peptide.

3. The cell adhesion modulating agent of claim 1 wherein the agent is a cyclic peptide.

4. The cell adhesion modulating agent of claim 1 wherein the peptide comprises an N-terminal or C-terminal modification.

5. The cell adhesion modulating agent of claim 4 wherein the N-terminal modification is N-acetylation.

6. The cell adhesion modulating agent of claim 1 linked to a heterologous compound.

7. The cell adhesion modulating agent of claim 6 wherein the heterologous compound is a pharmaceutically active compound.

8. The cell adhesion modulating agent of claim 1 linked to a solid support.

9. A composition comprising a cell adhesion modulating agent of claim 1 in combination with a physiologically acceptable carrier.

* * * * *